(12) United States Patent
Oliver-Perez et al.

(10) Patent No.: US 11,248,230 B2
(45) Date of Patent: Feb. 15, 2022

(54) THERAPEUTIC AGENTS

(71) Applicant: IP2IPO Innovations Limited, London (GB)

(72) Inventors: Eduardo Oliver-Perez, London (GB); Lan Zhao, London (GB); Martin Wilkins, London (GB); Tim Aitman, London (GB)

(73) Assignee: IP2IPO Innovations Limited, London (GB)

( * ) Notice: Subject to any disclaimer, the term of this patent is extended or adjusted under 35 U.S.C. 154(b) by 195 days.

(21) Appl. No.: 16/432,645

(22) Filed: Jun. 5, 2019

(65) Prior Publication Data

US 2020/0017860 A1 Jan. 16, 2020

Related U.S. Application Data

(62) Division of application No. 15/747,292, filed as application No. PCT/GB2016/052297 on Jul. 27, 2016, now abandoned.

(30) Foreign Application Priority Data

Jul. 28, 2015 (GB) ..................... 1513299

(51) Int. Cl.
| | | |
|---|---|---|
| *C12N 15/11* | (2006.01) | |
| *C12N 15/113* | (2010.01) | |
| *G01N 33/50* | (2006.01) | |
| *A61K 31/7105* | (2006.01) | |
| *A61P 9/12* | (2006.01) | |
| *A61P 11/00* | (2006.01) | |
| *C07K 16/28* | (2006.01) | |
| *C12Q 1/6883* | (2018.01) | |
| *G01N 33/68* | (2006.01) | |

(52) U.S. Cl.
CPC ...... *C12N 15/1138* (2013.01); *A61K 31/7105* (2013.01); *A61P 9/12* (2018.01); *A61P 11/00* (2018.01); *C07K 16/28* (2013.01); *C12Q 1/6883* (2013.01); *G01N 33/5008* (2013.01); *G01N 33/6893* (2013.01); *C07K 2317/76* (2013.01); *G01N 2333/4703* (2013.01); *G01N 2800/12* (2013.01)

(58) Field of Classification Search
CPC ... C12N 15/1138; A61K 31/7105; A61P 9/12; A61P 11/00
See application file for complete search history.

(56) References Cited

U.S. PATENT DOCUMENTS

2018/0237784 A1  8/2018  Oliver-Perez et al.

FOREIGN PATENT DOCUMENTS

| WO | 2006128902 A1 | 7/2006 |
| WO | 2017017446 A1 | 2/2017 |

OTHER PUBLICATIONS

International Search Report and Written Opinion of PCT/GB2016/052297, dated Nov. 8, 2016, 11 Pages.
Combined Search and Examination Report of GB1513299.6, dated Apr. 20, 2016, 9 Pages.
Bernal et al., A Role for Zinc in Regulating Hypoxia-Induced Contractile Events in Pulmonary Endothelium, 2011, Am. J. Physiol. Lung Cell Mol. Physiol., vol. 300, pp. L874-L886.
Bernal et al, Nitric Oxide-Mediated Zinc Release Contributes to Hypoxic Regulation of Pulmonary Vascular Tone, 2008, Circulation Research, vol. 102(12), pp. 1575-1583.
Oliver et al, Oral Abstracts Cardiovascular Pharmacology, 2013, Basic & Clinical Pharmacology & Toxicology, vol. 113(Suppl. 1), pp. 12-20.
Zhao et al, The Zinc Transporter ZIP12 Regulates the Pulmonary Vascular Response to Chronic Hypoxia, 2015, Nature, vol. 524(7565), 18 Pages.

*Primary Examiner* — Ekaterina Poliakova-Georgantas
(74) *Attorney, Agent, or Firm* — Linda B. Huber; Nixon Peabody LLP

(57) ABSTRACT

The present invention related to identification of therapeutic agents of the treatment, diagnosis, and prevention of pulmonary hypertension.

5 Claims, 31 Drawing Sheets

Specification includes a Sequence Listing.

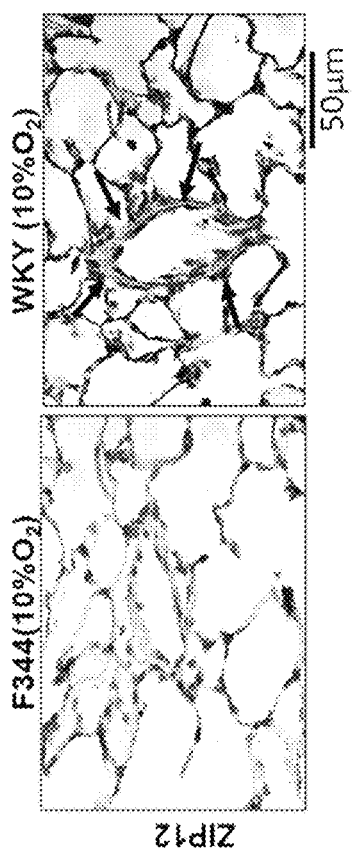
FIG. 2A
FIG. 2B
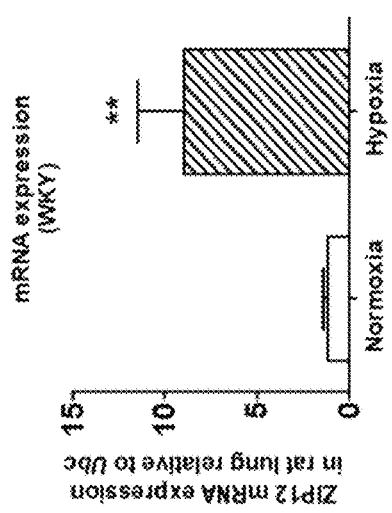
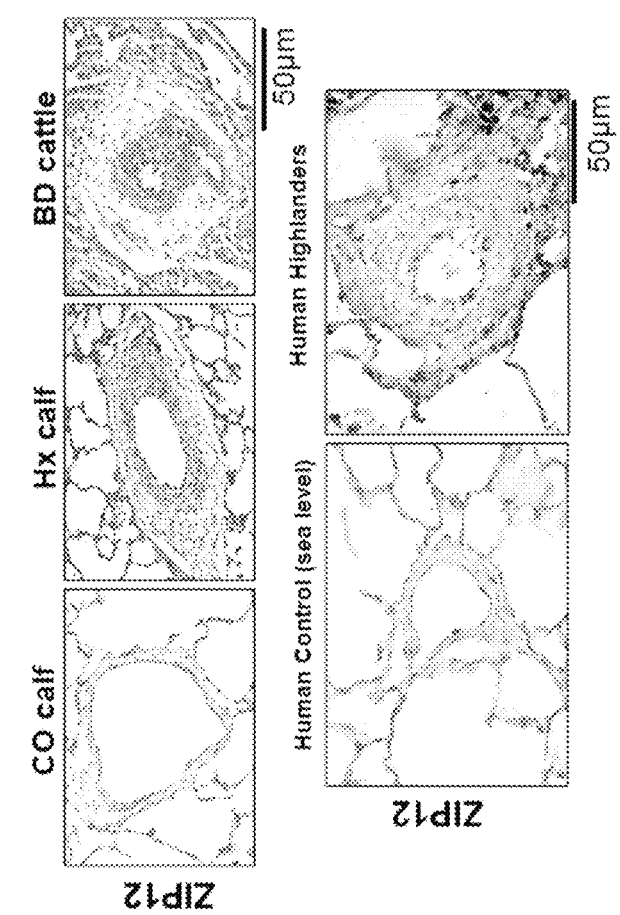
FIG. 2C

Figure 5F:
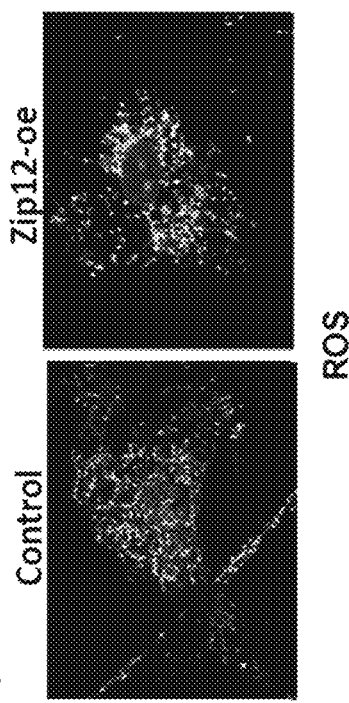
Figure 5F:
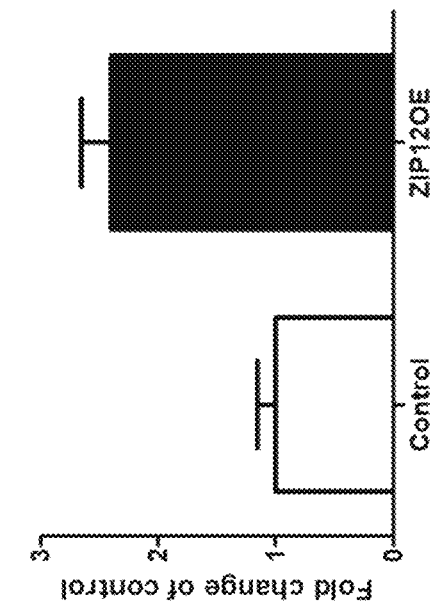
Figure 5E:
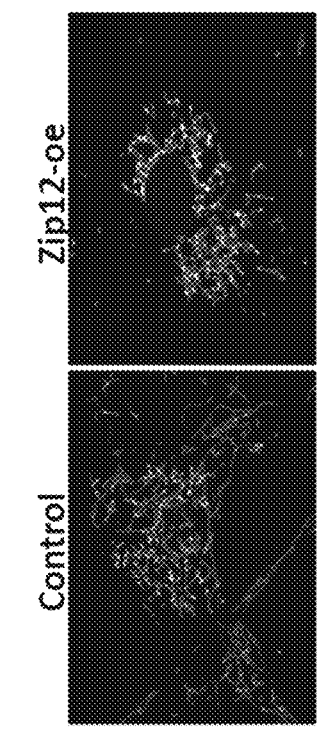
Figure 5E:
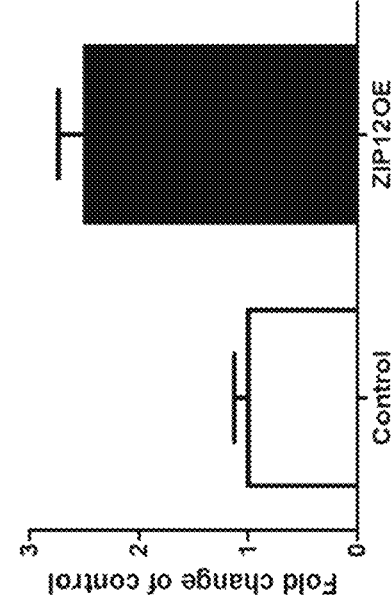

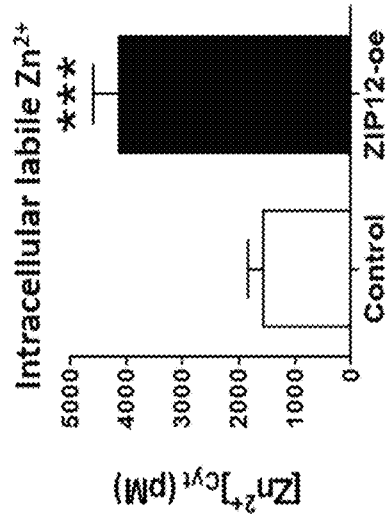
FIG. 5B
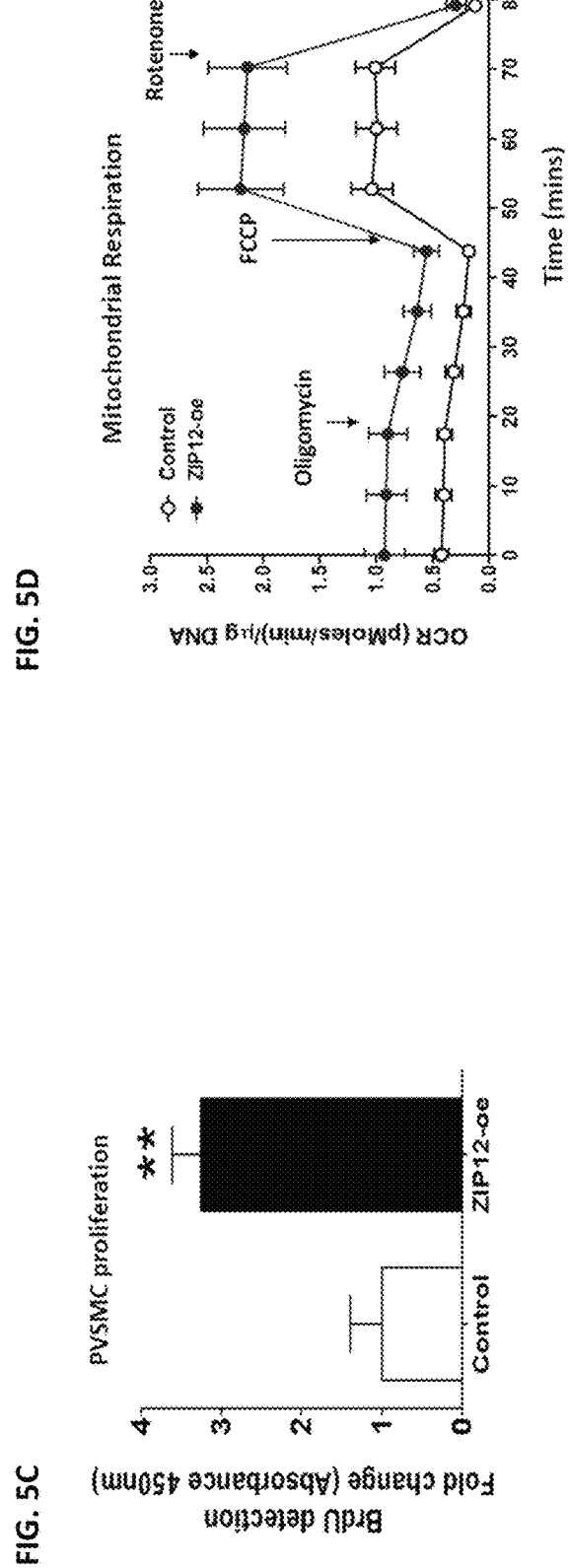
FIG. 5D
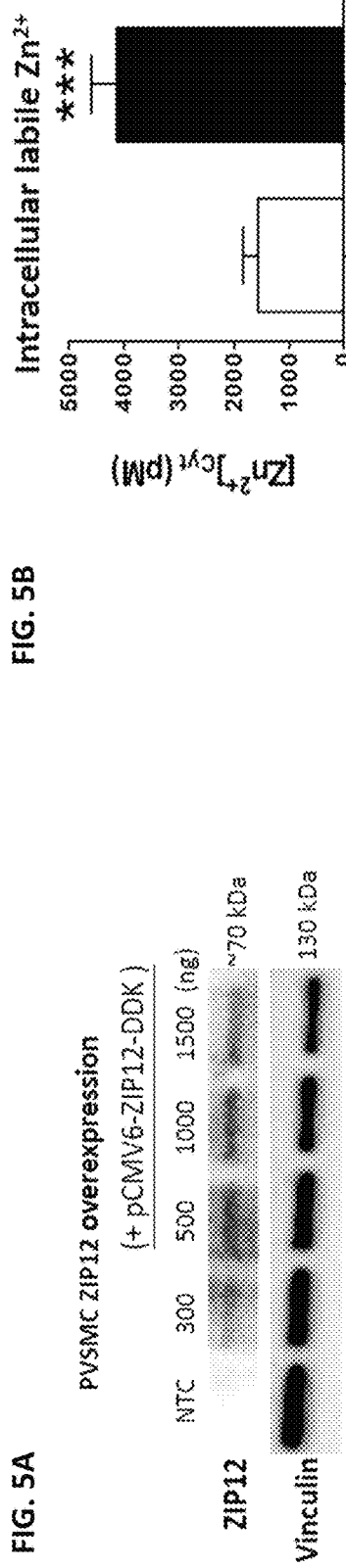
FIG. 5A
FIG. 5C

| Rat chr 17 Marker | Genetic map SHRSP x BN | Physical map possition | Primers FORWARD | REVERSE | Expected size (bp) WKY | F344 | Genotyping information R47A | Sub A | Sub B | Sub C |
|---|---|---|---|---|---|---|---|---|---|---|
| D17Rat41 | 38.27 | 80234337 - 80234511 | CCTTTCCCTTTCCACTCTCC | GGTAAGGGTGGTGGCAGTAG | 171 | 157 | WW | WW | WW | WW |
| D17Rat44 | 40.89 | 81612362 - 81612488 | CAGACAAAACCCAGCATTT | AGCAGAAAGAACCAGGCAGA | 133 | 121 | WW | WW | WW | WW |
| D17Got91 | | 82277435 - 82277611 | CCAGACACCAACATCACACC | CCTTCATGTGTGGAGTGTTATG | 160 | 176 | FF | FF | WW | WW |
| D17Rat43 | 40.89 | 82337230 - 82337376 | CACTCACTTGCTGGCTGTCT | GAGAAGAAGCTGGAGAGGCA | 150 | 124 | FF | FF | WW | WW |
| D17Rat42 | 40.33 | 82505422 - 82505562 | TGCCGCTATTAAAAAGTAACTGC | CCAAAGGCATAAAAATCTTTCC | 141 | 121 | FF | FF | WW | WW |
| D17Rat62 | 42.35 | 83479938 - 83480058 | GAAAGGATGGCAGGTTTTTG | TCCACAGGTCACTGTCACT | 143 | 121 | FF | FF | WW | WW |
| D17Rat46 | 42.33 | 83600152 - 83600282 | TGGGTTCTTTCATTCCTTGC | GCTCACCCACACACATTC | 135 | 125 | FF | FF | WW | WW |
| D17Rat47 | 43.34 | 85072353 - 85072475 | CCCTGCTTTCTGCTTTGAAC | TGCATATACGAATTACAGCTCAA | 114 | 126 | FF | FF | FF | WW |
| Del85862103 | | 85862060 - 85862261 | CACCATGAGCTCAGCAGTGT | ACACCGTCTGGCTCTCTCAG | 203 | 193 | FF | WW | FF | WW |
| In85923365 | | 85923262 - 85923495 | ACCTTTGGCTCGGTCCTATC | AAACTTGGGTACCAGCACCA | 235 | 243 | FF | WW | FF | WW |
| D17Got93 | | 86032700 - 86032904 | CACTACACCTCCCAACGTCC | CTGTTGTGCCTCCTGACTAATG | 227 | 215 | FF | WW | FF | WW |
| D17Mit8 | 45.19 | 87465135 - 87465345 | GGTCGGCATTATGGCTAAGA | CTATAGCCTCTAGGGAGGGG | 193 | 195 | FF | WW | FF | WW |
| D17Rat60 | 45.19 | 88268817 - 88269054 | GGGGTCCAGCACTTAGCAT | GTTTGATCATGGGGACGTT | 239 | 241 | FF | WW | FF | WW |
| D17Rat48 | 45.19 | 88667790 - 88667952 | CACATGTCTAACTTGCCACATACA | TTTGCTGTTTCTTGTTCATGTG | 166 | 156 | FF | WW | FF | WW |
| Del89391756 | | 89391713 - 89391951 | TCCATGTTTTATCACCGGAAG | ATCTGATGCATGCCATAGCC | 230 | 238 | FF | WW | FF | WW |
| In90455808 | | 90455697 - 90455921 | AAGTTAGCCTTCCCCAAGGA | TCTGGTCTTTCCCATGTTCC | 233 | 225 | FF | WW | FF | WW |
| D17Rat131 | 47.54 | 93347784 - 93347990 | TTAAGAAGGGCAAGCAAGGA | TCCCCATAAAAAGAAAAGGAA | 203 | 213 | FF | WW | FF | FF |
| D17Rat51 | 47.54 | 96587775 - 96587905 | TCCCACTGGTCAATCCATTT | ACATGCAGACAGAACATTCCT | 144 | 148 | FF | WW | FF | FF |

THERAPEUTIC AGENTS

CROSS-REFERENCE TO RELATED APPLICATIONS

This application is a divisional of U.S. patent application Ser. No. 15/747,292 filed Jan. 24, 2018, which is a National Phase of International Application No. PCT/GB2016/052297 filed Jul. 27, 2016, currently pending, which designated the U.S. and that International Application was published under PCT Article 21(2) in English, which also includes a claim of priority under 35 U.S.C. § 119(a) and § 365(b) to British patent application No. GB 1513299.6 filed Jul. 28, 2015, the entirety of which is hereby incorporated by reference.

FIELD OF THE INVENTION

The present invention relates to identification of therapeutic agents for the treatment, diagnosis, and prevention of pulmonary hypertension. The invention extends to the development and use of agents that modulate a particular gene and associated protein, which have a fundamental role in the pathology of pulmonary hypertension.

BACKGROUND OF THE INVENTION

Pulmonary hypertension is a pathological condition characterised by elevated pulmonary artery pressure and structurally remodeled pulmonary vessels. The current treatments for pulmonary hypertension centre on the pharmacological manipulation of signaling mechanisms used by vasoactive factors and have limited therapeutic benefit. There exists a significant unmet medical need for new therapeutics and diagnostics for this potentially lethal condition.

The typical response of the adult mammalian pulmonary circulation to a low oxygen environment is vasoconstriction and structural remodelling of pulmonary arterioles, leading to chronic elevation of pulmonary artery pressure (pulmonary hypertension) and right ventricular hypertrophy. Some mammals, however, exhibit genetic resistance to hypoxia-induced pulmonary hypertension (WILKINS, M. R. et al, Pathophysiology and treatment of high-altitude pulmonary vascular disease. Circulation. 2015, 131, 582-590; ZHAO, L. et al., Right ventricular hypertrophy secondary to pulmonary hypertension is linked to rat chromosome 17: evaluation of cardiac ryanodine Ryr2 receptor as a candidate. Circulation. 2001, 103, 442-447; RHODES, J., Comparative physiology of hypoxic pulmonary hypertension: historical clues from brisket disease. Journal of applied physiology. 2005, 98, 1092-1100). The inventors have previously reported that the Fisher 344 (F344) rat strain is resistant to hypoxia-induced pulmonary hypertension compared to the Wistar Kyoto (WKY) strain (ZHAO, L. et al., Right ventricular hypertrophy secondary to pulmonary hypertension is linked to rat chromosome 17: evaluation of cardiac ryanodine Ryr2 receptor as a candidate. Circulation. 2001, 103, 442-447). However, the cause of this resistance as never been identified.

SUMMARY OF THE INVENTION

The inventors have now utilised a congenic breeding program and comparative genomics to exploit this variation in the rat and have identified the gene, Slc39a12, as a major regulator of hypoxia-induced pulmonary vascular remodelling. Slc39a12 encodes the zinc transporter, ZIP12. They found that ZIP12 expression is increased in many cell types, including endothelial, smooth muscle and interstitial cells, in the remodeled pulmonary arterioles of rats, cows and humans susceptible to hypoxia-induced pulmonary hypertension. The inventors have shown that ZIP12 expression in pulmonary vascular smooth muscle cells is hypoxia-dependent and that targeted inhibition of ZIP12 inhibits the rise in intracellular labile zinc in hypoxia-exposed pulmonary vascular smooth muscle cells and their proliferation in culture. The inventors demonstrate that genetic disruption of ZIP12 expression attenuates the development of pulmonary hypertension in rats housed in a hypoxic atmosphere. This entirely novel and unexpected insight into the fundamental role of a zinc transporter in mammalian pulmonary vascular homeostasis provides a new drug target for the pharmacological management of pulmonary hypertension.

The inventors provide data showing that the invention is relevant to species other than rats. In particular, the applicability to cattle and humans is demonstrated. Moreover ZIP12 is upregulated in the pulmonary vasculature in other presentations of pulmonary hypertension where hypoxic stress may be mediated by iron deficiency or inflammation.

The invention described herein is based upon the inventors' surprising discovery that ZIP12, barely detectable in normal lung exposed to a normal atmosphere, is upregulated in response to chronic alveolar hypoxia exposure, and that disruption of ZIP12 attenuates the associated pathology.

Therefore, in a first aspect the invention relates to a method of screening for molecules for use in the treatment or prevention of pulmonary hypertension, wherein the molecules are capable of altering the biological activity or levels of ZIP12, wherein the method comprises:

i) contacting a test molecule with one or more cells expressing ZIP12, ii) measuring the change in activity or levels of ZIP12 and, iii) selecting molecules capable of altering activity or levels of ZIP12.

Accordingly, the identification of the role of ZIP12 in pulmonary hypertension underpins the development of screens to identify molecules that are capable of inhibiting or attenuating expression or activity of ZIP12 and which molecules may therefore be useful in ameliorating the development and effects of pulmonary hypertension.

In essence, the method of the first aspect of the invention involves assaying potential molecules for their ability to effect the expression, protein level, or activity of ZIP12. Either the protein, ZIP12, or the expression of the gene, Slc39a12, can be examined. Those molecules which are capable of affecting ZIP12 are candidates for use in the treatment or prevention in pulmonary hypertension. In a particular embodiment, the molecules are tested for the capability to inhibit expression of Slc39a12, inhibit activity of ZIP12, or reduce levels of ZIP12.

In a particular embodiment, the test molecules are interfering nucleic acid molecules including: antisense oligonucleotides, siRNA, or dsRNA, which specifically target a portion of an mRNA encoding ZIP12 (the mRNA produced from Slc39a12). A functional interfering nucleic acid molecule, including antisense oligonucleotides, siRNA molecules, or dsRNA molecules, is capable of specifically downregulating a target gene.

In an embodiment, test molecules can be those which inhibit ZIP12 expression by a mechanism which is referred to as RNA interference or post-transcriptional gene silencing. The siRNA molecule and RNAi molecule respectively, according to the present invention is thus suitable to trigger the RNA interference response resulting preferably in the knock-down of the mRNA for the target molecule. Insofar, this kind of nucleic acid molecule is suitable to decrease the expression of a target molecule by decreasing the expression at the level of mRNA.

The basic design of siRNA molecules or RNAi molecules, which mostly differ in the size, is such that the nucleic acid molecule comprises a double-stranded structure. The double-stranded structure comprises a first strand and a second strand. More preferably, the first strand comprises a first stretch of contiguous nucleotides and the second stretch comprises a second stretch of contiguous nucleotides. At least the first stretch and the second stretch are essentially complementary to each other. Such complementarity is typically based on Watson-Crick base pairing or other base-pairing mechanism known to the one skilled in the art, including but not limited to Hoogsteen base-pairing and others. It will be acknowledged by the one skilled in the art that depending on the length of such double-stranded structure a perfect match in terms of base complementarity is not necessarily required. However, such perfect complementarity is preferred in some embodiments. In a particularly preferred embodiment the complementarity and/or identity is at least 75%, 80%, 85%, 90% or 95%.

A mismatch is also tolerable, mostly under the proviso that the double-stranded structure is still suitable to trigger the RNA interference mechanism, and that preferably such double-stranded structure is still stably forming under physiological conditions as prevailing in a cell, tissue and organism, respectively, containing or in principle containing such cell, tissue and organ. More preferably, the double-stranded structure is stable at 37° C. in a physiological buffer. It will be acknowledged by the ones skilled in the art that this kind of mismatch can preferably be contained at a position within the nucleic acid molecule according to the present invention different from the core region.

DNA-containing oligonucleotides which are capable of specifically down-regulating a target gene are also considered suitable test molecules. In this case the targeted gene would be Slc39a12.

As used herein, "expression" of ZIP12 is a broad term referring all processes by which ZIP12 protein is produced within a cell. This includes transcription, RNA processing, translation, modification and folding of the protein. Molecules which affect the production of ZIP12 protein are considered to affect ZIP12 "expression". Molecules which affect ZIP12 "levels" are those which affect either the production or the breakdown of ZIP12.

As expanded upon below, in an embodiment of the invention the model for assaying ZIP12 levels or activity before, during, or after treatment with a putative ZIP12 modulating agent, is an in vitro cell or cell line. The Examples provide further information relating to those ZIP12 expressing cells that are suitable for use in the method of screening of the invention. A non-limiting example of a suitable cell type is human pulmonary artery smooth muscle cells (HPASMCs) which will up-regulate ZIP12 when exposed to hypoxia (2% $O_2$, 5% $CO_2$, 92% $N_2$), unless an inhibitor is present. In a particular embodiment, the cell comprises a zinc probe such as eCALWY-4, which allows intracellular free zinc to be measured and hence ZIP12 activity.

In another embodiment, as explained below, the model for assaying ZIP12 expression is a cell comprising a ZIP12 reporter vector, preferably a luciferase reporter, allowing ZIP12 expression to be directly assessed.

Other reporter systems are known in the art and would also be suitable for assaying ZIP12 levels or activity.

Alternatively, in another embodiment, standard techniques such as, but not limited to, Western Blotting, rtPCR, and qPCR can be used to measure ZIP12 levels after treatment with a putative ZIP12 modulating agent.

In another embodiment the model for assaying putative ZIP12 modulating agents is a non-human animal which is susceptible to hypoxia-induced pulmonary hypertension when exposed to a low oxygen environment. When treated with a ZIP12 modulating agent these animals will not develop pulmonary hypertension, allowing molecules suitable for use in the treatment or prevention of pulmonary hypertension to be identified.

In a particular embodiment of the screening method according to the first aspect of the invention, the method further comprises administering the selected molecules to a non-human animal with hypoxia-induced pulmonary hypertension and further selecting those that ameliorate or reduce the symptoms thereof.

In another embodiment the non-human animal model is susceptible to pulmonary hypertension caused by other techniques known in the art such as, but not limited to, iron deficient models and monocrotaline-induced disease.

Both the protein ZIP12 and the gene Slc39a12 are known in the art, and their nucleic acid and amino acid sequences are thus publically available.

In another aspect, a method of diagnosing pulmonary hypertension is provided. The inventors have unexpectedly demonstrated that ZIP12 is upregulated in response to chronic hypoxic stress. Upregulation of ZIP12 in lung tissues can therefore be used to identify patients with pulmonary hypertension. Many techniques are known in the art and some of these are described in the Examples for measuring ZIP12 protein levels, or Slc39a12 gene expression, in lung tissues. The method comprises assessing ZIP12 levels in a sample of lung tissue obtained from an individual wherein increased ZIP12 levels are indicative of pulmonary hypertension or assessing Slc39a12 gene activity in a sample of lung tissue obtained from an individual wherein increased expression levels are indicative of pulmonary hypertension.

In another aspect, a method of treating humans or non-human animals by provision of a molecule capable of down-regulating or inhibiting ZIP12, or Slc39a12 gene expression, is provided. In an embodiment, this molecule can be a siRNA complementary to a corresponding sequence of the mRNA encoding ZIP12 (the mRNA expressed from the Slc39a12 gene). In another embodiment this molecule can be an antibody, or fragment thereof, capable of binding to and inhibiting ZIP12. In another embodiment, the molecule can be a biological agent, a protein, a nucleic acid, or a pharmaceutical agent. The unexpected finding that disruption of ZIP12 attenuates pulmonary hypertension provides a method of using these inhibitors to treat or prevent or ameliorate the symptoms of pulmonary hypertension.

In an aspect, a method of treating or preventing pulmonary hypertension by modulating, antagonising or agonising ZIP12 activity or modulating ZIP12 protein levels is provided. In a particular embodiment, ZIP12 is modulated by altering the expression of gene Slc39a12.

In a particular embodiment, the molecule capable of down-regulating or inhibiting ZIP12, or Slc39a12 gene expression, is part of a pharmaceutical composition comprising a pharmaceutical excipient, diluent, and/or carrier. In another embodiment, the method comprises delivery of the composition or molecule to lung tissue. In particular embodiments, this is accomplished by a physical method, a chemical method, or by use of a vector. These methods include transfection and transduction.

As used herein, a nucleic acid, such as siRNA, double stranded RNA capable of RNA interference or an antisense molecule, is "complementary" to another when the sequences are at least about 45-55%, typically at least about 70-75%, more typically at least about 80-85%, more typically greater than about 90%, and more typically 100% complementary.

As aforementioned, the molecule that can inhibit the activity of ZIP12 may be an antibody or an antigen binding fragment thereof. The antibody or antigen-binding fragment thereof may be monovalent, divalent or polyvalent. Monovalent antibodies are dimers (HL) comprising a heavy (H) chain associated by a disulphide bridge with a light chain (L). Divalent antibodies are tetramer (H2L2) comprising two dimers associated by at least one disulphide bridge. Polyvalent antibodies may also be produced, for example by linking multiple dimers. The basic structure of an antibody molecule consists of two identical light chains and two identical heavy chains which associate non-covalently and can be linked by disulphide bonds. Each heavy and light chain contains an amino-terminal variable region of about 110 amino acids, and constant sequences in the remainder of the chain.

The variable region includes several hypervariable regions, or Complementarity Determining Regions (CDRs), that form the antigen-binding site of the antibody molecule and determine its specificity for the antigen, i.e. ZIP12, or variant or fragment thereof (e.g. an epitope). On either side of the CDRs of the heavy and light chains is a framework region, a relatively conserved sequence of amino acids that anchors and orients the CDRs. Antibody fragments may include a bi-specific antibody (BsAb) or a chimeric antigen receptor (CAR).

The constant region consists of one of five heavy chain sequences ($\mu$, $\gamma$, $\zeta$, $\alpha$, or $\epsilon$) and one of two light chain sequences ($\kappa$ or $\lambda$). The heavy chain constant region sequences determine the isotype of the antibody and the effector functions of the molecule.

Preferably, the antibody or antigen-binding fragment thereof is isolated or purified. In one preferred embodiment, the antibody or antigen-binding fragment thereof comprises a polyclonal antibody, or an antigen-binding fragment thereof. The antibody or antigen-binding fragment thereof may be generated in a suitable animal, such as a rabbit, mouse or rat.

Preferably, the antibody or antigen-binding fragment thereof is obtained by immunising a host animal with ZIP12, or a variant or fragment thereof, and then collecting the antibody or antigen-binding fragment thereof.

In another preferred embodiment, the antibody or antigen-binding fragment thereof comprises a monoclonal antibody or an antigen-binding fragment thereof. Preferably, the antibody of the invention is a human antibody. As used herein, the term "human antibody" can mean an antibody, such as a monoclonal antibody, which comprises substantially the same heavy and light chain CDR amino acid sequences as found in a particular human antibody exhibiting immunospecificity for ZIP12, or a variant or fragment thereof. An amino acid sequence, which is substantially the same as a heavy or light chain CDR, exhibits a considerable amount of sequence identity when compared to a reference sequence. Such identity is definitively known or recognizable as representing the amino acid sequence of the particular human antibody.

Substantially the same heavy and light chain CDR amino acid sequence can have, for example, minor modifications or conservative substitutions of amino acids. Such a human antibody maintains its function of selectively binding to ZIP12 or a variant or fragment thereof.

The term "human monoclonal antibody" can include a monoclonal antibody with substantially or entirely human CDR amino acid sequences produced, for example by recombinant methods such as production by a phage library, by lymphocytes or by hybridoma cells.

The term "humanised antibody" can mean an antibody from a non-human species (e.g. mouse or rabbit) whose protein sequences have been modified to increase their similarity to antibodies produced naturally in humans.

The antibody may be a recombinant antibody. The term "recombinant human antibody" can include a human antibody produced using recombinant DNA technology.

The term "antigen-binding region" can mean a region of the antibody having specific binding affinity for its target antigen, for example, ZIP12, or a variant or fragment thereof. Preferably, the fragment is an epitope. The binding region may be a hypervariable CDR or a functional portion thereof. The term "functional portion" of a CDR can mean a sequence within the CDR which shows specific affinity for the target antigen. The functional portion of a CDR may comprise a ligand which specifically binds to ZIP12 or a fragment thereof.

The term "CDR" can mean a hypervariable region in the heavy and light variable chains. There may be one, two, three or more CDRs in each of the heavy and light chains of the antibody. Normally, there are at least three CDRs on each chain which, when configured together, form the antigen-binding site, i.e. the three-dimensional combining site with which the antigen binds or specifically reacts. It has however been postulated that there may be four CDRs in the heavy chains of some antibodies.

The definition of CDR also includes overlapping or subsets of amino acid residues when compared against each other. The exact residue numbers which encompass a particular CDR or a functional portion thereof will vary depending on the sequence and size of the CDR. Those skilled in the art can routinely determine winch residues comprise a particular CDR given the variable region amino acid sequence of the antibody.

The term "functional fragment" of an antibody can mean a portion of the antibody which retains a functional activity. A functional activity can be, for example antigen binding activity or specificity. A functional activity can also be, for example, an effector function provided by an antibody constant region. The term "functional fragment" is also intended to include, for example, fragments produced by protease digestion or reduction of a human monoclonal antibody and by recombinant DNA methods known to those skilled in the art. Human monoclonal antibody functional fragments include, for example individual heavy or light chains and fragments thereof, such as VL, VH and Fd; monovalent fragments, such as Fv, Fab, and Fab'; bivalent fragments such as F(ab')2; single chain Fv (scFv); and Fc fragments.

The term "VL fragment" can mean a fragment of the light chain of a human monoclonal antibody which includes all or part of the light chain variable region, including the CDRs. A VL fragment can further include light chain constant region sequences. The term "VH fragment" can means a fragment of the heavy chain of a human monoclonal antibody which includes all or part of the heavy chain variable region, including the CDRs. The term "Fd fragment" can mean the light chain variable and constant regions coupled to the heavy chain variable and constant regions, i.e. VL, CL and VH, CH-1. The term "Fv fragment" can mean a monovalent antigen-binding fragment of a human monoclonal antibody, including all or part of the variable regions of the heavy and light chains, and absent of the constant regions of the heavy and light chains. The variable regions of the heavy and light chains include, for example, the CDRs. For example, an Fv fragment includes all or part of the amino terminal variable region of about no amino acids of both the heavy and light chains.

The term "Fab fragment" can mean a monovalent antigen-binding fragment of a human monoclonal antibody that is larger than an Fv fragment. For example, a Fab fragment includes the variable regions, and all or part of the first constant domain of the heavy and light chains. Thus, a Fab fragment additionally includes, for example, amino and residues from about 110 to about 220 of the heavy and light chains.

The term "Fab' fragment" can mean a monovalent antigen-binding fragment of a human monoclonal antibody that is larger than a Fab fragment. For example, a Fab' fragment includes all of the light chain, all of the variable region of the heavy chain, and all or part of the first and second constant domains of the heavy chain. For example, a Fab' fragment can additionally include some or all of amino acid residues 220 to 330 of the heavy chain.

The term "F(ab')2 fragment" can mean a bivalent antigen-binding fragment of a human monoclonal antibody. An F(ab')2 fragment includes, for example, all or part of the variable regions of two heavy chains-and two light chains, and can further include all or part of the first constant domains of two heavy chains and two light chains.

The term "single chain Fv (scFv)" can mean a fusion of the variable regions of the heavy (VH) and light chains (VL) connected with a short linker peptide.

The term "bispecific antibody (BsAb)" can mean a bispecific antibody comprising two scFv linked to each other by a shorter linked peptide.

One skilled in the art knows that the exact boundaries of a fragment of an antibody are not important, so long as the fragment maintains a functional activity. Using well-known recombinant methods, one skilled in the art can engineer a polynucleotide sequence to express a functional fragment with any endpoints desired for a particular application. A functional fragment of the antibody may comprise or consist of a fragment with substantially the same heavy and light chain variable regions as the human antibody.

Preferably, the antigen-binding fragment thereof, with respect to the first aspect of the invention, is ZIP12-specific or immunospecific for an epitope within ZIP12. The antigen-binding fragment thereof may comprise or consist of any of the fragments selected from a group consisting of VH, VL, Fd, Fv, Fab, Fab', scFv, F(ab')2 and Fc fragment.

The antigen-binding fragment thereof may comprise or consist of any one of the antigen binding region sequences of the VL, any one of the antigen binding region sequences of the VH, or a combination of VL and VH antigen binding regions of a human antibody. The appropriate number and combination of VH and VL antigen binding region sequences may be determined by those skilled in the art depending on the desired affinity and specificity and the intended use of the antigen-binding fragment. Functional fragments or antigen-binding fragments of antibodies may be readily produced and isolated using methods well known to those skilled in the art. Such methods include, for example, proteolytic methods, recombinant methods and chemical synthesis. Proteolytic methods for the isolation of functional fragments comprise using human antibodies as a starting material. Enzymes suitable for proteolysis of human immunoglobulins may include, for example, papain, and pepsin. The appropriate enzyme may be readily chosen by one skilled in the art, depending on, for example, whether monovalent or bivalent fragments are required. For example, papain cleavage results in two monovalent Fab' fragments that bind antigen and an Fc fragment. Pepsin cleavage, for example, results in a bivalent F(ab') fragment. An F (ab')2 fragment of the invention may be further 5 reduced using, for example, DTT or 2-mercaptoethanol to produce two monovalent Fab' fragments.

Functional or antigen-binding fragments of antibodies produced by proteolysis may be purified by affinity and column chromatographic procedures. For example, undigested antibodies and Fc fragments may be removed by binding to protein A. Additionally, functional fragments may be purified by virtue of their charge and size, using, for example, ion exchange and gel filtration chromatography. Such methods are well known to those skilled in the art.

The antibody or antigen-binding fragment thereof may be produced by recombinant methodology. Preferably, one initially isolates a polynucleotide encoding desired regions of the antibody heavy and light chains. Such regions may include, for example, all or part of the variable region of the heavy and light chains. Preferably, such regions can particularly include the antigen binding regions of the heavy and light chains, preferably the antigen binding sites, most preferably the CDRs.

The polynucleotide encoding the antibody or antigen-binding fragment thereof according to the invention may be produced using methods known to those skilled in the art. The polynucleotide encoding the antibody or antigen-binding fragment thereof may be directly synthesized by methods of oligonucleotide synthesis known in the art. Alternatively, smaller fragments may be synthesized and joined to form a larger functional fragment using recombinant methods known in the art.

As used herein, the term "immunospecificity" can mean the binding region is capable of immunoreacting with ZIP12, or a variant or fragment thereof, by specifically binding therewith. The antibody or antigen-binding fragment thereof can selectively interact with an antigen (e.g. ZIP12 or a variant or fragment thereof) with an affinity constant of approximately 10-5 to 10-13 M-1, preferably 10-6 to 10-9 M-1, even more preferably, 10-10 to 10-12 M-1.

In another aspect, a method of treating or preventing pulmonary hypertension in humans and non-human animals by suppressing intracellular free zinc is provided. This aspect of the invention arises from the inventors' novel finding that disruption of a zinc transporter can attenuate pulmonary hypertension, and their data indicating a mechanism involving reduced intracellular labile zinc levels. Methods of suppressing intracellular free zinc include, but are not limited to, treatment with zinc chelators such as TPEN and DTPA.

As will be expanded upon in the Examples, the invention can be reasonable expected to work across many species, as ZIP12 is highly conserved. The Examples specifically validate the invention in rats, humans, and cattle.

The invention is not limited to pulmonary hypertension caused by a low oxygen environment. In the Examples the inventors demonstrate that the invention is applicable to, but not limited to, pulmonary hypertension caused by hemoglobinopathies, idiopathic pulmonary arterial hypertension, and pulmonary hypertension accompanying other diseases such as congenital heart disease and chronic obstructive airways disease. Due to the interrelationship between the accompanying diseases and pulmonary hypertension, the current invention can be used for the treatment or prevention of accompanying conditions or associated pathology. In a particular embodiment, the pulmonary hypertension to be prevented, diagnosed or treated is caused by chronic hypoxic stress.

In another aspect, the invention provides a kit for screening molecules for use in the treatment or prevention of pulmonary hypertension, wherein the molecules are capable of altering the biological activity or levels of ZIP12, the kit comprising means for contacting test molecule with one or more cells expressing ZIP12. A kit can further comprise instructions for use of the molecule or composition.

"Inhibiting" as used herein can mean reducing the normal level of gene expression or protein activity by any amount. For example, the inhibitor may be an agent capable of reducing the level of gene expression or protein activity by up to 1, 5, 10, 15, 20, 25, 30, 35, 40, 45, 50, 55, 60, 65, 70, 75, 80, 85, 90, 95 or 100%.

"Treating" or "treatment" as used herein includes both preventing and ameliorating or attenuating the symptoms of a disease, disorder or condition. Methods of prophylaxis and any and all methods that treat, reduce or help alleviate symptoms associated with said disease, disorder or condition are therefore expressly included.

A "test molecule" is a potential agent for the treatment of pulmonary hypertension, where the ability to modulate ZIP12 is unknown.

A "model" is an experimental system designed to allow properties or effects of molecules to be ascertained, and wherein said properties or effects are applicable more broadly. For instance a model allows a molecule's in vivo effects on humans to be indirectly ascertained.

A "zinc probe" allows the concentration of intracellular labile zinc to be measured. Examples are given below.

A "ZIP12 reporter vector" is a system whereby the expression of ZIP12 can be easily ascertained, for instance by linking expression of ZIP12 to luciferase. Examples are given below.

A "low oxygen environment" is an environment wherein the concentration of oxygen is significantly lower than the atmospheric concentration of oxygen at sea level.

The molecules of the invention may be administered to the subject to be treated on their own or in combination with other active ingredients. They may be administered in a pharmaceutically acceptable vehicle. The molecules identified according to the method of the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given.

Medicaments comprising agents of the invention may be used in a number of ways. For instance, oral administration may be required, in which case the agents may be contained within a composition that may, for example, be ingested orally in the form of a tablet, capsule or liquid. Compositions comprising agents of the invention may be administered by inhalation (e.g. intranasally). Compositions may also be formulated for topical use. For instance, creams or ointments may be applied to the skin.

Agents according to the invention may also be incorporated within a slow- or delayed release device. Such devices may, for example, be inserted on or under the skin, and the medicament may be released over weeks or even months. The device may be located at least adjacent the treatment site. Such devices may be particularly advantageous when long-term treatment with agents used according to the invention is required and which would normally require frequent administration (e.g. at least daily injection).

Agents and medicaments according to the invention may be administered to a subject by injection into the blood stream or directly into a site requiring treatment. Injections may be intravenous (bolus or infusion) or subcutaneous (bolus or infusion), or intradermal (bolus or infusion).

It will be appreciated that the amount of the agent or medicament that is required is determined by its biological activity and bioavailability, which in turn depends on the mode of administration, the physiochemical properties of the agent, vaccine and medicament, and whether it is being used as a monotherapy or in a combined therapy. The frequency of administration will also be influenced by the half-life of the agent within the subject being treated. Optimal dosages to be administered may be determined by those skilled in the art, and will vary with the particular agent in use, the strength of the pharmaceutical composition, the mode of administration, and the advancement of the disease, disorder or condition. Additional factors depending on the particular subject being treated will result in a need to adjust dosages, including subject age, weight, gender, diet, and time of administration.

Generally, a daily dose of between 0.001 µg/kg of body weight and 10 mg/kg of body weight of agent or medicament according to the invention may be used for treating a disease, disorder or condition, depending upon which agent or medicament is used. More preferably, the daily dose is between 0.01 µg/kg of body weight and 1 mg/kg of body weight, more preferably between 0.1 µg/kg and 100 µg/kg body weight, and most preferably between approximately 0.1 µg/kg and 10 µg/kg body weight.

The agent or medicament may be administered before, during or after onset of the disease, disorder or condition. Daily doses may be given as a single administration (e.g. a single daily injection). Alternatively, the agent or medicament may require administration twice or more times during a day. As an example, agents and medicaments may be administered as two (or more depending upon the severity of the disease, disorder or condition being treated) daily doses of between 0.07 µg and 700 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of agents, vaccines and medicaments according to the invention to a patient without the need to administer repeated doses. Known procedures, such as those conventionally employed by the pharmaceutical industry (e.g. in vivo experimentation, clinical trials, etc.), may be used to form specific formulations of the agents and medicaments according to the invention and precise therapeutic regimes (such as daily doses of the agents and the frequency of administration).

A "subject" may be a vertebrate, mammal, or domestic animal. Hence, medicaments according to the invention may be used to treat any mammal, for example livestock (e.g. a cow), pets, or may be used in other veterinary applications. Most preferably, the subject is a human being.

A "therapeutically effective amount" of agent is any amount which, when administered to a subject, is the amount of drug that is needed to treat the disease, disorder or condition, or produce the desired effect. For example, the therapeutically effective amount of agent used may be from about 0.001 ng to about 1 mg, and preferably from about 0.01 ng to about 100 ng. It is preferred that the amount of agent is an amount from about 0.1 ng to about 10 ng, and most preferably from about 0.5 ng to about 5 ng.

A "pharmaceutically acceptable vehicle" as referred to herein, is any known compound or combination of known compounds that are known to those skilled in the art to be useful in formulating pharmaceutical compositions.

In one embodiment of the invention, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet disintegrating agents. The vehicle may also be an encapsulating material. In powders, the vehicle is a finely divided solid that is in admixture with the finely divided active agents according to the invention. In tablets, the active agent may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The active agent according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The agent may be prepared as a sterile solid composition that may be dissolved or suspended at the time of administration using sterile water, saline, or other appropriate sterile injectable medium.

The agents and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate (oleate esters of sorbitol and its anhydrides copolymerized with ethylene oxide) and the like. The agents used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions It will be appreciated that administration, into a subject to be treated, of an agent or medicament according to the invention will result in the inhibition of Slc39a12 gene expression or ZIP12 protein activity, and that this inhibition will aid in treating or preventing a disorder such as pulmonary hypertension.

Figure 1B:
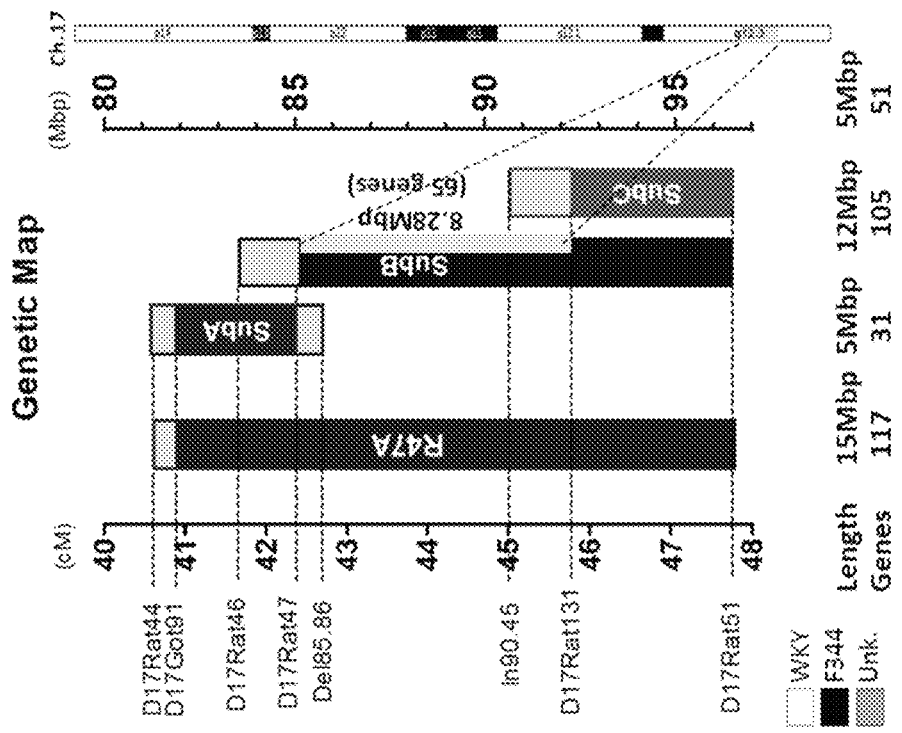
Figure 1A:
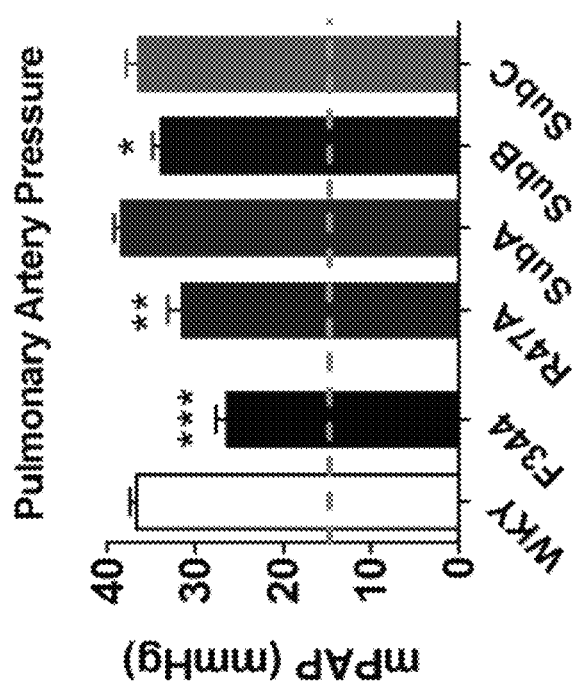
Figure 1C:
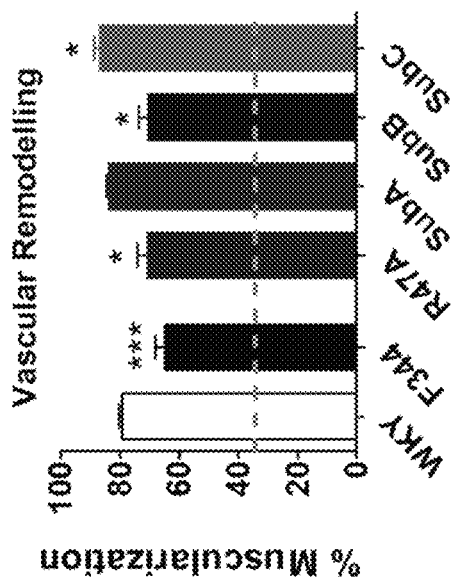
Figure 1D:
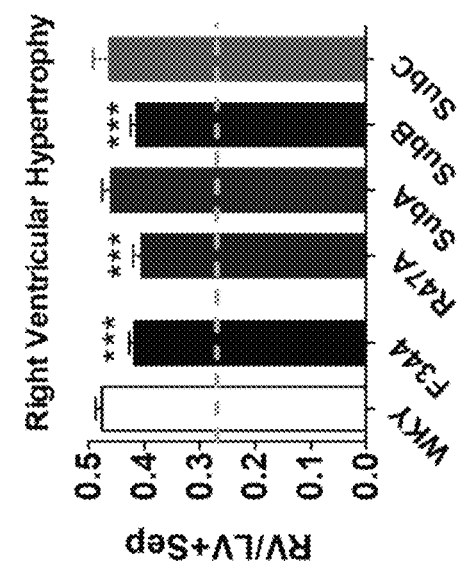
Figure 1E:
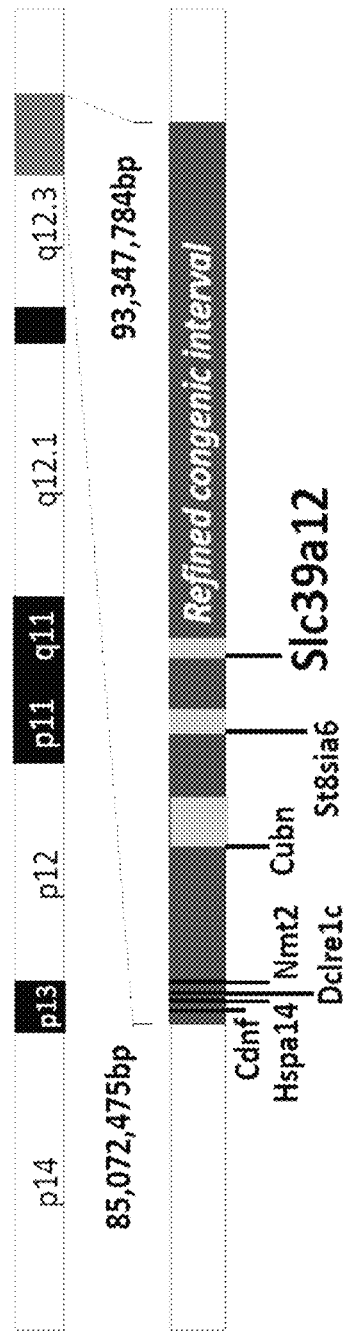

For a better understanding of the invention, and to show how embodiments of the same may be carried into effect, reference will now be made, by way of example, to the accompanying diagrammatic drawings, in which:

FIG. 1A-1E. The pulmonary vascular response to hypoxia in the F344 rat is influenced by a region of chromosome 17 containing Slc39a12. FIG. 1A. A genetic map of 3 subcongenic strains (SubA, SubB and SubC) derived from the R47A congenic strain (originally derived from a WKYxF344 cross) backcrossed with the WKY parental strain. The refined congenic region (orange) of 8.28 Mb containing 65 genes is within the SubB strain. FIG. 1B-1D. SubB exhibits attenuated pulmonary hypertension after 2 weeks exposure to a 10% O2 atmosphere compared to WKY, SubA and SubC rats: b. mean pulmonary artery pressure (mPAP); c. right ventricular hypertrophy (RV/LV+Septum ratio) (n=17 WKY, 15 F344, 14 R47A, 8 SubA, 10 SubB, 10 SubC); 1D. vascular muscularisation (n=6 each group). Dotted line indicates mean measurements from all the rats in a normal oxygen atmosphere (21% O2; mPAP=14.7±0.3 mmHg; RVH=0.270±0.04; % muscularization=34.2±0.36; for actual values in rat strains see FIG. 8). Values are expressed as mean±standard error of the mean (SEM). *P<0.05, P<0.01, *P<0.001 compared to WKY after one-way ANOVA analysis followed by Bonferroni correction for multiple testing. FIG. 1E. The genes of interest (Slc39a12, St8sia6, Cubn, Nmt2, Dclre1c, Hspa14 and Cdnf) identified within the SubB congenic interval. The frameshift mutation in Slc39a12 introduces a stop-codon, resulting in a truncated protein.

Figure 2D:
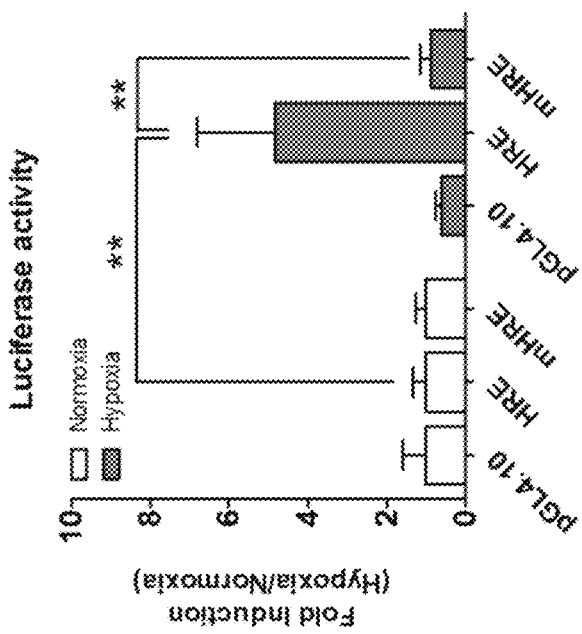
Figure 2E:
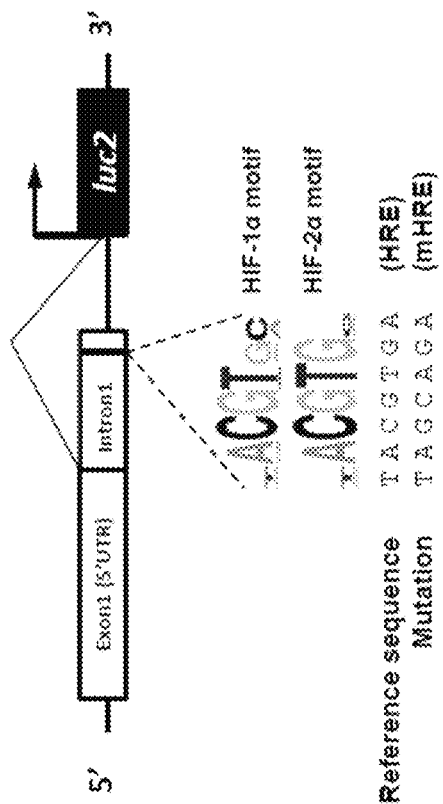
Figure 2F:
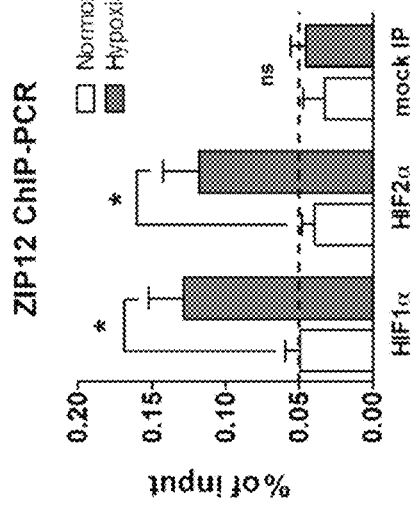

FIG. 2A-2F. Slc39a12 encodes a zinc transporter. ZIP12, which is up-regulated in pulmonary vascular tissue from mammals exposed to chronic hypoxia. FIG. 2A. ZIP12 mRNA levels in control and hypoxic WKY rat lungs. FIG. 2B. Prominent ZIP12 immunostaining in remodeled pulmonary arterioles in WKY but not F344 rat lungs exposed to hypoxia. FIG. 2C. No ZIP12 staining was detected in pulmonary arteries of low altitude (normoxia control, CO calf) calves and sea-level humans, yet prominent ZIP12 immunostaining was observed in the remodeled pulmonary arteries of calves with severe pulmonary hypertension (Hx calf), in cattle naturally susceptible to pulmonary hypertension at altitude ("Brisket disease", BD), as well as Kyrgyz highlanders residing above 2500 m. FIG. 2D. Design of the luciferase reporter vector PGL4.10 containing a 5' region of ZIP12 which includes a hypoxia response element (HRE) encoding for both HIF-1α and HIF-2α binding motifs or a mutant HRE sequence where the 5'-ACGTG-3' motif has been replaced by 5'-AGCAG-3'(mHRE). FIG. 2E. Human pulmonary artery smooth muscle cells (HPASMCs) transfected with the ZIP12 HRE reporter vector demonstrated a significantly increased luciferase activity after exposure to hypoxia, but not in the cells transfected with the mutant HRE vector (n=6 per group, replicated twice). FIG. 2F. Increased levels of HIF-1α and HIF-2α bound to the ZIP12 HRE assayed by ChIP-qPCR of chromatin from HPASMCs cultured in normoxia and hypoxic conditions (n=3 per group, replicated twice). Data are calculated as percentage of input levels, with the dotted line marking percentages below mock immunoprecipitation (mock IP). Values are expressed as mean±SEM. *P<0.05, P<0.01, *P<0.001 compared to normoxic control after One-Way ANOVA analysis followed by Bonferroni correction for multiple testing. NS, not significant.

Figure 3C:
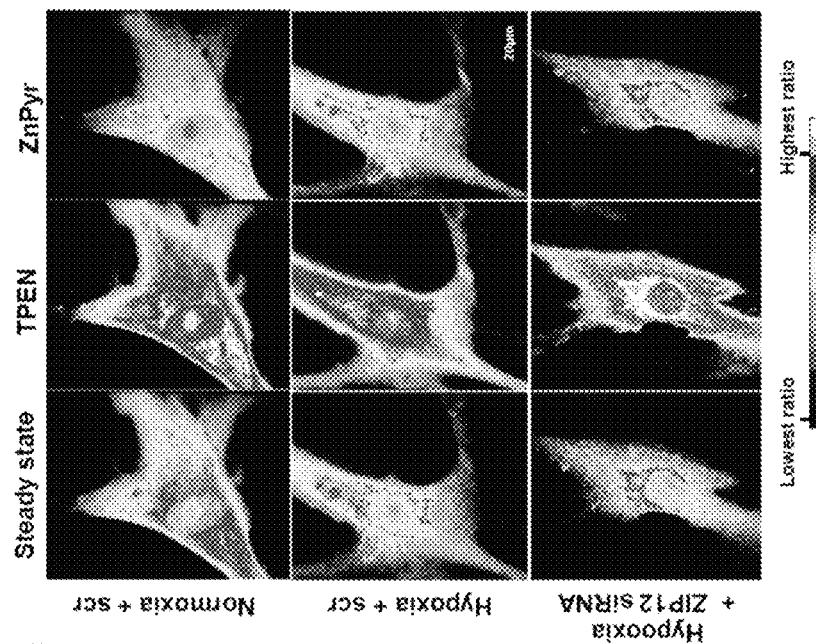
Figure 3A:
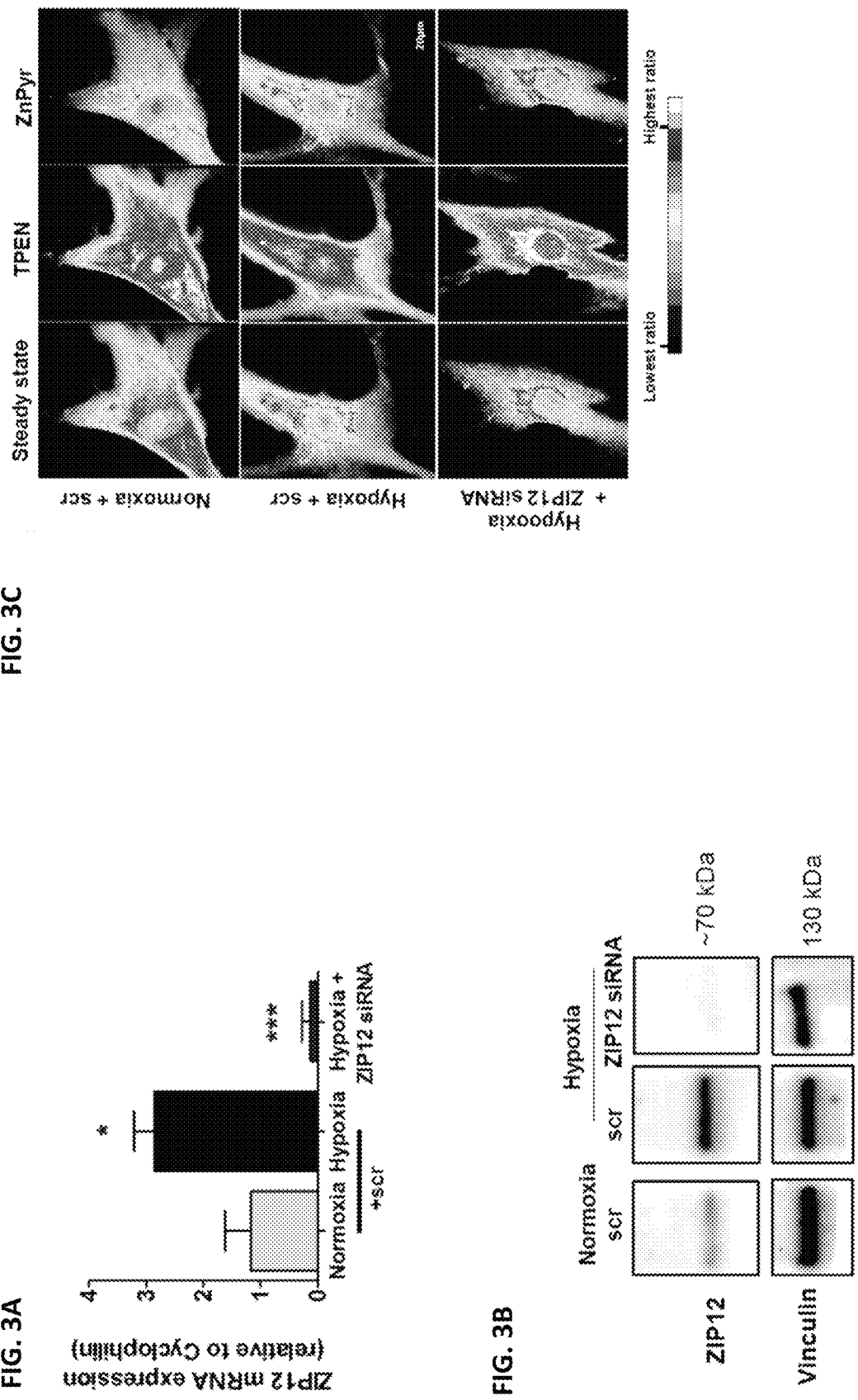
Figure 3B:
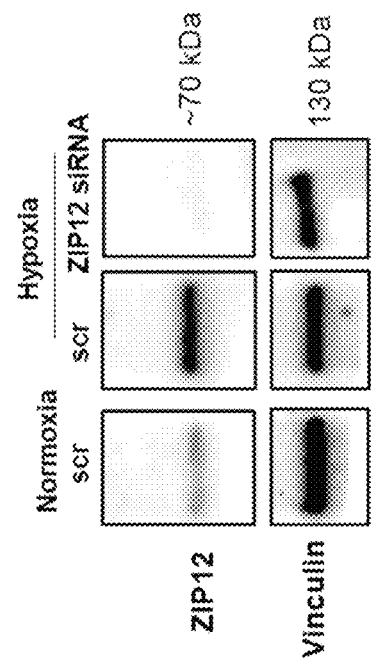
Figure 3E:
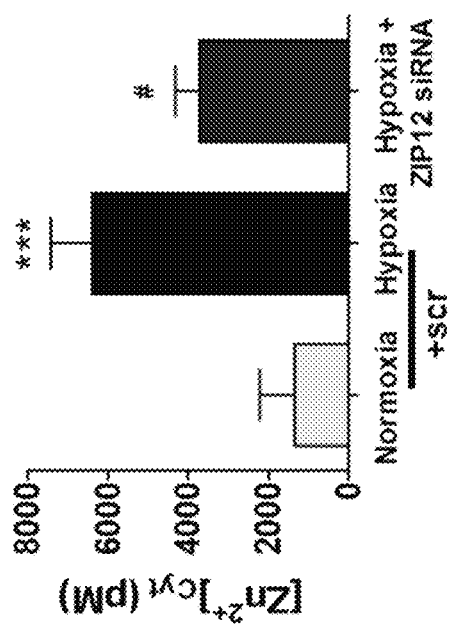
Figure 3D:
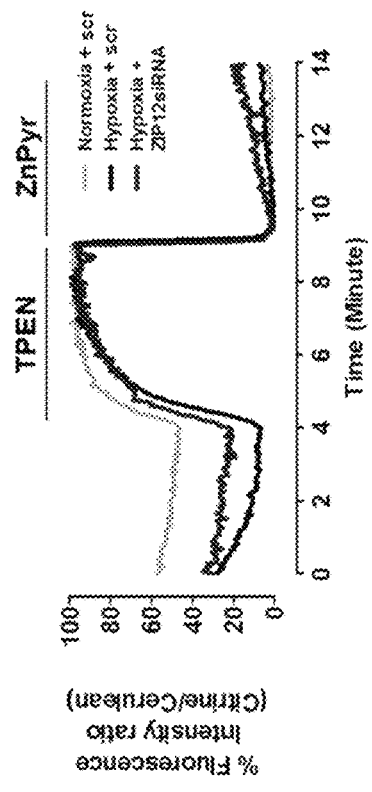
Figure 3F:
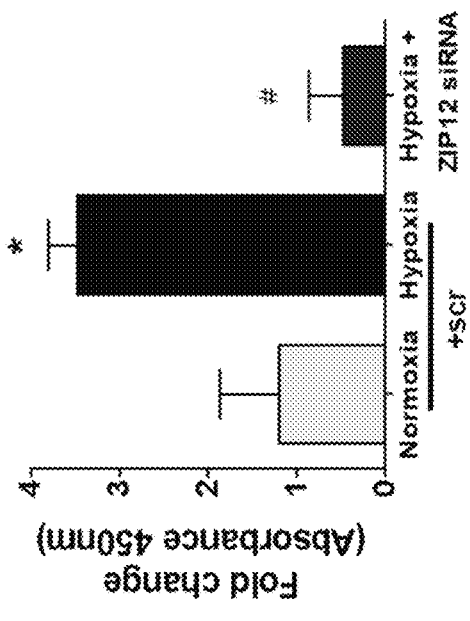

FIG. 3A-3F. ZIP12 knockdown inhibits hypoxia-induced increase in intracellular labile zinc concentration and proliferation of human pulmonary artery smooth muscle cells (HPASMCs). FIG. 3A. Chronic hypoxia (48 h) increases ZIP12 mRNA levels in HPASMCs, which is inhibited by Slc39a12 siRNA (n=5 each group). FIG. 3B. Representative immunoblot of ZIP12 demonstrating inhibition of hypoxia-stimulated ZIP12 protein expression by Slc39a12 siRNA in HPASMCs (n=3). FIG. 3C. Representative wide-field microscope images of HPASMC transfected with eCALWY-4 probe. Hypoxia exposure produced a striking increase in intracellular free zinc (resulting in decreased FRET) (VINKENBORG, J. L. et al. Genetically encoded FRET sensors to monitor intracellular Zn2+ homeostasis. Nature methods 6, 737-740, doi:10.1038/nmeth.1368, 2009). This was inhibited by transfection with ZIP12 siRNA. TPEN-mediated Zn2+ chelation was used to derive maximum fluorescence and 100 μM ZnCl2 in the presence of the Zn2+ ionophore and pyrithione (ZnPyr) was used to derive the minimum fluorescence. FIG. 3D. Representative traces showing the changes in fluorescence ratio of the eCALWY-4 probe. Steady-state fluorescence intensity ratio citrine/cerulean (R) was measured, then maximum and minimum ratios were determined to calculate free Zn2+ concentration using the formula: [Zn2+]=Kd×(Rmax−R)/(R−Rmin), where the Kd for eCALWY-4 is 630 pM, the maximum ratio (Rmax) was obtained upon intracellular zinc chelation with 50 μM TPEN and the minimum ratio (Rmin) was obtained upon zinc saturation with 100 μM ZnCl2 in the presence of the Zn2+ ionophore, pyrithione (5 μM) ((VINKENBORG, J. L. et al. Genetically encoded FRET sensors to monitor intracellular Zn2+ homeostasis. Nature methods 6, 737-740, doi:10.1038/nmeth.1368, 2009). FIG. 3E. Quantification of intracellular zinc levels (n=10 each group). ***P<0.001 compared to control group, #P<0.05 compared to hypoxia group. FIG. 3F. ZIP12 siRNA inhibits hypoxia-induced proliferation in HPASMCs. Scr, scramble siRNA control.

Figure 4A:
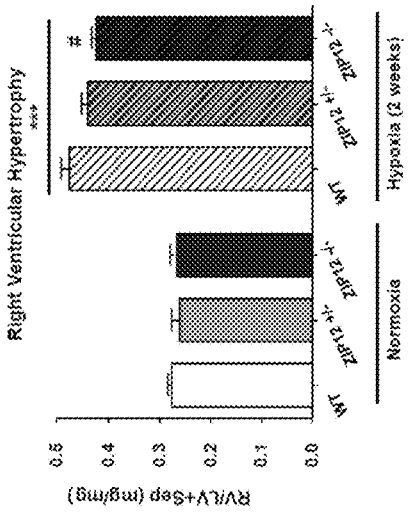
Figure 4B:
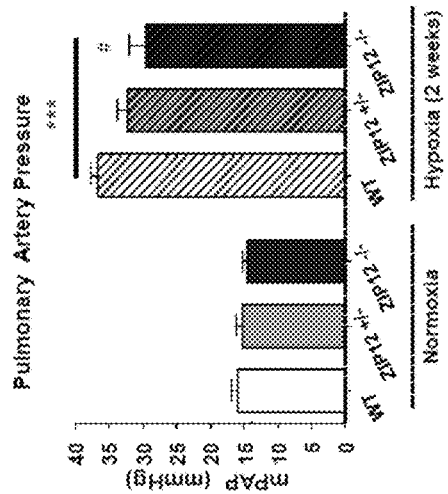
Figure 4D:
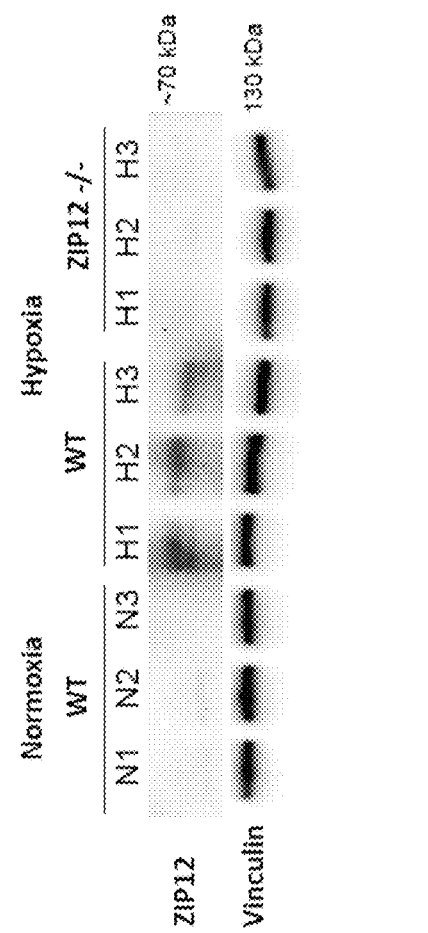
Figure 4C:
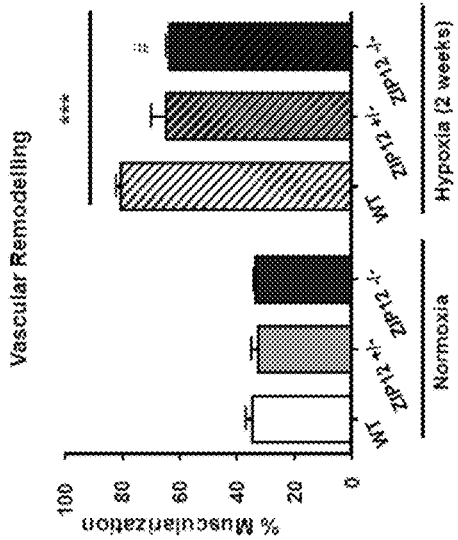
Figure 4E:
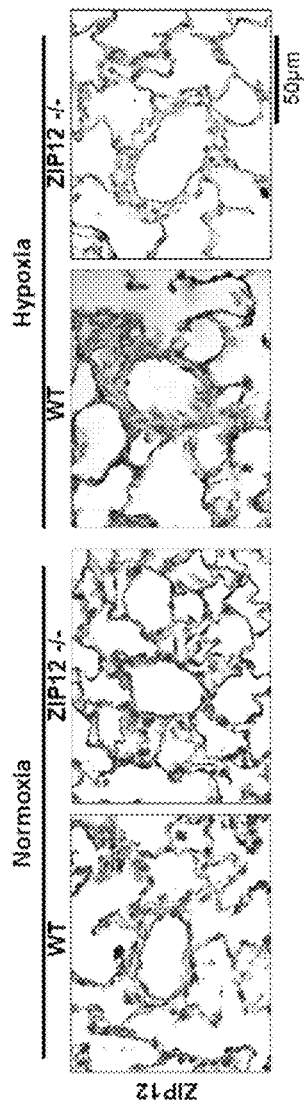
Figure 4F:
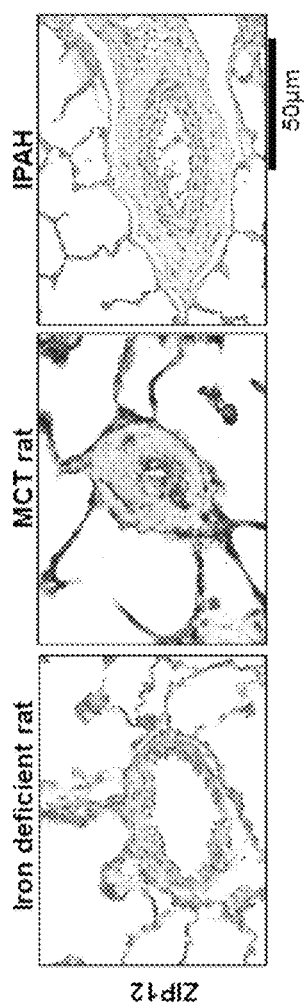
Figure 4G:
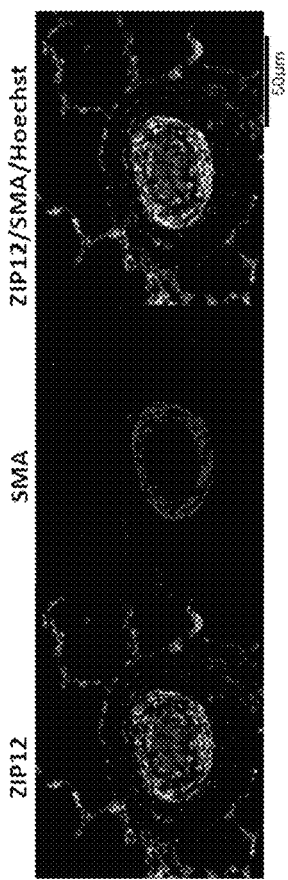

FIG. 4A-4G. Genetic disruption of ZIP12 in WKY rat attenuates hypoxia-induced pulmonary hypertension, a-c. Zinc finger nucleases were used to disrupt ZIP12 in the WKY strain. Rats deficient in ZIP12 demonstrate allele dose-dependent attenuation of hypoxia induced pulmonary hypertension compared to wild-type (WT) rats: FIG. 4A. mean pulmonary artery pressure (mPAP); FIG. 4B. right ventricular hypertrophy (RV/LV+Septum) (normoxia groups: n=10 WT, 8 ZIP12+/−, 12 ZIP12−/−; hypoxia groups: n=14 WT, 16 ZIP12+/−, 12 ZIP12−/−); FIG. 4C. pulmonary arteriole muscularisation (n=5 each group). ***p<0.001 compared to normoxia WT group, #p<0.05 compared to hypoxia WT group after one-way ANOVA analysts followed by Bonferroni correction for multiple testing. FIG. 4D. ZIP12 was undetectable by Western blot in hypoxic ZIP12−/− rats but increased in hypoxic wide-type (WKY) rats (n=3 each group). FIG. 4E. ZIP12 expression by immunohistochemistry of WT and ZIP12−/− rat lungs before and after hypoxia (2 weeks). FIG. 4F. ZIP12 expression in lungs from a chronic iron deficient rat, monocrotaline (MCT) rat and a patient with idiopathic pulmonary arterial hypertension (IPAH). FIG. 4G. Double immunofluorescence demonstrates co-localisation of ZIP12 and smooth muscle actin in the remodeled vessels from the IPAH patient.

FIG. 5A-5F. Pulmonary arterial smooth muscle cells with FIG. 5A) ZIP12 overexpression demonstrated, FIG. 5B) increased intracellular zinc levels, FIG. 5C) increased proliferation, FIG. 5D) increased oxygen consumption (OCR), FIG. 5E) mitochondrial membrane hyperpolarization, and FIG. 5F) increased ROS production.

Figure 6:
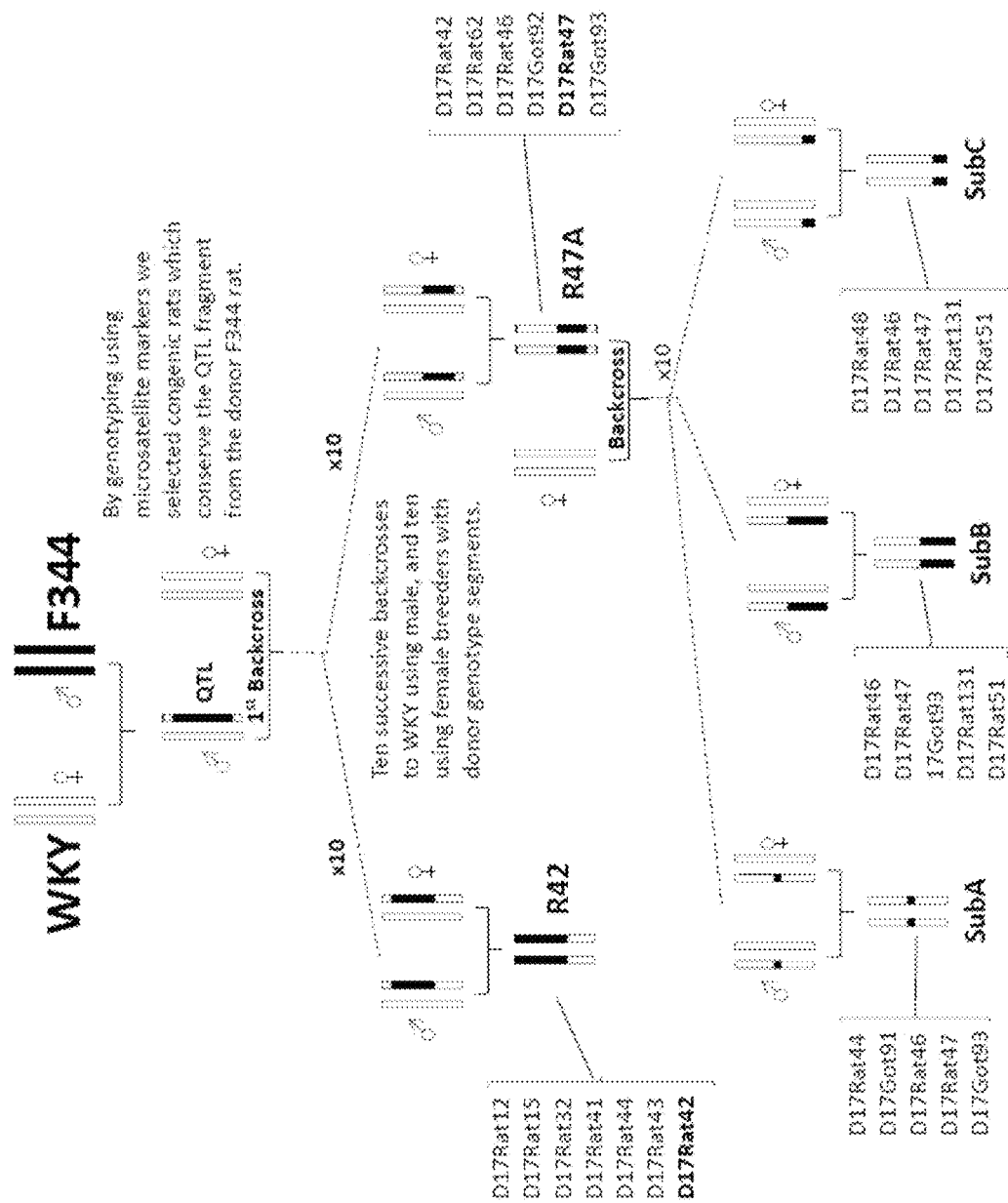

FIG. 6. Generation of congenic and sub-congenic strains. Congenic rat lines were produced by introgression of the F344 chromosome 17 QTL segment onto the WKY genetic background by repeated backcrossing. Congenic rat strain R47A (WKY.F344-D17Got91/D17Rat51) contains 15 Mbp from the F344 donor region that maps to the distal end of the QTL on a WKY background. Three sub-congenic strains, SubA (WKY.F344-D17Got91/D17Rat47), SubB (WKY.F344-D17Rat47/D17Rat51) and SubC (WKY.F344-D17Rat131/D17Rat51), were produced containing separate fragments of the R47A donor region by backcrossing of (R47A x WKY) F1 with WKY parental rats. Three recombination events within the R47A congenic interval break the congenic interval into three smaller and overlapping sub-congenic intervals (FIG. 1, main text).

Figure 7B:
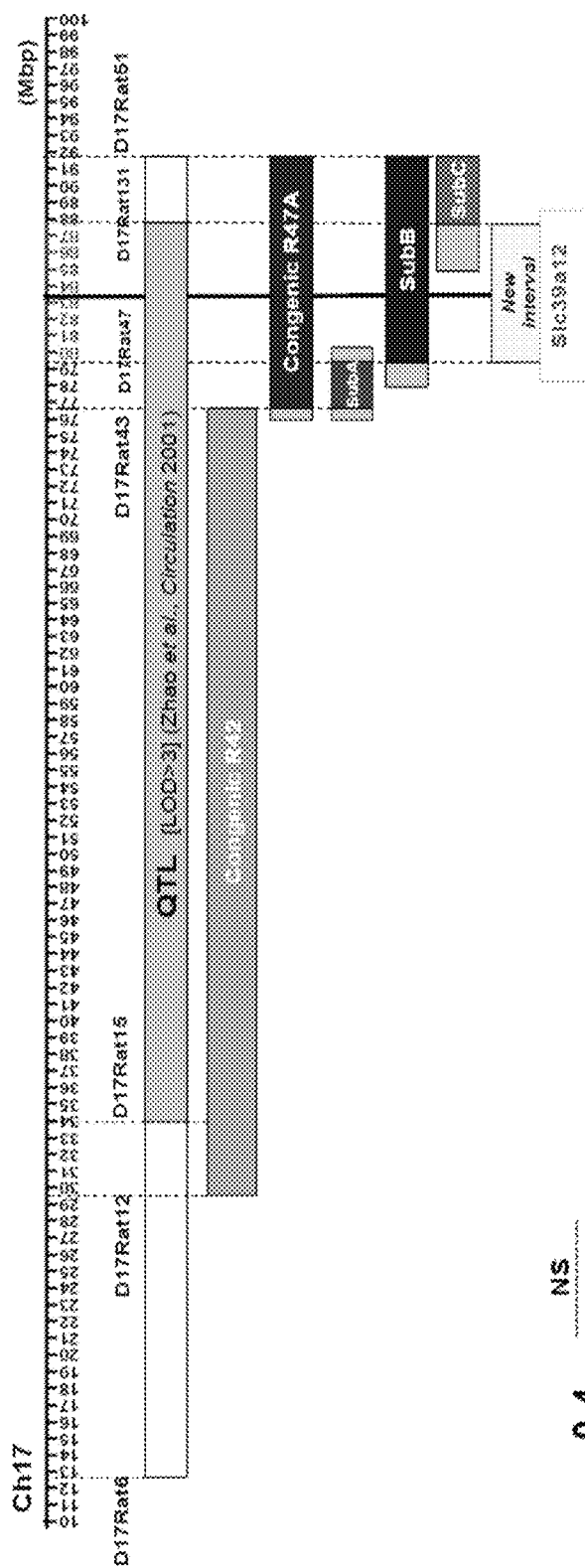
Figure 7A:
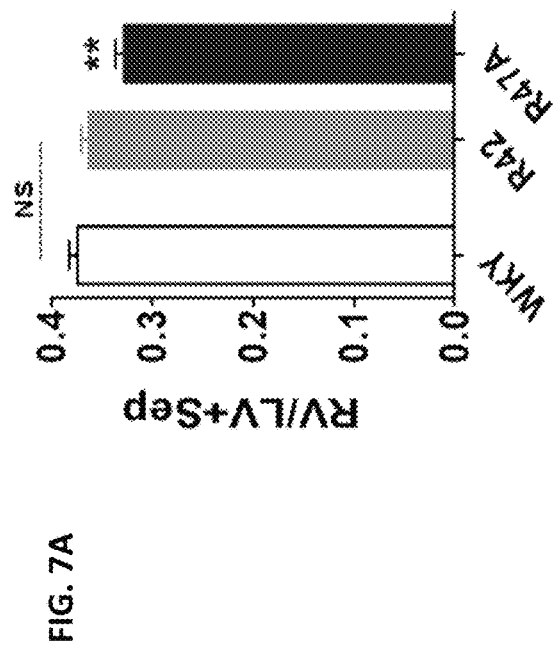

FIG. 7A-7B. Dissection of QTL. FIG. 7A. The hypoxia-resistant F344 phenotype tracks with the congenic R47A line. Rats were kept in 10% O2 for 2 weeks and right ventricular hypertrophy (RV/LV+Sep) was significantly attenuated in the congenic R47A strain (0.32±0.03, n=13, **P<0.01) compared to WKY rats (0.37±0.03, n=15), whereas congenic R42 rats (0.36±0.03, n=17) were similar (NS) to WKY rats. FIG. 7B. An illustrative genetic map showing the relationship of the congenic strains (R42, R47A), subcongenic strains (SubA, SubB, SubC) and Slc39a12 to the original QTL (defined by a LOD score >3; Zhao et al Circulation 2001, 103, 442-447) on a physical map of chromosome 17 (using Rat Genome Assembly V5.0).

Figure 8C:
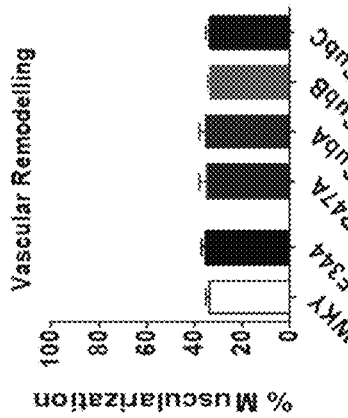
Figure 8B:
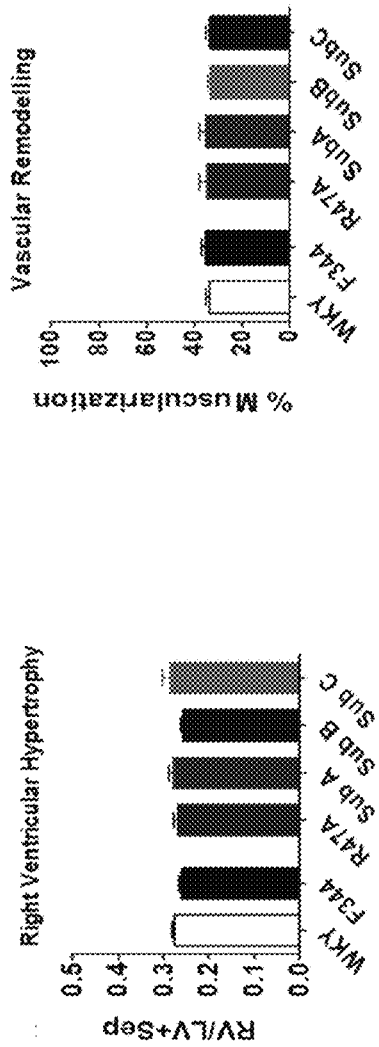
Figure 8A:
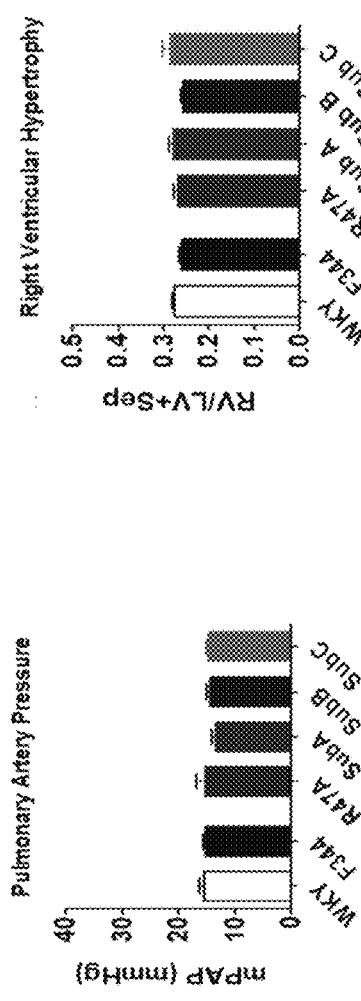
Figure 8E:
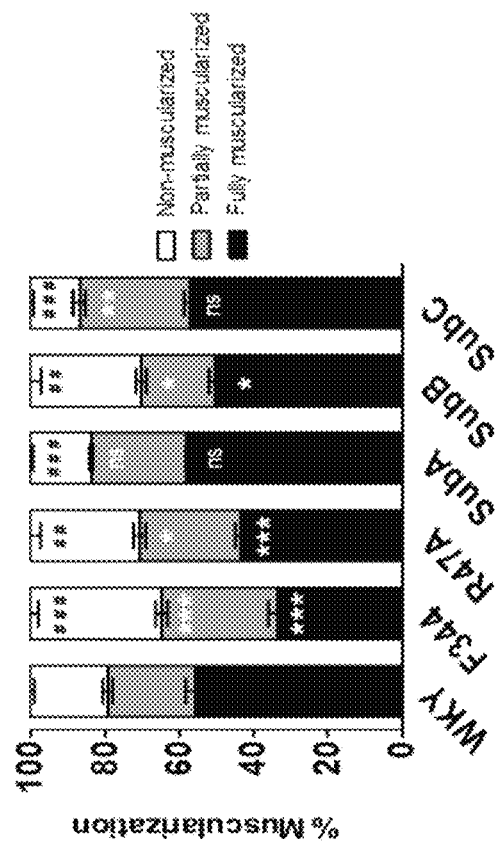
Figure 8D:
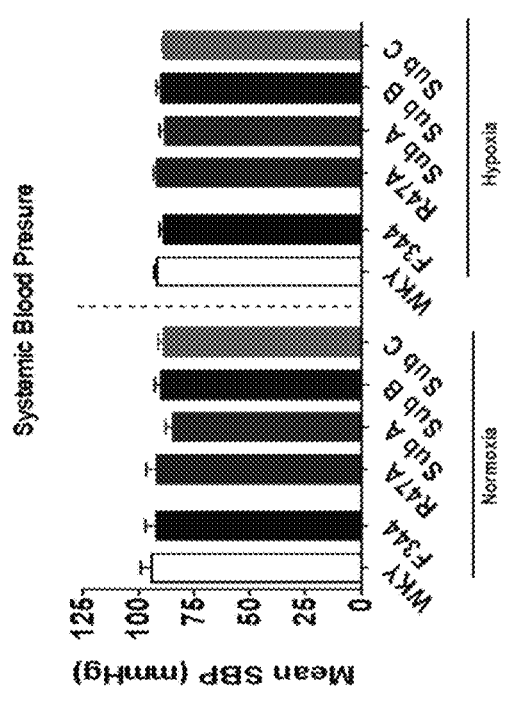

FIG. 8A-8E: Cardiovascular phenotype of rats strains. In normoxia, WKY, F344, R47A, SubA, SubB and SubC rats show no significant differences in FIG. 8A. mean pulmonary artery pressure (mPAP), FIG. 8B. right ventricular hypertrophy (RV/LV+Septum ratio) and FIG. 8C. vascular muscularisation (n=8 each group); FIG. 8D. Systemic blood pressure (SBP) is similar in all strains in both normoxia and hypoxic conditions. FIG. 8E. F344, R47A and SubB rats exhibit attenuated pulmonary vascular remodelling after 2 weeks exposure to a 10% O2 atmosphere compared to WKY, SubA and SubC rats (n=6 each group). Values are expressed as the mean±standard error of the mean (SEM). *P<0.05, P<0.01, *P<0.001 compared to WKY (% of fully muscularised and partially muscularised vessels); ##P<0.01, ###P<0.001 compared to WKY (% of non-muscularised vessels) after One-Way ANOVA analysis followed by Bonferroni correction for multiple testing.

Figure 9:
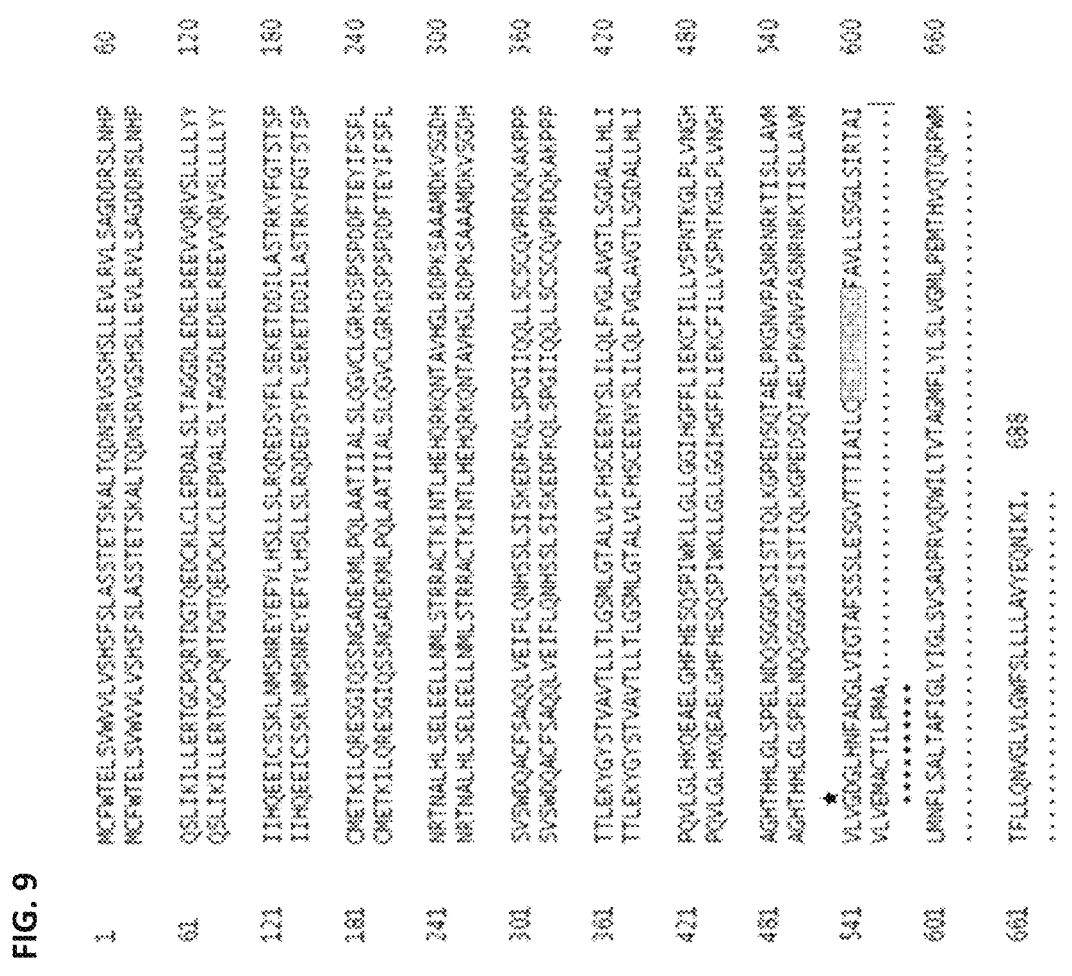

FIG. 9. ZIP12 protein sequence. Upper panel sequence shows the WKY protein sequence (688 aa) (SEQ ID NO:41) and lower panel shows the truncated F344 protein sequence (553 aa) (SEQ ID NO: 42). Stars (*) mark the mutated amino acids compared to WKY protein. Dotted line indicates the C-terminal truncated region in F344. The grey square highlights the metalloprotease motif.

Figure 10:
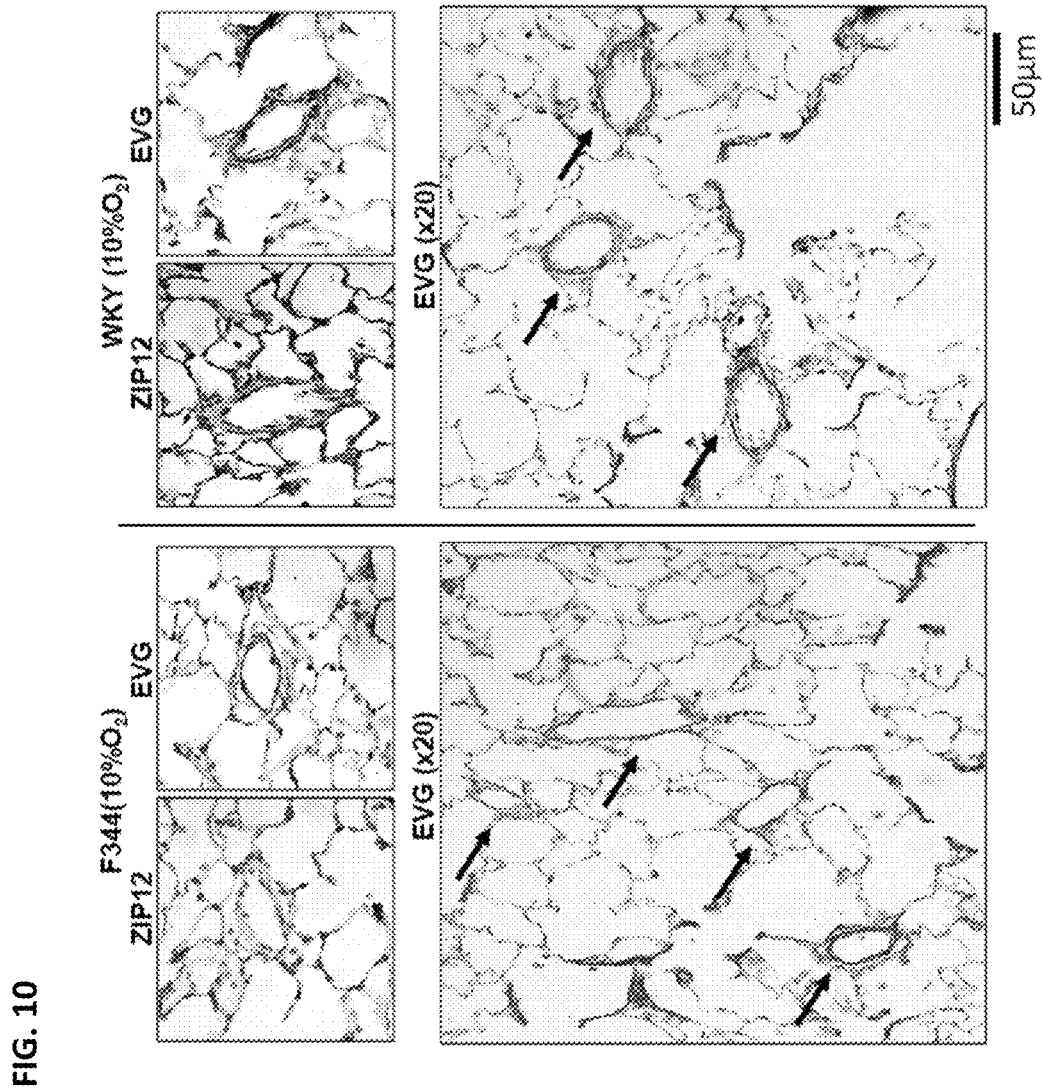

FIG. 10. The F344 is resistant to hypoxia-induced pulmonary vascular remodeling. Prominent ZIP12 immunostaining is seen in remodeled pulmonary arterioles in the chronically hypoxic WKY rat alongside vessels with a double elastic lamina (stained with Van Gieson, EVG) but not F344 lungs exposed to hypoxia. (Red arrow: vessel with double elastic lamina; blue arrow: vessel with single elastic lamina).

Figure 11A:
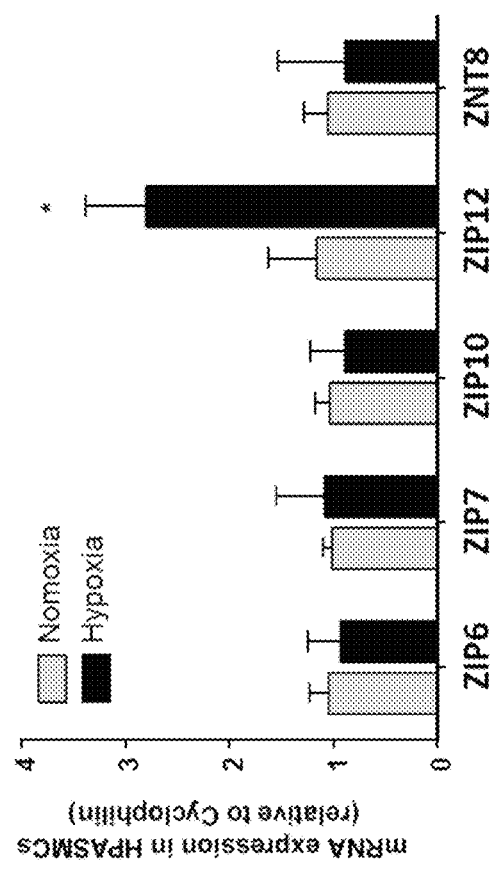
Figure 11B:
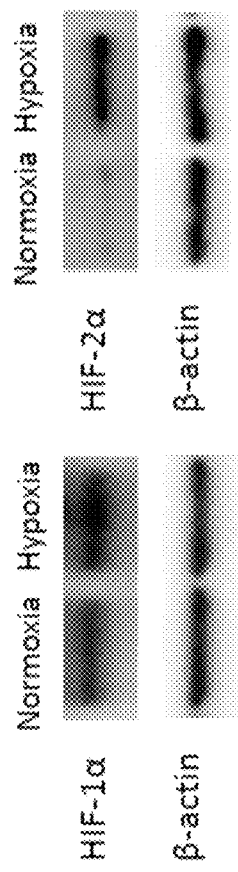

FIG. 11A-11B: ZIP12 upregulation in human pulmonary smooth muscle cells (HPASMCs) in response to hypoxia exposure. FIG. 11A. Upregulation of ZIP12 in HPASMCs exposed to hypoxia, in contrast to other zinc transporters (n=6). FIG. 11B. Representative western blots demonstrating increased HIF-2α expression in HPASMCs after 24 h hypoxia exposure.

Figure 12C:
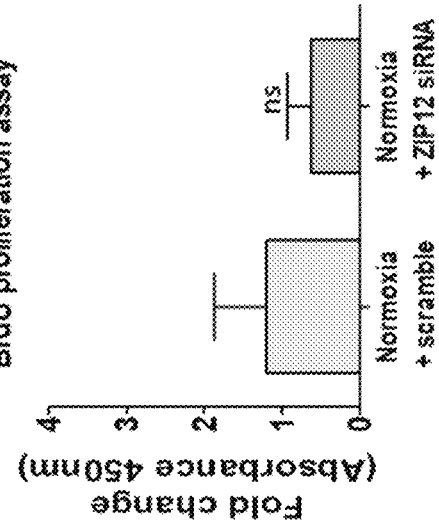
Figure 12D:
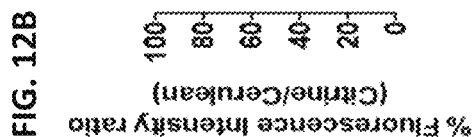
Figure 12A:
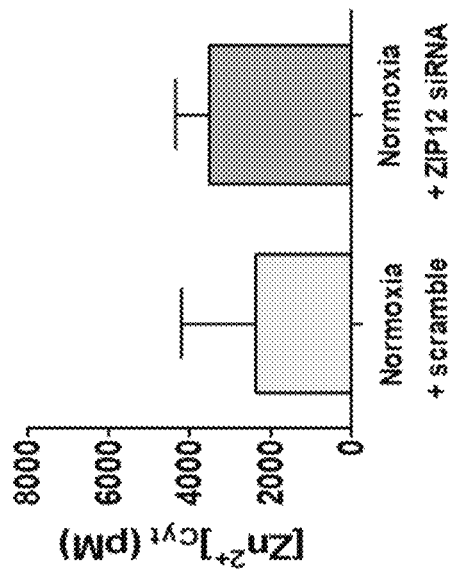
Figure 12B:
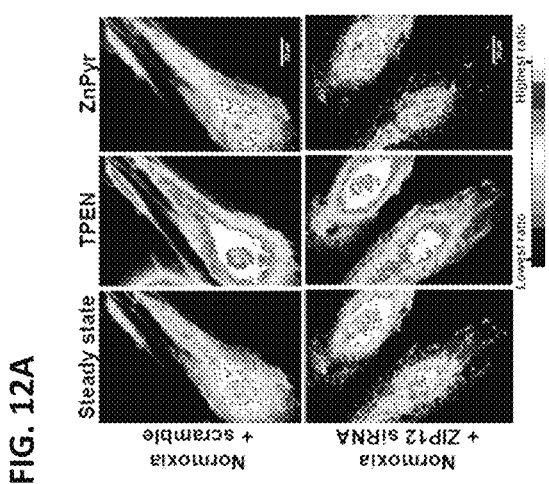

FIG. 12A-12D: ZIP12 knockdown did not affect intracellular labile zinc concentration and proliferation of human pulmonary artery smooth muscle cells (HPASMCs) in normoxic conditions. FIG. 12A. Confocal laser scanning images of HPASMC transfected with eCALWY-4 probe. Intracellular free zinc was not affected by transfection with ZIP12 siRNA in normoxia. FIG. 12B. Representative traces showing the changes in fluorescence ratio using the eCALWY-4 probe. FIG. 12C. Quantification of intracellular zinc levels (n=10). FIG. 12D. ZIP12 siRNA did not affect proliferation of HPASMCs in normoxic conditions (n=5).

Figure 13A:
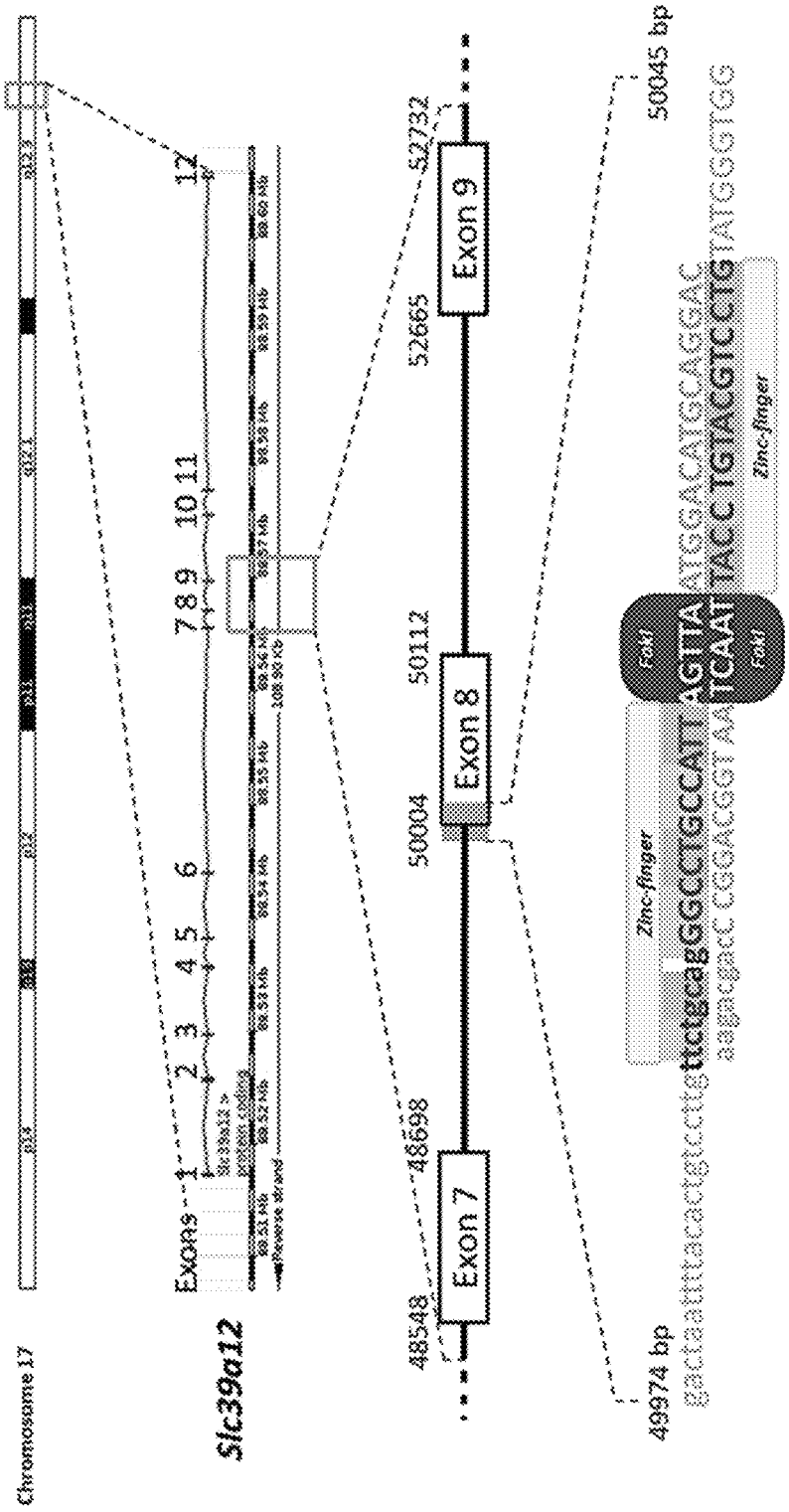
Figure 13B:
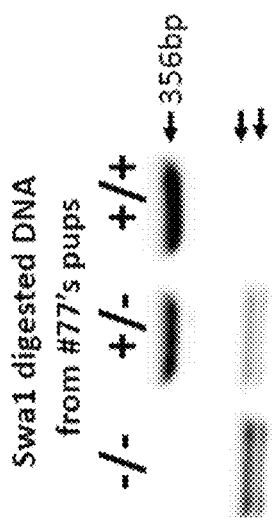
Figure 13C:
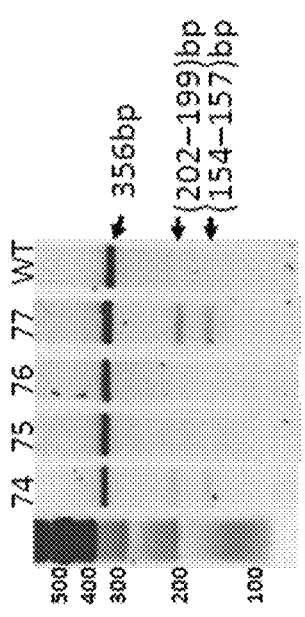
Figure 13D:
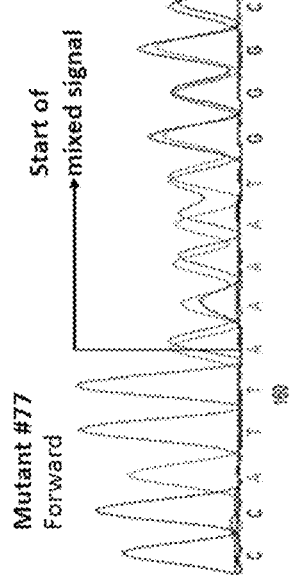
Figure 13E:
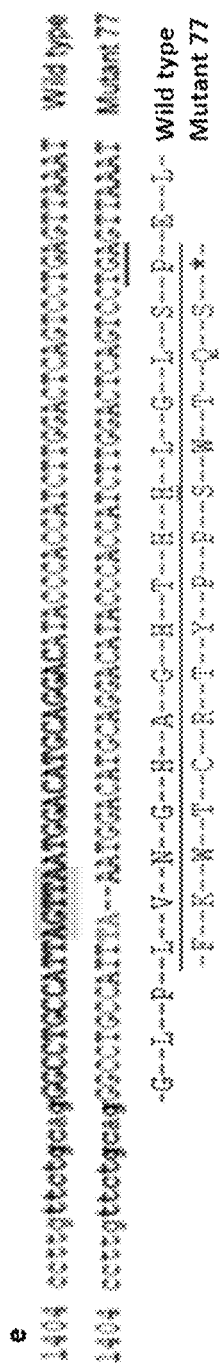

FIG. 13A-13E: Design of specific Slc39a12 ZFN and confirmation of mutant line. FIG. 13A. CompoZr™ Custom Zinc Finger Nucleases (Sigma-Aldrich) for the rat Slc39a12 gene were designed to target exon 8 (a; Sigma-Aldrich). The top sequence is SEQ ID NO: 43 and the bottom sequence is SEQ ID NO: 44. FIG. 13B-13D. Cel-I surveyor assay and gene sequencing confirmed NHEJ-induced mutations in at least one pup (mutant 77). FIG. 13E. The 4 bp (AGTT) deletion followed by 2 bp insertion (TA) into mutant 77 caused a frame-shift in coding, introducing a stop codon leading to a truncated protein. The wild type DNA sequence is SEQ ID NO: 45 and Mutant 77 DNA sequence is SEQ ID NO: 46. The wild type protein sequence is SEQ ID NO: 47 and Mutant 77 protein sequence is SEQ ID NO: 48. Red star refers to stop codon. FIG. 13E. The inventors subsequently genotyped next generation litters using SwaI (cutting point: 5'-ATTTAAAT-3'), showing 100% digestion for homozygous pups (−/−), 50% for heterozygous (+/−) and no DNA digestion for wild type rats (+/+).

Figures 14A, 14B:
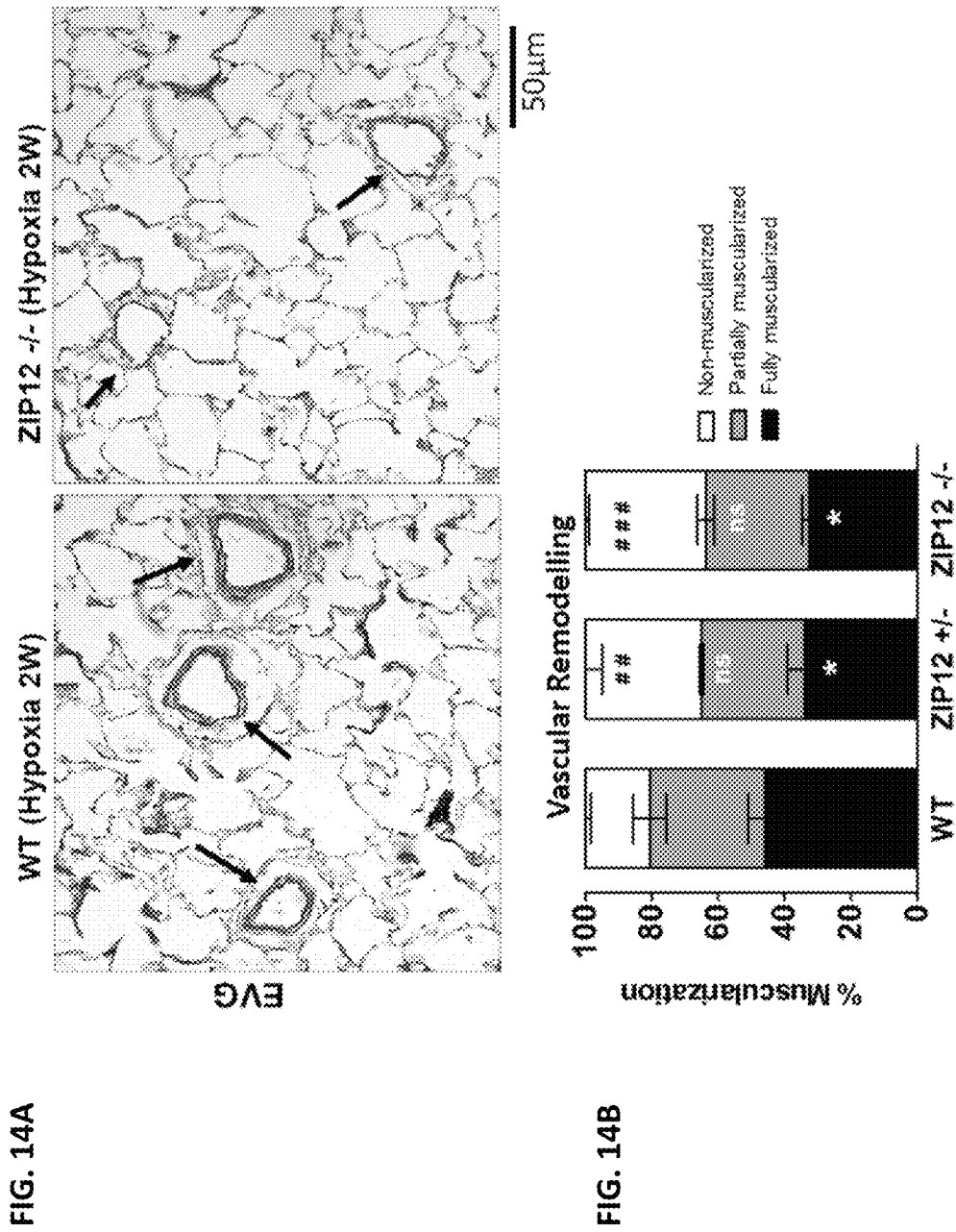
Figure 14C:
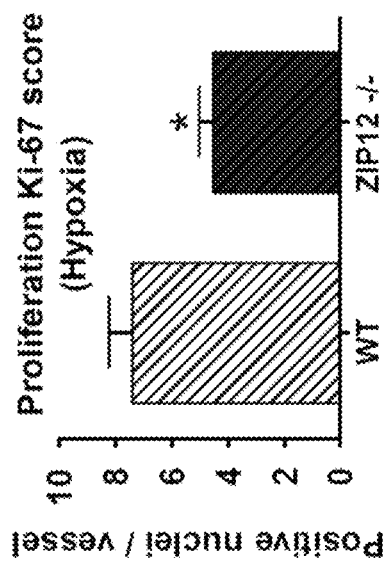
Figure 14D:
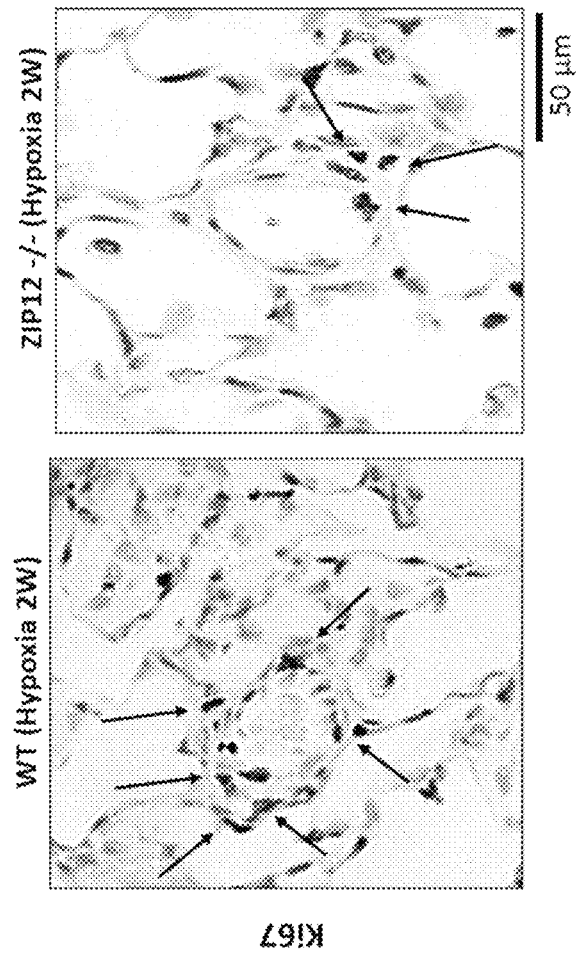
Figure 14E:
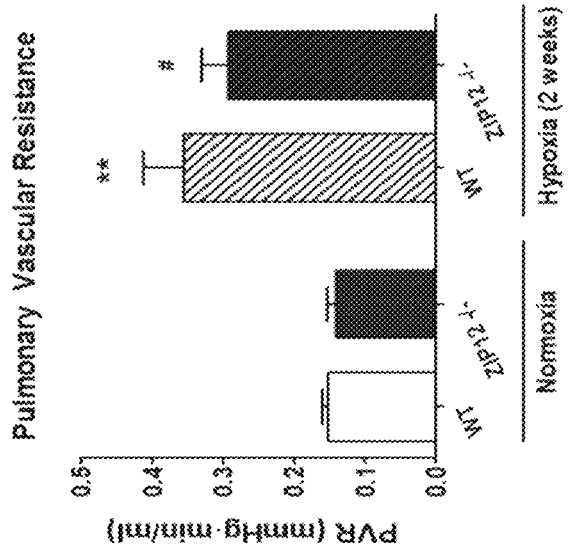
Figure 14F:
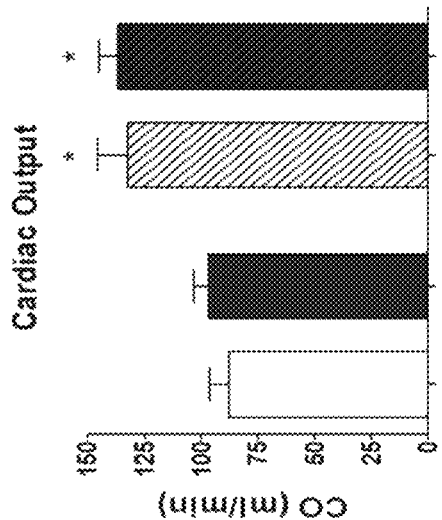
Figure 14G:
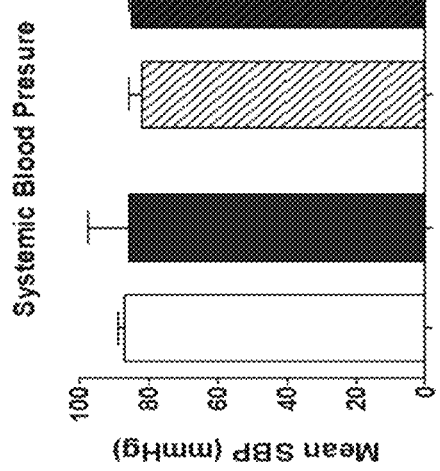

FIG. 14A-14G: FIG. 14A. Representative lung sections from wild-type (WT) and ZIP12 −/− rats 2 weeks after hypoxia exposure. Elastic van Gieson (EVG) staining showing double elastic lamina (red arrow) in WT but single elastic laminae (blue arrow) in ZIP12−/− rats. FIG. 14B. Genetic disruption of ZIP12 in WKY rat attenuated pulmonary vascular remodelling after 2 weeks exposure to a 10% O2 atmosphere compared to wild-type (WT) rats (n=5 each group). *P<0.01 compared to WT (% of fully muscularised vessels); ##P<0.01, ###P<0.001 compared to WT (% of non-muscularised vessels) after One-Way ANOVA analysis followed by Bonferroni's multiple comparison test. FIG. 14C. Ki67 staining showing reduced proliferation in hypoxic ZIP12−/− rat lungs compared to the WT strain. *P<0.01 compared to WT. FIG. 14D. Representative sections from hypoxic WT and ZIP12−/− rats lungs showing differences in staining with the proliferation marker, Ki67. FIG. 14 E-14G. Genetic disruption of ZIP12 in WKY rat did not influence e. systemic blood pressure (SBP) or f. cardiac output (CO) but attenuated hypoxia-induced increases in g. pulmonary vascular resistance (n=7 each group). Values are expressed as the mean±standard error of the mean (SEM). *P<0.05, **P<0.01 compared to normoxic rats, #p<0.05 compared to so wild-type (WT) hypoxic rats after One-Way ANOVA analysis followed by Bonferroni correction for multiple testing.

Figures 15A, 15B:
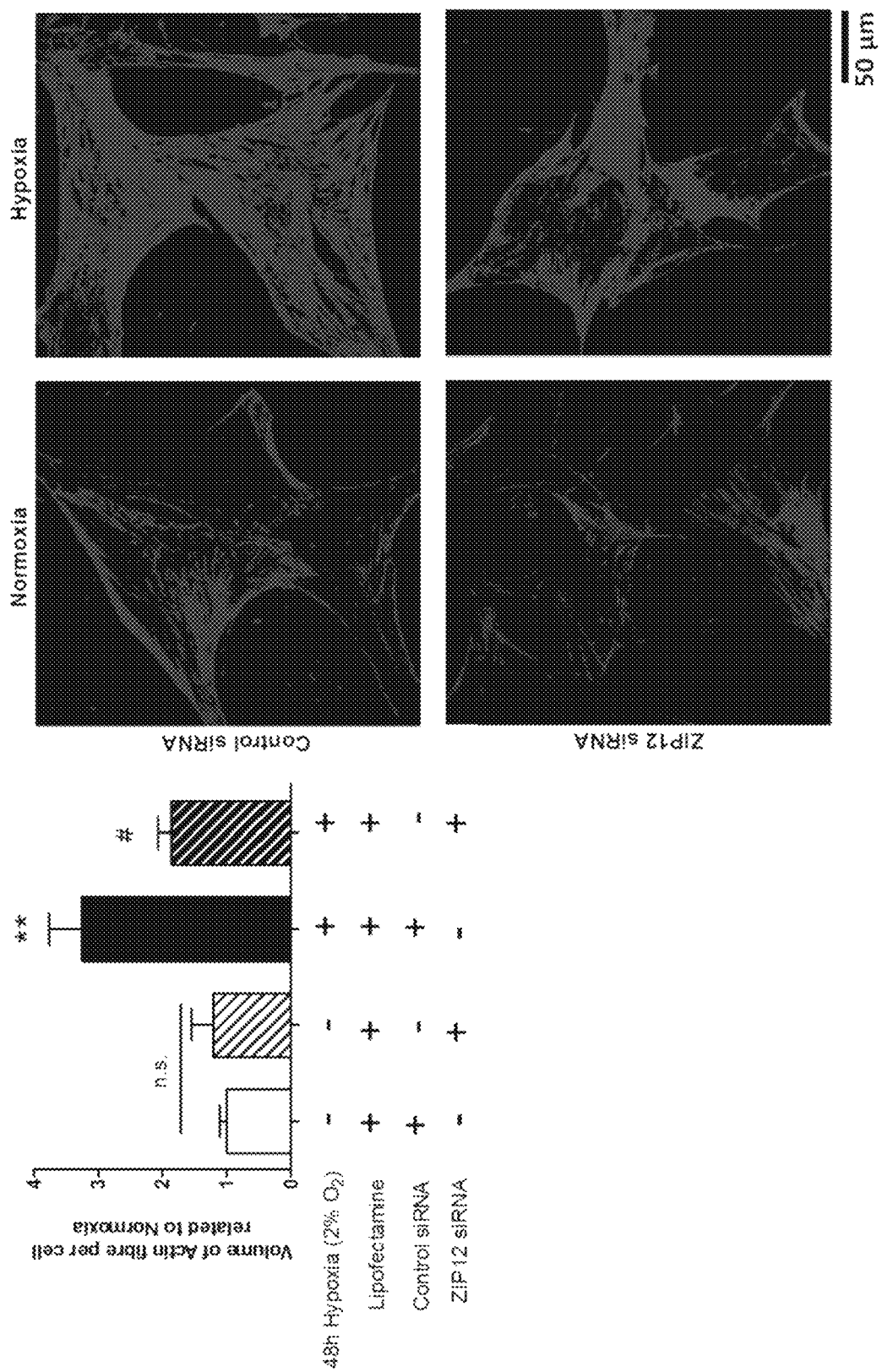
Figure 15C:
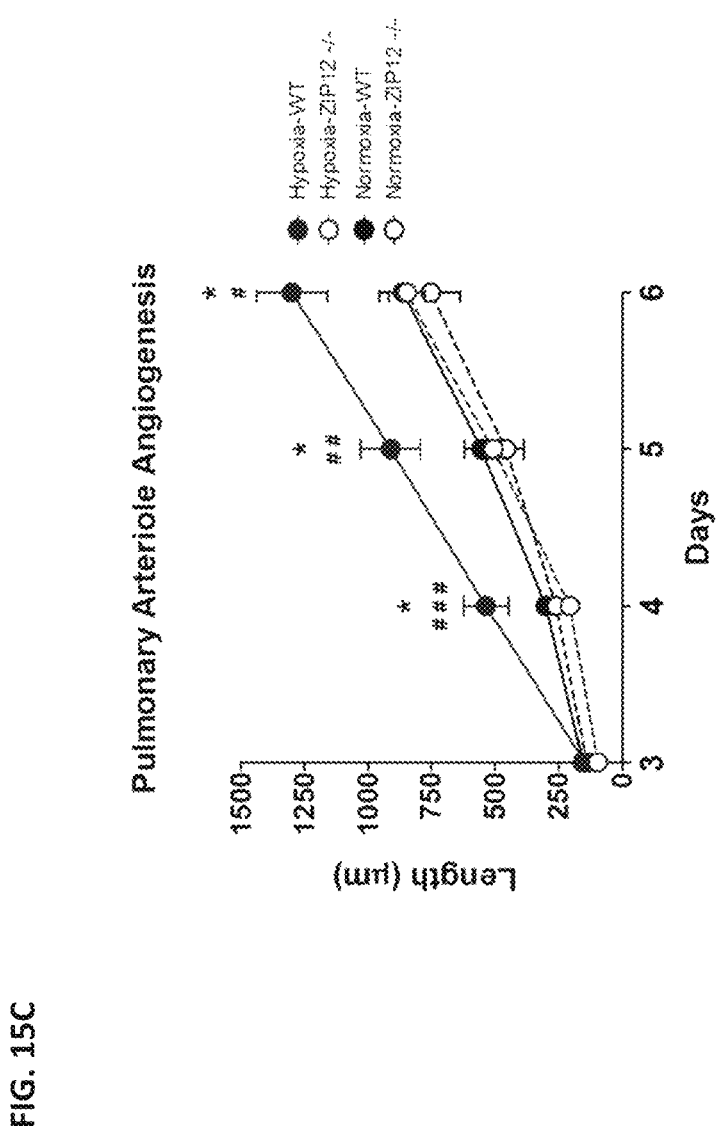
Figure 15D:
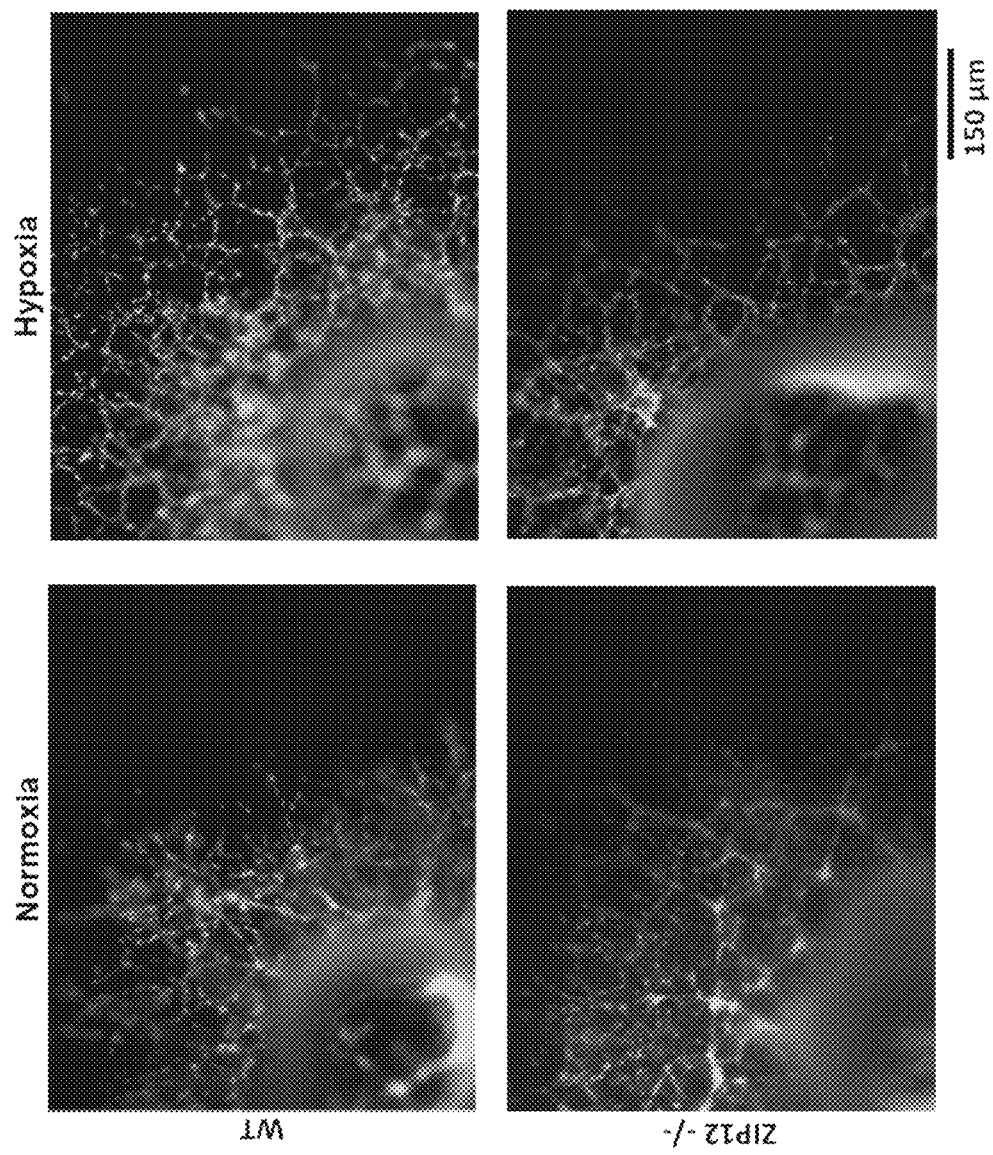

FIG. 15A-15D: Effect of ZIP12 inhibition on stress fibre formation and ex vivo angiogenesis. FIG. 15A. ZIP12 targeted siRNA inhibition attenuates stress fibre formation in human pulmonary vascular smooth muscle cells (HPASMCs) in hypoxia (n=5 each group). **p<0.01 compared to normoxia control group, #p<0.05 compared to hypoxia control group. FIG. 15B. Representative pictures of actin stress fibre in HPASMCs. FIG. 15C. ex vivo angiogenesis studies demonstrated that vascular outgrowth from ZIP12−/− pulmonary vessels in response to hypoxia was attenuated compared to vessels from wild-type (WT) rats (n=12 each group, 2 rings/rat, 6 ZIP12 −/− and 6 WT rats). *P<0.05 compared to normoxia WT group; #P<0.05, ##P<0.01 and ###P<0.001 compared to hypoxia ZIP12−/− group. FIG. 15D. Representative pictures of pulmonary arteriole ring outgrowth at day 6.

Figure 16A:
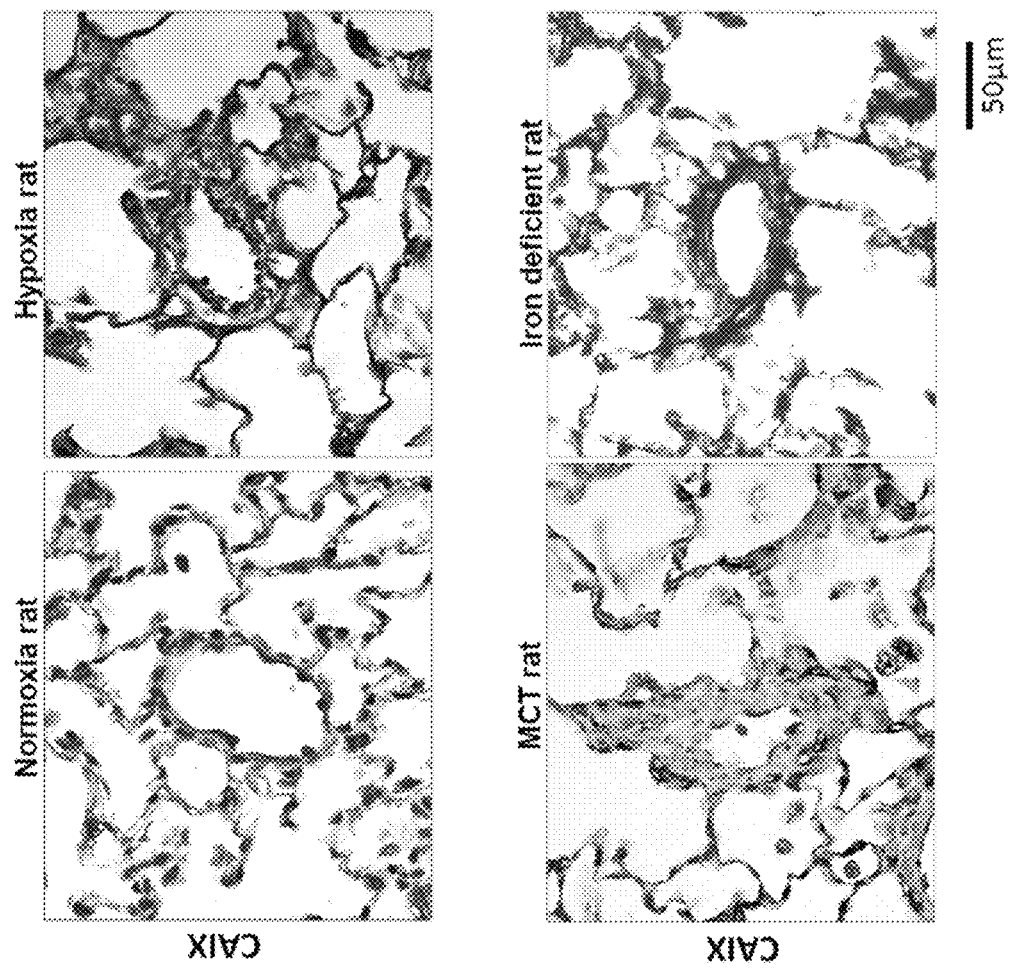
Figures 16B, 16C:
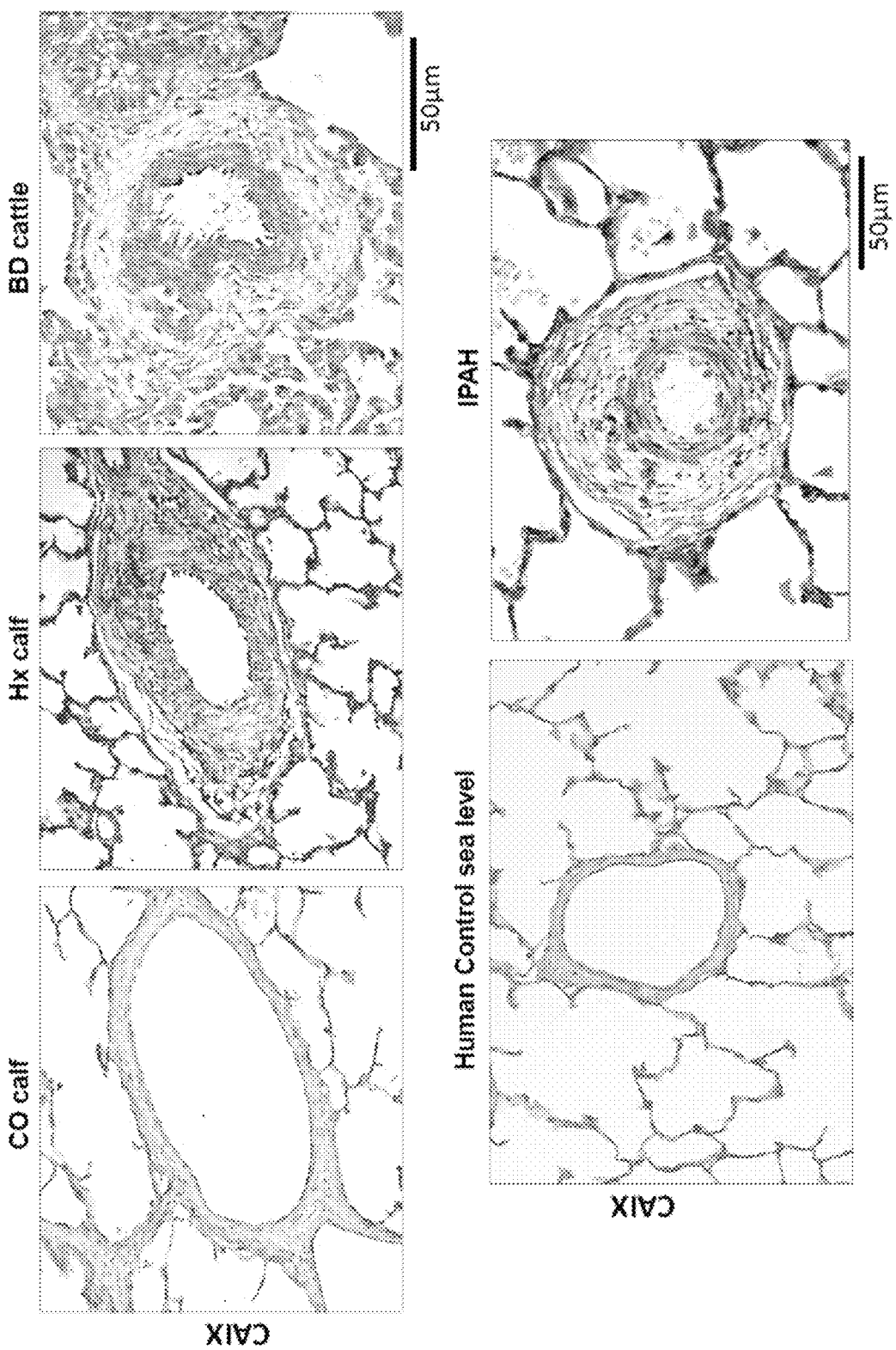

FIG. 16A-16C: Carbonic anhydrase (CAIX) expression. FIG. 16A. Representative sections demonstrating increased CAIX expression in remodeled pulmonary arterioles in the lungs of rats exposed to alveolar hypoxia (2 weeks), monocrotaline (MCT, 3 weeks) or a chronic iron deficient diet (4 weeks). FIG. 16B-16C. No CAIX staining was detected in pulmonary arteries of low altitude (normoxia control, CO calf) calves and sea level humans, but prominent CAIX immunostaining was observed in the remodeled pulmonary arteries of calves with severe pulmonary hypertension (Hx calf), in cattle with naturally occurring pulmonary hypertension ("Brisket disease", BD) as well as patients with idiopathic pulmonary arterial hypertension (IPAH).

Figures 17A, 17B, 17C:
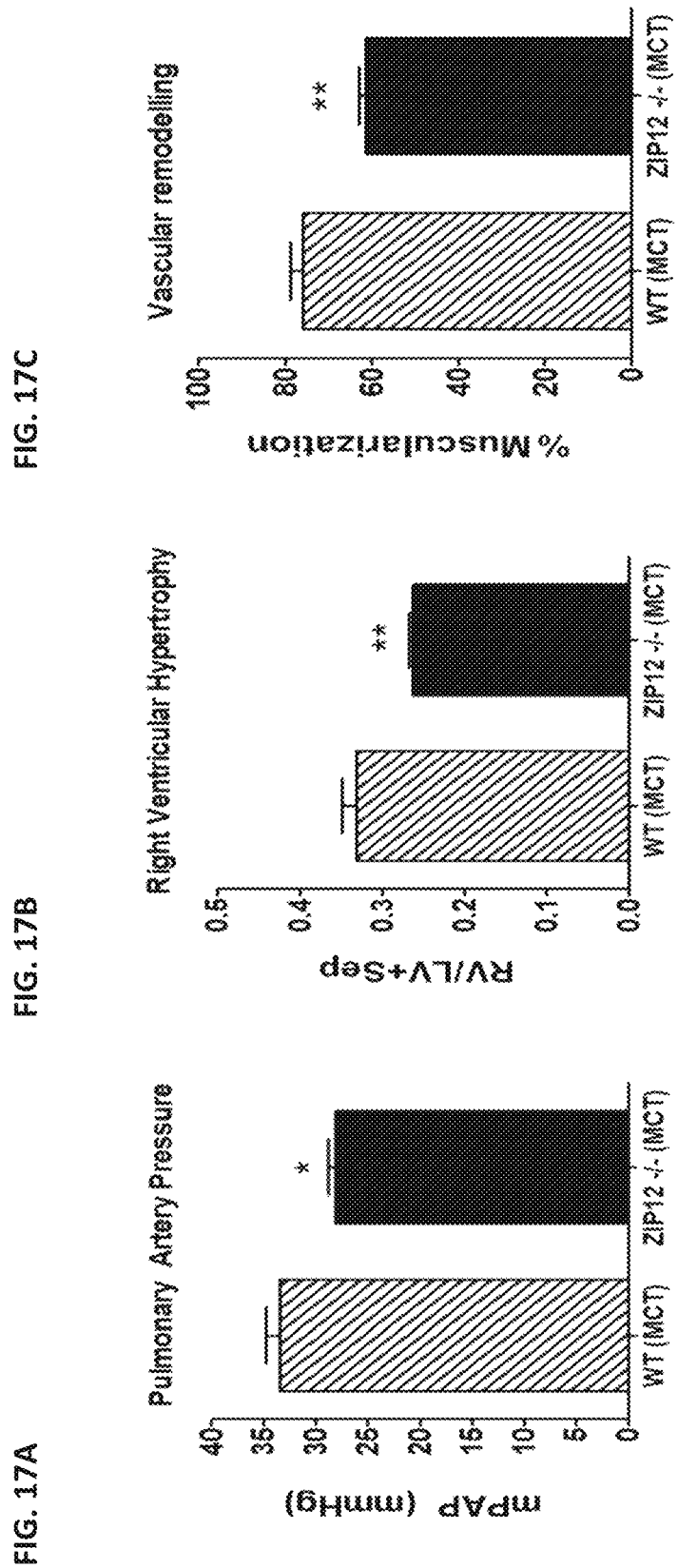
Figure 17D:
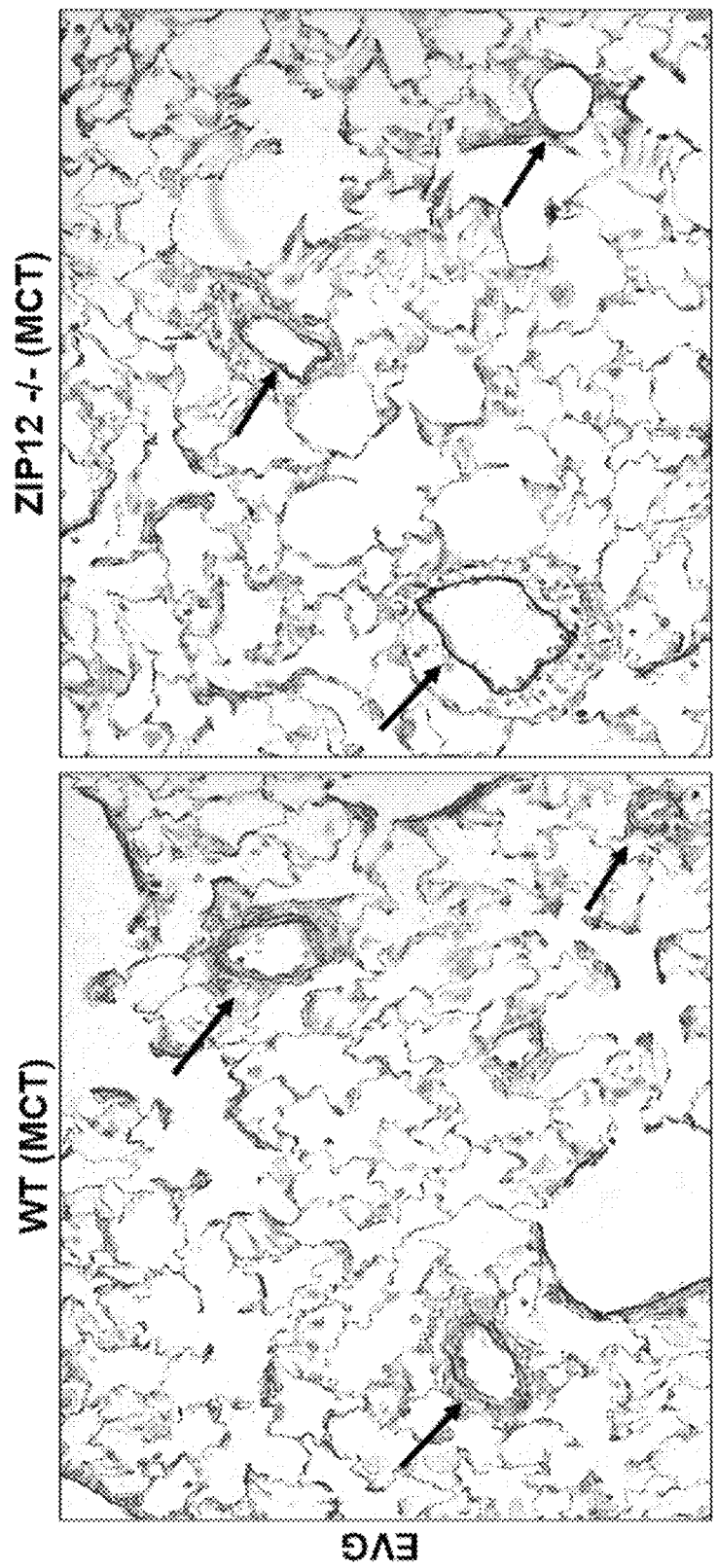

FIG. 17A-17D: Genetic disruption of ZIP12 in WKY rat attenuated monocrotaline-induced pulmonary hypertension. FIG. 17A. Mean pulmonary artery pressure (mPAP), FIG. 17B. right ventricular hypertrophy (RV/LV+Septum) and FIG. 17C. pulmonary arteriole muscularisation. (n=5 each group). Values are expressed as the mean±standard error of the mean (SEM). *P<0.05, **P<0.01 compared to wild-type (WT) monocrotaline group after unpaired Student t-test. FIG. 17D. Representative lung sections from wild-type (WT) and ZIP12 −/− rats 3 weeks after monocrotaline injection. Elastic van Gieson (EVG) staining showing double elastic lamina (red arrow) in WT but single elastic laminae (blue arrow) in ZIP12−/− rats.

Figure 18:
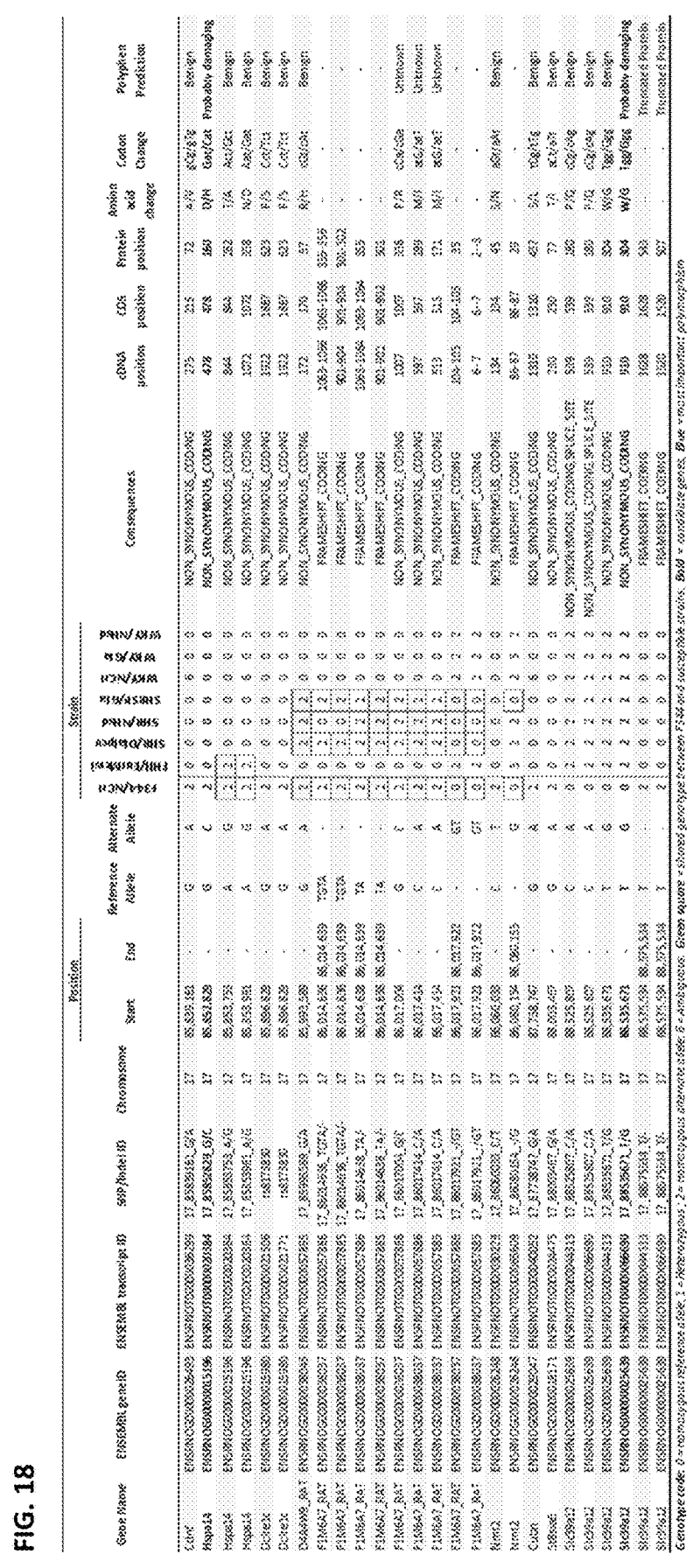

FIG. 18: Frameshift and Non-Synonymous coding mutations in the refined congenic interval of F344 and the other hypoxia susceptible strains, WKY, spontaneously hypertensive (SHR) and fawn-hooded (FHH) rat strains.

FIG. 19: Polymorphism markers for congenic strain genotyping. Forward primers top to bottom: SEQ ID NOs: 5, 7, 9, 11, 13, 15, 17, 19, 21, 23, 25, 27, 29, 31, 33, 35, 37, and 39. Reverse primers top to bottom: SEQ ID NOs: 6, 8, 10, 12, 14, 16, 18, 20, 22, 24, 26, 28, 30, 32, 34, 36, 38 and 40.

EXAMPLES

The materials and methods employed in the studies described in the Examples were as follows, unless otherwise indicated:

Animals

Inbred Wistar-Kyoto (WKY, Charles River, UK) and Fischer 344 rats (F344, Harlan, UK) were used. Animals were maintained at a constant temperature (20° C. to 22° C.) with a 12-hour on/12-hour off light cycle, with food and water ad libitum. All experiments were conducted in accordance with the UK Home Office Animals (Scientific Procedures) Act 1986 (London, UK).

Generation of Congenic and Sub-Congenic Strains

To investigate the involvement of the chromosome 17 QTL in the pulmonary hypertension (PH) phenotype, the inventors introgressed the F344 chromosome QTL segment into the WKY genetic background by repeated backcrossing (ZHAO, L. et al., Right ventricular hypertrophy secondary to pulmonary hypertension is linked to rat chromosome 17: evaluation of cardiac ryanodine Ryr2 receptor as a candidate. Circulation 103, 442-447, 2001). The inventors produced a congenic rat strain, R47A (WKY.F344-D17Got91/D17Rat51), which contains 15 Mbp from the F344 donor region that maps to the distal end of the QTL on the WKY background.

Subsequently, the inventors generated 3 sub-congenic strains Sub-A (WKY.F344-D17Got91/D17Rat47), Sub-B (WKY.F344-D17Rat47/D17Rat51) and Sub-C (WKY.F344-D17Rat131/D17Rat51). These three recombination events divide the R47A congenic interval into three smaller and overlapping sub-congenic intervals (Supplementary FIG. 1).

Microsatellite Genotyping of Congenic Rats

Congenic and sub-congenic rats were genotyped using simple sequence length polymorphism (SSLP) markers (Supplementary Table 2). In order to reduce the unknown regions between the markers, rats were also genotyped using primers specifically designed to amplify known regions containing insertions or deletions in one of the two parental strains (Supplementary Table 2). Genomic DNA was isolated from rat ear clippings using Hot Sodium Hydroxide and Tris (HotSHOT) extraction (TRUETT, G. E. et al. Preparation of PCR-quality mouse genomic DNA with hot sodium hydroxide and tris (HotSHOT). BioTechniques 29, 52, 54, 2000). Forward primers were fluorescently labelled with 6-FAM. PCR products together with the fluorescent size marker (ROX 400HD, Applied Biosystems) were diluted in formamide and run on a 3730xl DNA Analyzer (Applied Biosystems). Results were analysed using GeneMapper V3.7 software (Applied Biosystems).

Illumina Genome Sequencing Library Preparations

Five micrograms of male WKY/Ncrl (two animals) and F344/Ncrl (one animal) rats were used to construct paired-end whole-genome libraries with 300-550 bp insert size. Genomic DNA was prepared by standard phenol chloroform extraction followed by treatment with DNAse free RNAse. DNA quality was assessed by spectrophotometry (260/280 and 260/230) and gel electrophoresis before library construction. Genomic DNA was sheared for 90 sec (Covaris S2, KBioscience, Herts, UK), using 10% duty cycle, 5 intensity and 200 cycles per burst. The shearing efficiency was assessed by Qubit 2.0 fluorometer measurements (Life Technologies Ltd, Paisley, UK) and gel electrophoresis. The library was prepared as recommended (Illumina Genomic DNA sample prep kit protocol) with 9 cycles of PCR amplification (Illumina Inc., Hayward, Calif.). Constructed libraries were assessed with an Agilent 2100 bioanalyser using a HS DNA assay (Agilent Technologies, Edinburgh, UK) and quantified using a KAPA Illumina SYBR Universal Lib QPCR kit (Anachem Ltd, Bedfordshire, UK). The resulting libraries were sequenced on an Illumina HiSeq2000 following the manufacturer's instructions. Polymorphisms were confirmed by capillary sequencing.

Generation and Genotyping of WKY.Slc39a12 (+/−) and (−/−) Rats

CompoZr™ Custom Zinc Finger Nucleases targeting the rat Slc39a12 gene were designed and purchased from Sigma-Aldrich (Supplementary FIG. 3). Pronuclei from fertilized WKY oocytes were microinjected with ZFN mRNA (2 ng/μl). Three out of eleven pups were positive for Slc39a12 mutations, as revealed by Cel-I surveyor assay and gene sequencing (CUI, X. et al. Targeted integration in rat and mouse embryos with zinc-finger nucleases. Nature biotechnology 29, 64-67, 2011). One pup (mutant 77) hosted a stop codon 15 amino acids from the ZFN binding site, resulting in a truncated protein of 490 amino acids (54 KDa), 198 amino acids smaller than the wild type protein, and introduced a sequence coding for 5'-ATTTAAAT-3', a binding site for the SwaI restriction enzyme. Mutant 77 was selected as a founder to mate with a WKY female. Pups were genotyped by amplifying DNA and digesting with SwaI. The primers used to amplify the region of interest were forward 5'-GCAATGGTTTTCCACAGTGA-3' (SEQ ID NO: 1) and reverse 5'-GCGCACTGAGGCTTTAAGAA-3' (SEQ ID NO: 3).

Pulmonary Hypertension Phenotyping

Animals were housed at a constant temperature (20° C. to 22° C.) with a 12-hour on/12-hour off light cycle, with food and water ad libitum. Male rats aged 10-12 weeks were studied in batches, with the parental WKY strain as an internal control in each batch studied. Sample sizes were chosen on the basis of experience of pulmonary artery pressure variation in the parental strains. A sample size of at least n=5 per group was predicted to detect a difference in mean pulmonary arterial pressure ≥5 mmHg (standard deviation=3) with 95% power with 95% confidence. Additional animals were studied to obtain sufficient tissue for supportive analyses. Pulmonary hypertension was induced by placing animals in a normobaric hypoxic chamber (FIO2=10%) for 2 weeks or by subcutaneous injection of monocrotaline (60 mg/kg; Sigma-Aldrich). All studies were performed using the same equipment and all haemodynamic measurements made by the same operator. At the end of each experimental period, animals were weighed and anesthetized (Hypnorm 1 ml/kg i.m.; Mydazolam 0.8 ml/kg i.p.). Pulmonary arterial pressure was measured with a pre-curved catheter inserted through the right jugular vein. Systemic blood pressure was assessed via carotid artery cannulation. Cardiac output was measured by thermodilution. Pulmonary vascular resistance (PVR) was calculated using the standard equation: PVR=mean pulmonary artery pressure/cardiac output. All data were recorded with a PowerLab Data Acquisition system (AD Instruments) and analysed using LabChart 7 software.

The animals were then killed and the heart dissected and individual chamber weights recorded. The ratio of right ventricle to left ventricle plus the septum mass (RV/LV+sep) was calculated as RV hypertrophy index. Some collected tissues were snap frozen in liquid nitrogen and stored at −80° C. for further biochemical measurements. The left lung was fixed by inflation with 10% formalin in phosphate-buffered saline, embedded in paraffin, sectioned for histology. Transverse rat lung sections were processed for elastic van Gieson (EVG) staining. Peripheral vessels <100 μm diameter were counted at ×40 magnification objective and pulmonary vascular remodelling was expressed as the proportion of vessels with double elastic lamina (>75% of the circumference as fully muscularised, 25-75% as partially muscularised) to total vessels counted. Counting was performed twice by observers blind to treatment.

Ex Vivo Angiogenesis Assay of Pulmonary Arteriole

Pulmonary arterioles ($1^{st}$ and $2^{nd}$ order) were dissected from rat lungs viewed under the microscope. One mm sections were placed in matrigel 50 μl/well) in a 96-well plate, allowed to gel for 30 mins at room temperature, then incubated for up to 6 days with endothelial cell culture medium MV2 with 5% foetal calf serum (PromoCell). On days 3, 4, 5 and 6, sprouts (outgrowth) were measured under the microscope (4× objective) as previously described (APLIN, A. C. et al. The aortic ring model of angiogenesis. Methods in enzymology 443, 119-136, doi:10.1016/S0076-6879(08)02007-7, 2008). On day 6 arteriole ring fluorescent images were taken by staining the tissue with calcein (Invitrogen) for 15 minutes at 37° C.

Anti-ZIP12 Antibody Production

An antibody raised against the five last amino-acids at the C terminus (Ct) of both the human and the rat ZIP12 protein was produced in rabbits following previous methodology (EDWARDS, R. J. Targeting antipeptide antibodies toward cytochrome P450 enzymes. Methods in molecular biology 320, 173-182, doi:10.1385/1-59259-998-2:173, 2006). Rabbits were immunized with synthetic peptides conjugated to keyhole limpet hemocyanin ([CYS(KLH)]QNIKI). Peptide sequence was confirmed to be ZIP12 specific using RStudio. Immunized rabbit serum containing anti-ZIP12 antibody specificity was confirmed by immunoblotting with rat lung lysates or human pulmonary smooth muscle cells. A single band at about 70 kDa was visible in the immunoblots.

Lung Immunohistochemistry and Immunofluorescence

Human IP AH and control lung samples were obtained from the Imperial College Pulmonary Hypertension biorepository (ethics reference numbers: 01-210 & 2001/6003). Kyrgyz high-altitude lung samples were obtained from post-mortem lung (reference 02-23/880).

Lung sections were immunostained with rabbit anti-ZIP12 (1:1000), Ki67 (1:50, Thermo Scientific) and rabbit anti-CAIX (1:100) antibodies. For immunohistochemistry, horseradish peroxidase conjugated secondary anti-rabbit antibody (1:200) was used. Double immunofluorescence with anti-αSMA (1:100) was performed using fluorescence secondary antibodies, anti-mouse Alexa 488 and anti-rabbit Alexa 568 (1:2000, Invitrogen). Images (green for ZIP12 and red for αSMA) were detected under Leica confocal microscope (TCS SP2 AOBS).

Human pulmonary artery smooth muscle cell culture

Human pulmonary artery smooth muscle cells (HPASMCs) from PromoCell and Lonza were grown in Human Smooth Muscle Cell Growth Medium 2 (Promo-Cell). The cells were cultured under normal oxygen tension (20% 02, 5% CO2) or exposed to hypoxia (2% O2, 5% C02, 92% N2) for 48-72 hr. A Bromodeoxyuridine (BrdU) cell proliferation assay (Millipore) was used to assess cell proliferation following manufacturer's conditions.

ZIP12 siRNA Transfection

Cells were transfected overnight with 50 pmol siRNA against ZIP12 (S8397, Ambion), or negative siRNA (4390844, Ambion) as a control, using Lipofectamine RNAiMAX (Invitrogen Life Technologies) according to manufacturer's conditions.

Quantification of Actin Fibre Formation

Cells were cultured on plastic coverslips (Nunc), transfected with scramble or ZIP12 siRNA and exposed to hypoxia as described previously. After 48 h exposure, cells were fixed with 4% formaldehyde solution in phosphate buffered saline (PBS) for 10 minutes at room temperature. Cells were then incubated with Alexa 568-conjugated phalloidin (1/200; Invitrogen) for F-actin detection under confocal microscopy. Sequential XYZ-sections (approximately 12 sections of 1 $\mu m^2$/view) were obtained and 3D images were reconstructed. Quantification of actin stress fibres was determined by volume rendering in Image-J. Actin volume per cell was expressed as fold increase from normoxic control (value set at 1).

Quantification of Zinc Concentration by FRET Measurement

Cells on coverslips were washed twice in Krebs-HEPES-bicarbonate (KHB) buffer (140 mMNaCl, 3.6 mM KCl, 0.5 mM NaH2PO4, 0.2 mM MgSCO4, 1.5 mM CaCl2), 10 mM Hepes, 25 mM NaHCO3), which was warmed, bubbled with 95% O2:5% CO2, set to pH 7.4, and contained 3 mM glucose. Imaging of zinc using eCALWY sensors was earned out as optimized before (VINKENBORG, J. L. et al. Genetically encoded FRET sensors to monitor intracellular Zn2+ homeostasis. Nature methods 6, 737-740, doi: 10.1038/nmeth.1368, 2009); BELLOMO, E. A. et al. Glucose regulates free cytosolic Zn(2)(+) concentration, Slc39 (ZiP), and metallothionein gene expression in primary pancreatic islet beta-cells. The Journal of biological chemistry. 286, 25778-25789, doi:10.1074/jbc.M111.246082, 2011). Briefly, cells were maintained at 37° C. throughout with a heating stage (MC60, LINKAM, Scientific Instruments), and KHB buffer was perfused (1.5 to 2 ml/minute) with additions as stated in the Figures. Images were captured at 433 nm monochromatic excitation wavelength (Polychrome IV, Till photonics) using an Olympus IX-70 wide-field microscope with a 40×/1.35 NA oil immersion objective and a zyla sCMOS camera (Andor Technology) controlled by Micromanager software8. Acquisition rate was 20 images/minute. Emitted light was split and filtered by a Dual-View beam splitter (Photometries) equipped with a 505dcxn dichroic mirror and two emission filters (Chroma Technology—D470/24 for cerulean and D535/30 for citrine).

Image analysis was performed with ImageJ (SCHNEIDER, C. A. et al. NIH Image to ImageJ: 25 years of image analysis. Nat Methods 9, 671-675, 2012) software using a home-made macro and the fluorescence emission ratios were derived after subtracting background. Steady-state fluorescence intensity ratio citrine/cerulean (R) was measured, then maximum and minimum ratios were determined to calculate free $Zn2+$ concentration using the following formula: $[Zn2+]=Kd\times(Rmax-R)/(R-Rmin)$. The maximum ratio (Rmax) was obtained upon intracellular zinc chelation with 50 μM TPEN and the minimum ratio (Rmin) was obtain upon zinc saturation with 100 μM ZnCl2 in the presence of the Zn2+ ionophore, pyrithione (5 μM) (VINKENBORG, J. L. et al. Genetically encoded FRET sensors to monitor intracellular Zn2+ homeostasis. Nature methods 6, 737-740, doi:10.1038/nmeth.1368, 2009).

HIF-Motif Analysis and Cloning

HOMER (HEINZ, S. et al. Simple combinations of lineage-determining transcription factors prime cis-regulatory elements required for macrophage and B cell identities. Molecular cell 38, 576-589, doi:10.1016/j.molcel.2010.05.004, 2010) was used to scan for HIF-1α and HIF-2a recognition motifs in the region 2 kb up-stream and 1.5 kb down-stream of the ZIP12 transcription start site. Results with a HOMER score <6.5 were discarded. A 5' region of ZIP12 gene containing these motif (HRE) (human (hg19) chr10:18,240,587-18,242,100) was cloned into the multicloning site of PGL4.10, which encodes the luciferase reporter gene luc2, by Gibson Assembly (NEB, E2611S).

Three nucleotide substitutions in the core of the predicted HIF1/2α binding site motif were created by site-mutagenic PCR to produce a disabling mutant (FIG. 2d).

Transfection and Luciferase Assay

HPASMCs were seeded in 24 well plates at 70-80% confluence. Cells were transfected with 300 ng of each plasmid together with 2 ng of Renilla plasmid using Lipofectamine® 2000 (Life Technologies), exposed to hypoxia and lysed according to the manufacturer's conditions. Luciferase activity was measured using Dual-Luciferase® Reporter Assay Chemistry (Promega) as previously described (PASQUALI, L. et al Pancreatic islet enhancer clusters enriched in type 2 diabetes risk-associated variants. Nature genetics 46, 136-143, doi:10.1038/ng.2870, 2014). Experiments were repeated in two cells lines, n=6 per line.

Chromatin Immunoprecipitation and PCR

Specific protein-DNA interactions were examined by chromatin immunoprecipitation (ChIP) followed by quantitative PCR (Chromatin immunoprecipitation Assay Kit, Millipore). Protein-DNA crosslinks were achieved by fixation with 1% formaldehyde for 10 minutes at room temperature. DNA-protein complexes from $2 \times 10^6$ cells were sheared to lengths between 200 and 500 base-pairs by sonicator (Bioruptor). The precleared fragments were incubated with 10 μg of HIF-1α or HIF-2a specific antibody (Novus Biologicals), or without antibody (as a negative control) overnight, followed by immunoprecipitation by Protein A Agarose/Salmon Sperm DNA (50% Slurry). The crosslinks were reversed by heating at 65° C. overnight, followed by Proteinase K digestion at 45° C. for 2 hours. DNA was then recovered with QIAquick PCR purification kit (Qiagen) for quantitative PCR to prove affinity against ZIP12 promoter region (FIG. 2d). Experiments were conducted in two separate cell lines (n=3 each) and gave the same result.

Quantitative PCR was performed as previously described in the methodology, using 1 ul of DNA sample, and using the forward primer 5-TTTCCCAACCTGGGTCCTAT-3 (SEQ ID NO: 3) and the reverse primer 5-AGCAGCCAAAAAGCTTGCTA-3 (SEQ ID NO: 4). Ct values were normalized compared to the values detected in the starting non-immunoprecipitated DNA sample (input). Protein-DNA affinity was confirmed when normalized Ct values were above the basal levels measured in the negative control.

Quantitative Real Time RT-PCR

RNA was extracted from lungs using RNeasy Mini Kit (Qiagen). PCR was performed with an ABI 7500 Sequence Detection System (Applied Biosystems). Quantitative PCR was performed using a two-step protocol starting with cDNA synthesis using the ImProm-II™ Reverse Transcription System (Promega), followed by PCR using the Power SYBR Green PCR Master Mix (Applied Biosystems). A total of 100 ng of cDNA per sample was used. All samples were amplified using biological triplicates with two technical replicates per sample. The 7500 Sequence Detection System software (Applied Biosystems) was used to obtain CT values. Results were analysed using the comparative CT method (SCHMITTGEN, T. D. & LIVAK, K. J. Analyzing real-time PCR data by the comparative C(T) method. Nature protocols 3, 1101-1108, 2008). Samples were normalized to a reference gene, Ubc (for rat samples) or Cyclophilin (for human cell samples), to account for cDNA loading differences.

Western Blot

Frozen rat tissues (lungs) and cell pellets were homogenized in RIPA buffer (50 mM tris-HCl, pH 8.0, 150 mM sodium chloride, 1.0% Igepal, 0.5% sodium deokycholate, 0.1% sodium dodecyl sulphate) (Sigma) supplemented with protease inhibitor (Roche). Western blotting was performed using Mini-PROTEAN® TGX™ Precast Gels (Bio-rad) following the manufacture's suggestions. Blots were incubated for 1 h at room temperature with Anti-ZIP12 (1:10,000); Anti-HIF1α (1:1000, Novus Biological); or Anti-HIF2α (1:1000, Novus Biological). Proteins were detected by Clarity western ECL substrate (Bio-rad). Optical densities of individual bands were measured using ImageJ software and protein expressions were standardised with Vinculin.

Statistical Analysis

Data are presented as mean±the standard error of the mean (SEM). Data were tested for normality using the Kolmogorov-Smirnov. All data were confirmed normally distributed with similar variance between comparator groups. Data were analysed using one-way ANOVA followed by Bonferroni post-test adjustment for multiple comparisons or unpaired t-test. Graphpad Prism was used for all statistical analysis.

Other Bioinformatics Analyses

The Ensembl database (FLICEK, P. et al. Ensembl's 10th year. Nucleic acids research 38, D557-562, doi:10.1093/nar/gkp972, 2010) was mined with the BioMart tool (HAIDER, S. et al. BioMart Central Portal-unified access to biological data. Nucleic acids research 37, W23-27, doi:10.1093/nar/gkp265, 2009) to identify all transcribed elements in the Cl region. Search was limited to chromosome 17 between positions 85,072,475-93,347,758. PolyPhen analysis was used to predict the possible impact of described SNP on amino acid substitution on the structure and function of a human protein (ADZHUBEI, I. A. et al. A method and server for predicting damaging missense mutations. Nat Methods 7, 248-249, doi:10.1038/nmetho410-248, 2010).

Example 1—the Pulmonary Vascular Response to Hypoxia in the F344 Rat is Influenced by a Region of Chromosome 17 Containing Slc39a12

The inventors have reported previously that the Fisher 344 (F344) rat strain is resistant to hypoxia-induced pulmonary hypertension compared to the Wistar Kyoto (WKY) strain (ZHAO, L. et al. Right ventricular hypertrophy secondary to pulmonary hypertension is linked to rat chromosome 17: evaluation of cardiac ryanodine Ryr2 receptor as a candidate. Circulation 103, 442-447, 2001). The inventors then performed linkage analysis of a F2 population derived from inbred WKY x F344 rats identified a quantitative trait locus (QTL) on chromosome 172. Based on this observation, the inventors next conducted ten successive microsatellite-guided backcrosses of offspring with WKY rats and derived two congenic strains in which the original QTL was dissected and represented as partially overlapping regions of a donor F344 genome interposed onto the genetic background of the WKY recipient strain (FIGS. 6, 7). Resistance to hypoxia-induced pulmonary hypertension was detected in one of the congenic strains (R47A, FIG. 1a-d, Supplementary FIG. 2,3). Three subcongenic strains (SubA, SubB and SubC) were derived by further backcrosses of R47A onto the WKY background and the congenic interval was finemapped to a region of 8.28 Mbp containing an estimated 65 genes (rat chr17: 85,072,475-93,347,784) (FIG. 1 and FIG. 7). Whole genome sequencing (>20× coverage) of the WKY and F344 parental strains (ATANUR, S. S. et al. Genome sequencing reveals loci under artificial selection that underlie disease phenotypes in the laboratory rat. Cell 154, 691-703, doi:10.1016/j.cell.2013.06.040, 2013) revealed 13 non-synonymous coding SNPs affecting 9 genes within the refined congenic interval, and 6 indels resulting in frameshift mutations in 4 genes (FIG. 17). Polymorphic examination of the 13 SNPs and 6 indels in 2 additional rat strains susceptible to hypoxia-induced pulmonary hypertension (the spontaneously hypertensive and fawn-hooded rat strains, respectively) excluded 5 SNPs and 5 indels and narrowed the genes of interest to 7 (Slc39a12, St8sia6, Cubn, Nmt2, Dclre1c, Hspa14 and Cdnf, FIG. 1e and FIG. 17). Further polyphen analysis allowed the inventors to exclude 5 listed genes (St8sia6, Cubn, Nmt2, Dclre1c and Cdnf) as the non-synonymous coding changes were predicted to be benign. The inventors identified Slc39a12, with a loss of thymidine at position 88,575,534 leading to a frameshift mutation in exon 11, as the highest priority candidate gene for further investigation.

Example 2—Slc39a12 Encodes a Cine Transporter, ZIP12, which is Up-Regulated in Pulmonary Vascular Tissue from Mammals Exposed to Chrome Hypoxia Slc39a12 encodes the solute carrier 39 zinc transporter family (ZIP1-14) member 12 (ZIP12) and has high specificity for zinc (CHOWANADISAI, W., GRAHAM, D. M., KEEN, C. L., RUCKER, R. B. & MESSERLI, M. A. Neurulation and neurite extension require the zinc transporter ZIP12 (slc39a12). Proceedings of the National Academy of Sciences of the United States of America 110, 9903-9908, doi:10.1073/pnas.1222142110, 2013). The ZIP family tightly regulates cellular zinc homeostasis in numerous cell types by promoting zinc uptake from the extracellular space or release from intracellular compartments. The rat Slc39a12 gene contains 12 exons and the ZIP12 protein comprises 688 amino acids with a secondary structure comprising 8 transmembrane domains (TMD). In the F344 strain the frameshift mutation in Slc39a12 introduces a stop-codon predicting a C-terminal truncated ZIP12 protein of 553 amino acids (FIG. 9). This affects the conserved zinc transporting aqueous cavity between TMD IV to V, resulting in the loss of the metalloprotease moth (HEXPHE), which would be expected to lead to a reduction in zinc transport (LIUZZI, J. P. & COUSINS, R. J. Mammalian zinc transporters. Annual review of nutrition 24, 151-172, doi: 10.1146/annurev.nutr.24.012003.132402, 2004).

A pathognomonic histological signature of chronic hypoxia-induced pulmonary hypertension is thickening of the pulmonary vascular media (due to hyperplasia and hypertrophy of smooth muscle cells) and the muscularisation of previously unmuscularised pulmonary arterioles (SCHERMULY, R. T., GHOFRANI, H. A., WILKINS, M. R. & GRIMMINGER, F. Mechanisms of disease: pulmonary arterial hypertension. Nature reviews. Cardiology 8, 443-455, doi:10.1038/nrcardio.2011.87, 2011). The inventors found that ZIP12 mRNA levels were very low and ZIP12 protein undetectable by immunohistochemistry in the pulmonary vasculature of adult WKY rats housed in a normal oxygen atmosphere, but WKY rats exposed to hypoxia showed markedly increased lung ZIP12 mRNA levels and pronounced ZIP12 expression in remodeled pulmonary arterioles (FIG. 2a-b and FIG. 10). ZIP12 expression was evident in vascular smooth muscle but also other cell types (endothelial and interstitial cells) known to contribute to structural changes seen in hypoxic lungs. In contrast, and consistent with a frameshift mutation in Slc39a12 predicting a C-terminal truncated protein, ZIP12 was undetectable with an antibody directed at the C-terminus of the protein in the lungs of chronically hypoxic F344 rats (FIG. 1b and FIG. 10).

Example 3—the Relevance of the Invention to Species Other than Rats, Including Humans and Cattle Slc39a12 is highly conserved across species (CHOWANADISAI, W. Comparative genomic analysis of slc39a12/ZIP12: insight into a zinc transporter required for vertebrate nervous system development. PloS one 9, e111535, doi: 10.1371/journal.pone.0111535, 2014) and transcribed constitutively in many tissues (www/biogps.org). To investigate the relevance of the inventors observations m rats to other susceptible animal species, as well as humans, the inventors examined ZIP12 expression in whole lung samples of 1) neonatal calves housed in a normal atmosphere or exposed to hypobaric hypoxia for two weeks (barometric pressure, PB=445 mmHg, equivalent to 4500 m altitude, 12% O2), 2) older (yearling) cattle with naturally occurring pulmonary hypertension (so-called "Brisket disease") developed as a result of prolonged pasturing at high altitude (2,438 to 3,505 m), and 3) human subjects at sea level and Kyrgyz highlanders residing above 2500 m. ZIP12 expression, which is undetectable by immunohistochemistry in healthy bovine and human lung exposed to a normal oxygen atmosphere (FIG. 2c), is clearly visible in the remodeled pulmonary vessels from chronic hypoxia exposure, indicating that ZIP12 up-regulation in pulmonary vasculature is a common response to hypoxia (FIG. 2c).

Example 4—the Regulation of ZIP12 by Hypoxia

To better understand the regulation of ZIP12 by hypoxia, the inventors exposed human pulmonary vascular smooth muscle cells in culture to hypoxia (2% O2). Increased HIF protein and ZIP12 gene expression was observed in hypoxic cells; mRNA levels of other zinc transporters, ZIP6, ZIP7, ZIP10 and ZnT8, were unchanged (FIG. 11). Further examination of the Slc39a12 gene using HOMER analysis (HEINZ, S. et al. Simple combinations of lineage-determining transcription factors prime cis-regulatory elements required for macrophage and B cell identities. Molecular cell 38, 576-589, doi:10.1016/j.molcel.2010.05.004, 2010) revealed a hypoxia response element (HRE) encoding both HIF-1α and HIF-2α binding motifs (FIG. 2d) at 1 kb downstream of the ZIP12 transcription start site (human (hg19) chr10: 18,241,879-18,241,887). The inventors cloned a 1.5 kb fragment of the 5' region of ZIP12 containing this HRE into the luciferase reporter vector, pGL4.10 (FIG. 2d). Human pulmonary vascular smooth muscle cells transfected with the ZIP12 HRE reporter vector demonstrated significantly increased luciferase activity after exposure to hypoxia, while the luciferase activity of cells transfected with the mutant HRE vector (a substitution of the 5'-ACGTG-3' motif by 5'-AGCAG-3'; FIG. 2d) remained at basal normoxia levels (FIG. 2e). Chromatin immunoprecipitation (ChIP) followed by real time PCR confirmed the enrichment of both HIF-1α and HIF-2α binding to this ZIP12 HRE after hypoxia exposure (FIG. 2f).

Example 5—ZIP12 Knockdown Inhibits Hypoxia-Induced Increase in Intracellular Labile Zinc Concentration and Proliferation of Human Pulmonary Artery Smooth Muscle Cells (HPASMCs)

The inventors then explored the contribution of ZIP12 to the regulation of intracellular zinc levels in human pulmonary vascular smooth muscle cells. Intracellular labile zinc measured using a genetically-encoded fluorescence resonance energy transfer (FRET) based zinc probe, eCALWY-410, exhibited a striking increase in cells exposed to hypoxia for 48 h, and this was markedly reduced by inhibiting ZIP12 expression with a targeted siRNA (FIG. 3a-e). Inhibition of ZIP12 expression with siRNA also inhibited hypoxia-induced pulmonary vascular smooth muscle cell proliferation (FIG. 3f). ZIP12 siRNA transfection did not affect intracellular zinc levels or proliferation in normoxia (FIG. 12). These data suggest that disrupted ZIP12 expression exerts a direct effect on pulmonary vascular cells in response to hypoxia and contributes to the resistant pulmonary hypertension phenotype exhibited in F344 strain.

Example 6—Genetic Disruption of ZIP12 in WKY Rat Attenuates Hypoxia-Induced Pulmonary Hypertension To provide direct genetic confirmation that disrupted ZIP12 expression attenuates the pulmonary vascular response to hypoxia the inventors employed zinc finger nuclease technology (CUI, X. et al. Targeted integration in rat and mouse embryos with zinc-finger nucleases. Nature biotechnology 29, 64-67, doi:10.1038/nbt.1731, 2011) to introduce mutations in Slc39a12 in the hypoxia-susceptible WKY rat strain. A mutant line was generated containing a frame-shift resulting in a truncated ZIP12 protein with loss-of-function (FIG. 13). Inter-cross of heterozygous animals generated homozygous (ZIP12−/−), heterozygous (ZIP12+/−) and wild-type rats that were then exposed to hypoxia (10% O2) for 2 weeks. ZIP12−/− rats demonstrated lower pulmonary artery pressures, right ventricular hypertrophy and vascular remodelling than wild-type rats (FIG. 4a-c; FIG. 14a-d) with ZIP12+/− rats exhibiting an intermediate phenotype. Wild-type rats resembled WKY rats after exposure to hypoxia showing markedly increased lung ZIP12 expression in the remodeled pulmonary arterioles, in contrast to the absence of expression in ZIP12−/− rats (FIG. 4d-e). Comparison of the ZIP12−/− response to hypoxia with the WKY and F344 parental strains reveals that mutation of Slc39a12 is responsible for about 50% of the resistance observed in the F344 strain, highlighting the importance of Slc39a12 as a hypoxia-susceptibility gene but also suggesting that other genes yet to be identified may also contribute.

Systemic blood pressure and cardiac output in the hypoxic ZIP12−/− rats was similar to that of wild-type rats (FIG. 14e-g) indicating that the reduced pulmonary artery pressures in the ZIP12−/− rat in chronic hypoxia is due to reduced pulmonary vascular resistance (PVR; mean pulmonary artery pressure=PVR×cardiac output). Bot vascular tone and structural remodeling contribute to PVR, and increased pulmonary vascular tone precedes the structural changes. ZIP12 expression may increase PVR by increasing pulmonary vascular tone. Zinc-thiolate signaling has been reported to mediate the constriction of pulmonary microvascular endothelial cells in acute hypoxia through activation of protein kinase C and inhibition of myosin light chain phosphatase, inducing stress fibre formation and endothelial cell contraction (Bernal, P. J. et al. A role for zinc in regulating hypoxia-induced contractile events in pulmonary endothelium. Am J Physiol Lung Cell Mol Physiol 300, L874-886, doi:10.1152/ajplung.00328.2010, 2011). The inventors have shown that ZIP12 targeted siRNA attenuates stress fibre formation in human pulmonary vascular smooth muscle cells cultured in hypoxia (FIG. 15a-b). But given the time-dependent induction of ZIP12 expression in pulmonary vasculature by hypoxia, the main contribution of ZIP12 is likely to be in regulating the response to chronic rather than acute hypoxia. In further support of a direct effect on structural remodelling of pulmonary arterioles, the inventors investigated angiogenesis ex vivo using pulmonary arteriole rings dissected from ZIP12−/− and wild-type rats. Vascular outgrowth from ZIP12−/− vessels m response to hypoxia was attenuated compared to vessels from wild-type rats (FIG. 15c-d).

The underlying mechanisms through which ZIP12 affects hypoxic responses remain to be defined. Excess intracellular zinc concentrations mediated by upregulation of ZIP family members have been observed in a variety of tumour tissues and linked to cell proliferation and survival (ZHANG, Y. et al. ZIP4 regulates pancreatic cancer cell growth by activating IL-6/STAT3 pathway through zinc finger transcription factor CREB. Clinical cancer research: an official journal of the American Association for Cancer Research 16, 1423-1430, doi:10.1158/1078-0432.CCR-09-2405, 2010; GRATTAN, B. J. & FREAKE, H. C. Zinc and cancer: implications for LIV-1 in breast cancer. Nutrients 4, 648-675, doi: 100.3390/nu4070648, 2012; CHEN, Q. G. et al. T e role of zinc transporter ZIP4 in prostate carcinoma. Urologic oncology 30, 90-911, doi:10.1016/j.urolonc.2010.11.010, 2012). Zinc is a structural component of a large variety of intracellular proteins, including enzymes and transcription factors. Zinc binding motifs have been identified in drug targets for pulmonary hypertension, for example, phosphodiesterase type 5 (PDE5) and histone deacetylases (ZHAO, L. et a Sildenafil inhibits hypoxia-induced pulmonary hypertension. Circulation 104, 424-428, 2001; ZHAO, L. et al. Histone deacetylation inhibition in pulmonary hypertension, therapeutic potential of valproic acid and suberoylanilide hydroxamic acid. Circulation 126, 455-467, doi:10.1161/CIRCULATIONAHA.112.103176, 2012). Reduced ZIP12 expression and intranet labile zinc levels would be expected to inhibit PDE5 activity (FRANCIS, S. H., COLBRAN, J. L., MCALLISTER-LUCAS, L. M. & CORBIN, J. D. zinc interactions and conserved motifs of the cGMP-binding cGMP-specific phosphodiesterase suggest that it is a zinc hydrolase. The Journal of biological chemistry 269, 22477-22480, 1994), and the inventors have previously shown that PDE5 inhibition attenuated pulmonary vascular smooth muscle proliferation in culture WHARTON, J. et al. Antiproliferative effects of phosphodiesterase type 5 inhibition in human pulmonary artery cells. American journal of respiratory and critical care medicine 172, 105-113, doi:10.1164/rccm.200411-1587OC, 2005).

Example 7—the Broader Applicability of the Invention

Following on from the inventors' demonstration that ZIP12 is hypoxia-inducible and a key regulator of the pulmonary vascular response to chronic alveolar hypoxia exposure, they examined lung ZIP12 expression in other presentations of pulmonary hypertension where tissue hypoxia is an important driver of pathology. Again, in contrast to healthy lungs, ZIP12 expression was clearly evident in lung tissues from chronic iron deficient rats (COTRONEO, E. et al. Iron Homeostasis and Pulmonary Hypertension: Iron Deficiency Leads to Pulmonary Vascular Remodeling in the Rat. Circulation research, doi:10.1161/CIRCRESAHA.116.305265, 2015). and rats exposed to monocrotaline, as well as patients with idiopathic pulmonary arterial hypertension (IPAH) (TUDER, R. M. et al. Expression of angiogenesis-related molecules in plexiform lesions in severe pulmonary hypertension: evidence for a process of disordered angiogenesis. The Journal of pathology 195, 367-374, doi:10.1002/path.953, 2001) (FIG. 4f), prominent in the remodeled pulmonary vasculature as identified by co-staining with smooth muscle actin (FIG. 4g). HIF-activation in these tissues was confirmed by upregulation of carbonic anhydrase IX, a recognized HIF-regulated biochemical signature of tissue hypoxia (BEASLEY, N. J. et al. Carbonic anhydrase IX, an endogenous hypoxia marker, expression in head and neck squamous cell carcinoma and its relationship to hypoxia, necrosis, and microvessel density. Cancer research 61, 5262-5267, 2001) (FIG. 16). Interestingly, the F344 rat strain has previously been reported to exhibit some resistance to monocrotaline-induced pulmonary hypertension (PAN, L. C., WILSON, D. W. & SEGALL, H. J. Strain Differences in the Response of Fischer-344 and Sprague-Dawley Rats to Monocrotaline Induced Pulmonary Vascular-Disease. Toxicology 79, 21-35, doi:Doi 10.1016/0300-483x(93)90203-5, 1993: this was recapitulated in the ZIP12−/− rat (FIG. 17). These data signal a fundamental role for ZIP12 in the regulation of pulmonary vascular homeostasis in hypoxic stress relevant to the pathogenesis of pulmonary hypertension beyond that associated with life in a low oxygen atmosphere. Pulmonary hypertension can occur in isolation (idiopathic pulmonary arterial hypertension) or accompany other diseases, such as congenital heart disease and chronic obstructive airways disease. The current treatments for pulmonary hypertension centre on the pharmacological manipulation of signaling mechanisms used by vasoactive factors and have limited therapeutic benefit. The inventors' observations open a new avenue of research into the therapeutic potential of ZIP12 inhibition and suppressed excursions of intracellular free zinc as a novel strategy for preventing or treating pulmonary hypertension.

The invention claimed is:

1. A method of treating hypoxic-induced pulmonary hypertension in a subject, the method comprising inhibiting ZIP12 protein levels by genetic disruption of the Slc39a12 gene using a Zinc finger nuclease technolog, or inhibiting Slc39a12 gene expression using an interfering nucleic acid, wherein the interfering nucleic acid is an antisense oligonucleotide, an siRNA, or a dsRNA, in a subject in need of such treatment.

2. A method according to claim 1, wherein the method comprisesinhibiting Slc39a12 gene expression using the interfering nucleicacid, wherein the interfering nucleicacid is the antisense oligonucleotide, the siRNA, or the dsRNA.

3. A method according to claim 1, wherein the antisense oligonucleotide, siRNA, or dsRNA specifically bindstoa portion of the mRNA product of Slc39a12.

4. A method according to claim 1, whereinthe method comprises disrupting the Slc39a12 gene by usingthe Zincfingernuclease technology.

5. A method according to claim 1, whereinthe Slc39a12 gene is disrupted or the Slc39a12 gene expression isinhibited, bytargeting exon 8 ofthe Slc39a12 gene.

* * * * *

```
                        SEQUENCE LISTING

<160> NUMBER OF SEQ ID NOS: 48

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
gcaatggttt tccacagtga                                                  20

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
gcgcactgag gctttaagaa                                                  20

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
tttcccaacc tgggtcctat                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
agcagccaaa aagcttgcta                                                  20

<210> SEQ ID NO 5
<211> LENGTH: 20
<212> TYPE: DNA
<213> ORGANISM: Artificial Sequence
<220> FEATURE:
```

```
<223> OTHER INFORMATION: Synthetic Primer

<400> SEQUENCE: 5
cctttccctt tccactctcc                                                   20

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
ggtaagggtg gtggcagtag                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
cagacaaaac cccagcattt                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
agcagaaaga accaggcaga                                                   20

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
ccagacacca acatcacacc                                                   20

<210> SEQ ID NO 10
<211> LENGTH: 23
<212> TYPE: DNA
<213> ORGANISM: Artificial Sequence
<220> FEATURE:
<223> OTHER INFORMATION: Synthetic Primer

<400> SEQUENCE: 10
ccttcatgtg tggagtgttt atg                                               23

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
cactcacttg ctggctgtct                                                   20
```

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
gagaagaagc tggagaggca                                        20

<210> SEQ ID NO 13
<211> LENGTH: 23
<212> TYPE: DNA
<213> ORGANISM: Artificial Sequence
<220> FEATURE:
<223> OTHER INFORMATION: Synthetic Primer

<400> SEQUENCE: 13
tgccgctatt aaaaagtaac tgc                                    23

<210> SEQ ID NO 14
<211> LENGTH: 22
<212> TYPE: DNA
<213> ORGANISM: Artificial Sequence
<220> FEATURE:
<223> OTHER INFORMATION: Synthetic Primer

<400> SEQUENCE: 14
ccaaaggcat aaaaatcttt cc                                     22

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer

<400> SEQUENCE: 15
gaaaggatgg caggttttg                                         20

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
tccacaggct cactgtcact                                        20

<210> SEQ ID NO 17
<211> LENGTH: 20
<212> TYPE: DNA
<213> ORGANISM: Artificial Sequence
<220> FEATURE:
<223> OTHER INFORMATION: Synthetic Primer

<400> SEQUENCE: 17
tgggttcttt cattccttgc                                        20

<210> SEQ ID NO 18
<211> LENGTH: 20
<212> TYPE: DNA
<213> ORGANISM: Artificial Sequence
<220> FEATURE:
<223> OTHER INFORMATION: Synthetic Primer

<400> SEQUENCE: 18
gctcacccac acacacattc								20

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer

<400> SEQUENCE: 19
ccctgctttc tgctttgaac								20

<210> SEQ ID NO 20
<211> LENGTH: 23
<212> TYPE: DNA
<213> ORGANISM: Artificial Sequence
<220> FEATURE:
<223> OTHER INFORMATION: Synthetic Primer

<400> SEQUENCE: 20
tgcatatacg aattacagct caa							23

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer

<400> SEQUENCE: 21
caccatgagc tcagcagtgt								20

<210> SEQ ID NO 22
<211> LENGTH: 20
<212> TYPE: DNA
<213> ORGANISM: Artificial Sequence
<220> FEATURE:
<223> OTHER INFORMATION: Synthetic Primer

<400> SEQUENCE: 22
acaccgtctg gctctctcag								20

<210> SEQ ID NO 23
<211> LENGTH: 20
<212> TYPE: DNA
<213> ORGANISM: Artificial Sequence
<220> FEATURE:
<223> OTHER INFORMATION: Synthetic Primer

<400> SEQUENCE: 23
acctttggct cggtcctatc								20

<210> SEQ ID NO 24
<211> LENGTH: 20
<212> TYPE: DNA
<213> ORGANISM: Artificial Sequence
<220> FEATURE:
<223> OTHER INFORMATION: Synthetic Primer

<400> SEQUENCE: 24
aaacttgggt accagcacca								20

<210> SEQ ID NO 25
<211> LENGTH: 20

```
<212> TYPE: DNA
<213> ORGANISM: Artificial Sequence
<220> FEATURE:
<223> OTHER INFORMATION: Synthetic Primer

<400> SEQUENCE: 25
cactacacct cccaacgtcc                                              20

<210> SEQ ID NO 26
<211> LENGTH: 22
<212> TYPE: DNA
<213> ORGANISM: Artificial Sequence
<220> FEATURE:
<223> OTHER INFORMATION: Synthetic Primer

<400> SEQUENCE: 26
ctgttgtgcc tcctgactaa tg                                           22

<210> SEQ ID NO 27
<211> LENGTH: 20
<212> TYPE: DNA
<213> ORGANISM: Artificial Sequence
<220> FEATURE:
<223> OTHER INFORMATION: Synthetic Primer

<400> SEQUENCE: 27
ggtcggcatt atggctaaga                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic Primer

<400> SEQUENCE: 28
ctatagcctc tagggagggg                                              20

<210> SEQ ID NO 29
<211> LENGTH: 19
<212> TYPE: DNA
<213> ORGANISM: Artificial Sequence
<220> FEATURE:
<223> OTHER INFORMATION: Synthetic Primer

<400> SEQUENCE: 29
ggggtccagc acttagcat                                               19

<210> SEQ ID NO 30
<211> LENGTH: 20
<212> TYPE: DNA
<213> ORGANISM: Artificial Sequence
<220> FEATURE:
<223> OTHER INFORMATION: Synthetic Primer

<400> SEQUENCE: 30
gttttgatca tgggacgtt                                               20

<210> SEQ ID NO 31
<211> LENGTH: 24
<212> TYPE: DNA
<213> ORGANISM: Artificial Sequence
<220> FEATURE:
<223> OTHER INFORMATION: Synthetic Primer

<400> SEQUENCE: 31
```

```
cacatgtcta acttgccaca taca                                            24

<210> SEQ ID NO 32
<211> LENGTH: 22
<212> TYPE: DNA
<213> ORGANISM: Artificial Sequence
<220> FEATURE:
<223> OTHER INFORMATION: Synthetic Primer

<400> SEQUENCE: 32
tttgctgttt cttgttcatg tg                                              22

<210> SEQ ID NO 33
<211> LENGTH: 21
<212> TYPE: DNA
<213> ORGANISM: Artificial Sequence
<220> FEATURE:
<223> OTHER INFORMATION: Synthetic Primer

<400> SEQUENCE: 33
tccatgtttt atcaccggaa g                                               21

<210> SEQ ID NO 34
<211> LENGTH: 20
<212> TYPE: DNA
<213> ORGANISM: Artificial Sequence
<220> FEATURE:
<223> OTHER INFORMATION: Synthetic Primer

<400> SEQUENCE: 34
atctgatgca tgccatagcc                                                 20

<210> SEQ ID NO 35
<211> LENGTH: 20
<212> TYPE: DNA
<213> ORGANISM: Artificial Sequence
<220> FEATURE:
<223> OTHER INFORMATION: Synthetic Primer

<400> SEQUENCE: 35
aagttagcct tccccaagga                                                 20

<210> SEQ ID NO 36
<211> LENGTH: 20
<212> TYPE: DNA
<213> ORGANISM: Artificial Sequence
<220> FEATURE:
<223> OTHER INFORMATION: Synthetic Primer

<400> SEQUENCE: 36
tctggtcttt cccatgttcc                                                 20

<210> SEQ ID NO 37
<211> LENGTH: 20
<212> TYPE: DNA
<213> ORGANISM: Artificial Sequence
<220> FEATURE:
<223> OTHER INFORMATION: Synthetic Primer

<400> SEQUENCE: 37
ttaagaaggg caagcaagga                                                 20

<210> SEQ ID NO 38
<211> LENGTH: 21
<212> TYPE: DNA
<213> ORGANISM: Artificial Sequence
```

<220> FEATURE:
<223> OTHER INFORMATION: Synthetic Primer

<400> SEQUENCE: 38
tccccataaa aagaaaagga a                                                    21

<210> SEQ ID NO 39
<211> LENGTH: 20
<212> TYPE: DNA
<213> ORGANISM: Artificial Sequence
<220> FEATURE:
<223> OTHER INFORMATION: Synthetic Primer

<400> SEQUENCE: 39
tcccactggt caatccattt                                                      20

<210> SEQ ID NO 40
<211> LENGTH: 21
<212> TYPE: DNA
<213> ORGANISM: Artificial Sequence
<220> FEATURE:
<223> OTHER INFORMATION: Synthetic Primer

<400> SEQUENCE: 40
acatgcagac agaacattcc t                                                    21

<210> SEQ ID NO 41
<211> LENGTH: 688
<212> TYPE: PRT
<213> ORGANISM: Rattus norvegicus

<400> SEQUENCE: 41

Met Cys Phe Trp Thr Glu Leu Ser Val Trp Val Leu Val Ser His
1               5                   10                  15

Ser Phe Ser Leu Ala Ser Ser Thr Glu Thr Ser Lys Ala Leu Thr Gln
                20                  25                  30

Asp Asn Ser Arg Val Gly Ser His Ser Leu Leu Glu Val Leu Arg Val
            35                  40                  45

Leu Ser Ala Gly Asp Asp Arg Ser Leu Asn His Pro Gln Ser Leu Ile
        50                  55                  60

Lys Ile Leu Leu Glu Arg Thr Gly Cys Pro Gln Arg Thr Asp Gly Thr
65                  70                  75                  80

Gln Glu Asp Cys Lys Leu Cys Leu Glu Pro Asp Ala Leu Ser Leu Thr
                85                  90                  95

Ala Gly Gly Asp Leu Glu Asp Glu Leu Arg Glu Val Val Gln Arg
            100                 105                 110

Val Ser Leu Leu Leu Leu Tyr Tyr Ile Ile His Gln Glu Ile Cys
        115                 120                 125

Ser Ser Lys Leu Asn Met Ser Asn Arg Glu Tyr Glu Phe Tyr Leu His
130                 135                 140

Ser Leu Leu Ser Leu Arg Gln Asp Glu Asp Ser Tyr Phe Leu Ser Glu
145                 150                 155                 160

Lys Glu Thr Asp Asp Ile Leu Ala Ser Thr Arg Lys Tyr Phe Gly Thr
                165                 170                 175

Ser Thr Ser Pro Cys Met Glu Thr Lys Ile Leu Gln Arg Glu Ser Gly
            180                 185                 190

Ile Gln Ser Ser Asn Gly Ala Asp Glu Lys Met Leu Pro Gln Leu Ala
        195                 200                 205

Ala Thr Ile Ile Ala Leu Ser Leu Gln Gly Val Cys Leu Gly Arg Lys

-continued

```
             210                 215                 220
Asp Ser Pro Ser Pro Asp Asp Phe Thr Glu Tyr Ile Phe Ser Phe Leu
225                 230                 235                 240

Asn Arg Thr Asn Ala Leu His Leu Ser Glu Leu Glu Glu Leu Leu Asn
                245                 250                 255

Met Leu Ser Thr Arg Arg Ala Cys Thr Lys Ile Asn Thr Leu His Glu
            260                 265                 270

His Gln Arg Lys Gln Asn Thr Ala Val His Gly Leu Arg Asp Pro Lys
        275                 280                 285

Ser Ala Ala Met Asp Lys Val Ser Gly Asp His Ser Val Ser Trp
290                 295                 300

Asp Gln Ala Cys Phe Ser Ala Gln Gln Leu Val Glu Ile Phe Leu Gln
305                 310                 315                 320

Asn His Ser Ser Leu Ser Ile Ser Lys Glu Asp Phe Lys Gln Leu Ser
                325                 330                 335

Pro Gly Ile Ile Gln Gln Leu Leu Ser Cys Ser Cys Gln Val Pro Arg
            340                 345                 350

Asp Gln Lys Ala Lys Pro Pro Thr Thr Leu Glu Lys Tyr Gly Tyr
        355                 360                 365

Ser Thr Val Ala Val Thr Leu Leu Thr Leu Gly Ser Met Leu Gly Thr
370                 375                 380

Ala Leu Val Leu Phe His Ser Cys Glu Glu Asn Tyr Ser Leu Ile Leu
385                 390                 395                 400

Gln Leu Phe Val Gly Leu Ala Val Gly Thr Leu Ser Gly Asp Ala Leu
                405                 410                 415

Leu His Leu Ile Pro Gln Val Leu Gly Leu His Lys Gln Glu Ala Glu
            420                 425                 430

Leu Gly His Phe His Glu Ser Gln Ser Pro Ile Trp Lys Leu Leu Gly
        435                 440                 445

Leu Leu Gly Gly Ile His Gly Phe Phe Leu Ile Glu Lys Cys Phe Ile
450                 455                 460

Leu Leu Val Ser Pro Asn Thr Lys Gly Leu Pro Leu Val Asn Gly His
465                 470                 475                 480

Ala Gly His Thr His His Leu Gly Leu Ser Pro Glu Leu Asn Asp Gln
                485                 490                 495

Ser Gly Gly Gly Lys Ser Ile Ser Thr Ile Gln Leu Lys Gly Pro Glu
            500                 505                 510

Asp Ser Gln Thr Ala Glu Leu Pro Lys Gly Asn Val Pro Ala Ser Asn
        515                 520                 525

Arg Asn Arg Lys Thr Ile Ser Leu Leu Ala Val Met Val Leu Val Gly
530                 535                 540

Asp Gly Leu His Asn Phe Ala Asp Gly Leu Val Ile Gly Thr Ala Phe
545                 550                 555                 560

Ser Ser Ser Leu Glu Ser Gly Val Thr Thr Ile Ala Ile Leu Cys
                565                 570                 575

His Glu Ile Pro His Glu Met Gly Asp Phe Ala Val Leu Leu Ser Ser
            580                 585                 590

Gly Leu Ser Ile Arg Thr Ala Ile Leu Met Asn Phe Leu Ser Ala Leu
        595                 600                 605

Thr Ala Phe Ile Gly Leu Tyr Ile Gly Leu Ser Val Ser Ala Asp Pro
610                 615                 620

Arg Val Gln Asp Trp Ile Leu Thr Val Thr Ala Gly Met Phe Leu Tyr
625                 630                 635                 640
```

Leu Ser Leu Val Gly Met Leu Pro Glu Met Thr His Val Gln Thr Gln
                645                 650                 655

Arg Pro Trp Met Thr Phe Leu Leu Gln Asn Val Gly Leu Val Leu Gly
            660                 665                 670

Trp Phe Ser Leu Leu Leu Ala Val Tyr Glu Gln Asn Ile Lys Ile
        675                 680                 685

<210> SEQ ID NO 42
<211> LENGTH: 553
<212> TYPE: PRT
<213> ORGANISM: Rattus norvegicus

<400> SEQUENCE: 42

Met Cys Phe Trp Thr Glu Leu Ser Val Trp Val Leu Val Ser His
1               5                   10                  15

Ser Phe Ser Leu Ala Ser Ser Thr Glu Thr Ser Lys Ala Leu Thr Gln
                20                  25                  30

Asp Asn Ser Arg Val Gly Ser His Ser Leu Leu Glu Val Leu Arg Val
            35                  40                  45

Leu Ser Ala Gly Asp Asp Arg Ser Leu Asn His Pro Gln Ser Leu Ile
50                  55                  60

Lys Ile Leu Leu Glu Arg Thr Gly Cys Pro Gln Arg Thr Asp Gly Thr
65                  70                  75                  80

Gln Glu Asp Cys Lys Leu Cys Leu Glu Pro Asp Ala Leu Ser Leu Thr
                85                  90                  95

Ala Gly Gly Asp Leu Glu Asp Glu Leu Arg Glu Val Val Gln Arg
            100                 105                 110

Val Ser Leu Leu Leu Tyr Tyr Ile Ile His Gln Glu Ile Cys
        115                 120                 125

Ser Ser Lys Leu Asn Met Ser Asn Arg Glu Tyr Glu Phe Tyr Leu His
        130                 135                 140

Ser Leu Leu Ser Leu Arg Gln Asp Glu Asp Ser Tyr Phe Leu Ser Glu
145                 150                 155                 160

Lys Glu Thr Asp Asp Ile Leu Ala Ser Thr Arg Lys Tyr Phe Gly Thr
                165                 170                 175

Ser Thr Ser Pro Cys Met Glu Thr Lys Ile Leu Gln Arg Glu Ser Gly
            180                 185                 190

Ile Gln Ser Ser Asn Gly Ala Asp Glu Lys Met Leu Pro Gln Leu Ala
        195                 200                 205

Ala Thr Ile Ile Ala Leu Ser Leu Gln Gly Val Cys Leu Gly Arg Lys
        210                 215                 220

Asp Ser Pro Ser Pro Asp Asp Phe Thr Glu Tyr Ile Phe Ser Phe Leu
225                 230                 235                 240

Asn Arg Thr Asn Ala Leu His Leu Ser Glu Leu Glu Glu Leu Leu Asn
                245                 250                 255

Met Leu Ser Thr Arg Arg Ala Cys Thr Lys Ile Asn Thr Leu His Glu
            260                 265                 270

His Gln Arg Lys Gln Asn Thr Ala Val His Gly Leu Arg Asp Pro Lys
        275                 280                 285

Ser Ala Ala Ala Met Asp Lys Val Ser Gly Asp His Ser Val Ser Trp
        290                 295                 300

Asp Gln Ala Cys Phe Ser Ala Gln Gln Leu Val Glu Ile Phe Leu Gln
305                 310                 315                 320

Asn His Ser Ser Leu Ser Ile Ser Lys Glu Asp Phe Lys Gln Leu Ser

```
            325                 330                 335
Pro Gly Ile Ile Gln Gln Leu Leu Ser Cys Ser Cys Gln Val Pro Arg
            340                 345                 350
Asp Gln Lys Ala Lys Pro Pro Thr Thr Leu Glu Lys Tyr Gly Tyr
            355                 360                 365
Ser Thr Val Ala Val Thr Leu Leu Thr Leu Gly Ser Met Leu Gly Thr
    370                 375                 380
Ala Leu Val Leu Phe His Ser Cys Glu Glu Asn Tyr Ser Leu Ile Leu
385                 390                 395                 400
Gln Leu Phe Val Gly Leu Ala Val Gly Thr Leu Ser Gly Asp Ala Leu
                405                 410                 415
Leu His Leu Ile Pro Gln Val Leu Gly Leu His Lys Gln Glu Ala Glu
                420                 425                 430
Leu Gly His Phe His Glu Ser Gln Ser Pro Ile Trp Lys Leu Leu Gly
                435                 440                 445
Leu Leu Gly Gly Ile His Gly Phe Phe Leu Ile Glu Lys Cys Phe Ile
                450                 455                 460
Leu Leu Val Ser Pro Asn Thr Lys Gly Leu Pro Leu Val Asn Gly His
465                 470                 475                 480
Ala Gly His Thr His His Leu Gly Leu Ser Pro Glu Leu Asn Asp Gln
                485                 490                 495
Ser Gly Gly Gly Lys Ser Ile Ser Thr Ile Gln Leu Lys Gly Pro Glu
                500                 505                 510
Asp Ser Gln Thr Ala Glu Leu Pro Lys Gly Asn Val Pro Ala Ser Asn
                515                 520                 525
Arg Asn Arg Lys Thr Ile Ser Leu Leu Ala Val Met Val Leu Val Glu
                530                 535                 540
Met Ala Cys Thr Ile Leu Pro Met Ala
545                 550

<210> SEQ ID NO 43
<211> LENGTH: 61
<212> TYPE: DNA
<213> ORGANISM: Artificial Sequence
<220> FEATURE:
<223> OTHER INFORMATION: Synthetic nucleic acid

<400> SEQUENCE: 43
gactaatttt acactgtcct tgttctgcag ggcctgccat tagttaatgg acatgcagga      60
c                                                                      61

<210> SEQ ID NO 44
<211> LENGTH: 48
<212> TYPE: DNA
<213> ORGANISM: Artificial Sequence
<220> FEATURE:
<223> OTHER INFORMATION: Synthetic nucleic acid

<400> SEQUENCE: 44
ggtgggtatg tcctgcatgt ccattaacta atggcaggcc cagcagaa                   48

<210> SEQ ID NO 45
<211> LENGTH: 79
<212> TYPE: DNA
<213> ORGANISM: Rattus norvegicus

<400> SEQUENCE: 45
ccttgttctg cagggcctgc cattagttaa tggacatgca ggacatacccc accatcttgg     60
```

```
actcagtcct gagttaaat                                                    79

<210> SEQ ID NO 46
<211> LENGTH: 77
<212> TYPE: DNA
<213> ORGANISM: Artificial Sequence
<220> FEATURE:
<223> OTHER INFORMATION: Mutated Construct

<400> SEQUENCE: 46
ccttgttctg cagggcctgc catttaaatg gacatgcagg acatacccac catcttggac       60
tcagtcctga gttaaat                                                      77

<210> SEQ ID NO 47
<211> LENGTH: 21
<212> TYPE: PRT
<213> ORGANISM: Rattus norvegicus

<400> SEQUENCE: 47

Gly Leu Pro Leu Val Asn Gly His Ala Gly His Thr His His Leu Gly
1               5                   10                  15

Leu Ser Pro Glu Leu
            20

<210> SEQ ID NO 48
<211> LENGTH: 15
<212> TYPE: PRT
<213> ORGANISM: Artificial Sequence
<220> FEATURE:
<223> OTHER INFORMATION: Mutated Construct

<400> SEQUENCE: 48

Phe Lys Trp Thr Cys Arg Thr Tyr Pro Pro Ser Trp Thr Gln Ser
1               5                   10                  15
```